US007160540B2

(12) United States Patent
Nelsestuen

(10) Patent No.: US 7,160,540 B2
(45) Date of Patent: Jan. 9, 2007

(54) METHODS FOR DETECTING ACTIVITY OF CLOTTINGS FACTORS

(75) Inventor: Gary L. Nelsestuen, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 354 days.

(21) Appl. No.: 10/312,685

(22) PCT Filed: Jun. 26, 2001

(86) PCT No.: PCT/US01/20307

§ 371 (c)(1),
(2), (4) Date: Dec. 30, 2002

(87) PCT Pub. No.: WO02/03075

PCT Pub. Date: Jan. 10, 2002

(65) Prior Publication Data

US 2003/0211460 A1 Nov. 13, 2003

Related U.S. Application Data

(63) Continuation-in-part of application No. 09/607,716, filed on Jun. 30, 2000, now Pat. No. 6,423,826.

(51) Int. Cl.
*A61K 38/46* (2006.01)
*A61K 38/00* (2006.01)
*C12N 11/08* (2006.01)

(52) U.S. Cl. .................. 424/94.6; 435/180; 514/2
(58) Field of Classification Search ................ 435/180, 435/181; 424/94.2, 94.6; 514/2
See application file for complete search history.

(56) References Cited

U.S. PATENT DOCUMENTS

| 5,091,304 | A | * | 2/1992 | La Duca et al. ............... 435/13 |
| 5,217,705 | A | | 6/1993 | Reno et al. |
| 5,318,910 | A | | 6/1994 | LaDuca |
| 5,580,560 | A | | 12/1996 | Nicolaisen et al. |
| 5,788,965 | A | | 8/1998 | Berkner et al. |
| 5,817,788 | A | | 10/1998 | Berkner et al. |
| 5,824,639 | A | | 10/1998 | Berkner |
| 5,833,982 | A | | 11/1998 | Berkner et al. |
| 5,861,374 | A | | 1/1999 | Berkner et al. |
| 5,986,065 | A | * | 11/1999 | Wong et al. ............ 530/388.22 |
| 5,990,079 | A | | 11/1999 | Wolf et al. |
| 6,017,882 | A | | 1/2000 | Nelsestuen |
| 6,037,452 | A | | 3/2000 | Minamino et al. |
| 6,110,721 | A | | 8/2000 | Gibbs et al. |
| 6,214,333 | B1 | * | 4/2001 | Zoldhelyi et al. .......... 424/93.1 |

FOREIGN PATENT DOCUMENTS

| JP | 08092294 | 4/1996 |
| WO | WO 91/09125 | 6/1991 |
| WO | WO 94/29370 | 12/1994 |
| WO | WO 97/11957 | 4/1997 |
| WO | WO 98/32466 | 7/1998 |
| WO | WO 99/20767 | 4/1999 |
| WO | WO 00/66753 | 11/2000 |
| WO | WO 01/02439 | 1/2001 |
| WO | WO 01/58935 | 8/2001 |
| WO | WO 02/02764 | 1/2002 |
| WO | WO 02/03075 | 1/2002 |

OTHER PUBLICATIONS

Webster's II New Riverside Dictionary (1984) (Houghton-Mifflin: Boston, MA) p. 667.*
Towne et al. "Abnormalities of the fibrinolytic system as a cause of upper extremity ischemia: a preliminary report," J. Vascular Surgery, (1988) 7(5): 661-666 (abstract only).*
McKean et al. "Future therapies for the prevention and treatment of venous and arterial thrombosis," Expert Opinion of Invest. Drugs (1998) 7(5): 687-690.*
Ambrose et al., "Evaluation of the TAS Analyzer and the Low-Range Heparin Management Test in Patients Undergoing Extracorporeal Membrane Oxygenation," *Clin. Chem.*, 2001, 47(5):858-866.
Banner et al., "The crystal structure of the complex of blood coagulation factor VIIa with soluble tissue factor," *Nature*, 1996, 380:41-46.
Beauchamp et al., "A New Procedure for the Synthesis of Polyethylene Glycol-Protein Adducts; Effects on Function, Receptor Recognition, and Clearance of Superoxide Dismutase, Lactoferrin, and $\alpha_2$-Macroglobulin," *Analyt. Biochem.*, 1983, 131:25-33.
Dahlbäck, "The Protein C Anticoagulant System: Inherited Defects as Basis for Venous Thrombosis," *Thromb. Res.*, 1995, 77:1-43.
Furie and Furie, "The Molecular Basis of Blood Coagulation," *Cell*, 1988, 53:505-518.
Harker et al., "Antothrombotic Strategies Targeting Thrombin Activities, Thrombin Receptors and Thrombin Generation," *Thromb. Haemost.*, 1997, 78:736-741.
Hedner and Falch, "Recombinant Activated Factor VII in the Treatment of Bleeding Episodes in Patients With Inherited and Acquired Bleeding Disorders," *Transfus. Med. Rev.*, 1993, 7(2):78-83.
Lee et al., "Prolonged Circulating Lives of Single-Chain Fv Proteins Conjugated with Polyethylene Glycol: A Comparison of Conjugation Chemistries and Compounds," *Bioconjugate Chem.*, 1999, 10:973-981.
Luo et al., "Spontaneous calcification of arteries and cartilage in mice lacking matrix GLA protein," *Nature*, 1997, 386:78-81.
Manfioletti et al., "The Protein Encoded by a Growth Arrest-Specific Gene (*gas6*) Is a New Member of the Vitamin K-Dependent Proteins Related to Protein S, a Negative Coregulator in the Blood Coagulation Cascade," *Mol. Cell. Biol.*, 1993, 13(8):4976-4985.
McDonald et al., "Comparison of Naturally Occurring Vitamin K-Dependent Proteins: Correlation of Amino Acid Sequences and Membrane Binding Properties Suggests a Membrane Contact Site," *Biochemistry*, 1997, 36:5120-5127.

(Continued)

*Primary Examiner*—Jean C. Witz
*Assistant Examiner*—Susan Hanley
(74) *Attorney, Agent, or Firm*—Fish & Richardson P.C.

(57) ABSTRACT

Whole blood assays and kits are described for evaluating dosage of factor VIIa or activated protein C, as well as for monitoring responsiveness to factor VIIa or activated protein C.

7 Claims, 17 Drawing Sheets

OTHER PUBLICATIONS

Monroe et al., "Platelet activity of high-dose factor VIIa is independen of tissue factor," *Br. J. Haematol.*, 1997, 99:542-547.

Muir and Kent, "The chemical synthesis of proteins," *Curr. Opin. Biotechnol.*, 1993, 4:420-427.

Nelsestuen et al., "Enhancement of Vitamin-K-Dependent Protein Function by Modification of the γ-Carboxyglutamic Acid Domain: Studies of Protein C and Factor VII," *Trends Cardiovasc. Med.*, 1999, 9:162-167.

Nelsestuen et al., "Vitamin K-Dependent Proteins," *Vitam. Horm.*, 2000, 58:355-389.

Shah et al., "Manipulation of the membrane binding site of vitamin K-dependent proteins: Enhanced biological function of human factor VII," *Proc. Natl. Acad. Sci. USA*, 1998, 95:4229-4234.

Shearwater Polymers, Inc., 2000, Catalog, p. 11.

Shearwater Polymers, Inc., 2000, Catalog, p. 20.

Shearwater Polymers, Inc., 2000, Catalog, p. 34.

Shearwater Polymers, Inc., 2000, Catalog, p. 41.

Shen et al., "Enhancement of Human Protein C Function by Site-directed Mutagenesis of the γ-Carboxyglutamic Acid Domain," *J. Biol. Chem.*, 1998, 273(47):31086-31091.

Sørensen et al., "Incorporation of an Active Site Inhibitor in Factor VIIa Alters the Affinity for Tissue Factor," *J. Biol. Chem.*, 1997, 272(18):11863-11868.

Spanier et al., "Heparinless Cardiopulmonary Bypass with Active-Site Blocked Factor IXA: A Preliminary Study on the Dog," *J. Thorac. Cardiovasc. Surg.*, 1998, 115:1179-1188.

Vallette et al., "Construction of mutant and chimeric genes using the polymerase chain reaction," *Nucleic Acids Research*, 1989, 17(2):723-733.

* cited by examiner

METHODS FOR DETECTING ACTIVITY OF CLOTTINGS FACTORS

CROSS REFERENCE TO RELATED APPLICATIONS

This application is a National Stage application under 35 U.S.C. §371 that claims the benefit of PCT/US01/20307, filed Jun. 26, 2001, which is a continuation-in-part of U.S. Ser. No. 09/607,716, filed Jun. 30, 2000, now U.S. Pat. No. 6,423,826.

STATEMENT AS TO FEDERALLY-SPONSORED RESEARCH

Funding for work described herein was provided in part by the federal government, which may have certain rights in the invention.

TECHNICAL FIELD

This invention relates to methods for monitoring patient responsiveness to factor VIIa therapy and methods for managing anticoagulation therapy.

BACKGROUND

Vitamin K-dependent proteins contain 9 to 13 gamma-carboxyglutamic acid residues (Gla) in their amino terminal 45 residues. The Gla residues are produced by enzymes in the liver that utilize vitamin K to carboxylate the side chains of glutamic acid residues in protein precursors. Vitamin K-dependent proteins are involved in a number of biological processes, of which the most well described is blood coagulation (reviewed in Nelsestuen (2000) *Vitam. Horm.* 58:355–389). Vitamin K-dependent proteins include protein Z, protein S, prothrombin (factor II), factor X, factor IX, protein C, factor VII, Gas6, and matrix GLA protein. Factors VII, IX, X and II function in procoagulation processes. Factor VIIa combines with the integral membrane protein, tissue factor (TF), to catalyze the initial step of blood coagulation. A VIIa/TF complex can activate factor IX, factor X, or can autoactivate other factor VII molecules. Factor IXa and Xa continue the coagulation cascade. A popular model suggests initiation of coagulation by appearance of TF at the site of tissue damage. The VIIa associates with membrane-bound tissue factor through protein-protein binding plus VIIa-membrane binding. Protein C, protein S, and protein Z serve in anticoagulation roles. Gas6 is a growth arrest hormone encoded by growth arrest-specific gene 6 (gas6) and is related to protein S. See, Manfioletti et al. (1993) *Mol. Cell. Biol.* 13:4976–4985. Matrix GLA protein normally is found in bone and is critical to prevention of calcification of soft tissues in the circulation. Luo et al. (1997) *Nature* 386:78–81.

The regulation of blood coagulation is a process that presents a number of leading health problems, including both the failure to form blood clots as well as thrombosis, the formation of unwanted blood clots. Agents that prevent unwanted clots are used in many situations and a variety of agents are available. Unfortunately, most current therapies have undesirable side effects. Orally administered anticoagulants such as Warfarin act by inhibiting the action of vitamin K in the liver, thereby preventing complete carboxylation of glutamic acid residues in the vitamin K-dependent proteins, resulting in a lowered concentration of active proteins in the circulatory system and reduced ability to form clots. Warfarin therapy is complicated by the competitive nature of the drug with its target. Fluctuations of dietary vitamin K can result in an over-dose or under-dose of Warfarin. Fluctuations in coagulation activity are an undesirable outcome of this therapy.

Injected substances such as heparin, including low molecular weight heparin, also are commonly used anticoagulants. Again, these compounds are subject to overdose and must be carefully monitored.

A newer category of anticoagulants includes active-site modified vitamin K-dependent clotting factors such as factor VIIa and IXa. The active sites are blocked by serine protease inhibitors such as chloromethylketone derivatives of amino acids or short peptides. The active site-modified proteins retain the ability to form complexes with their respective cofactors, but are inactive, thereby producing no enzyme activity and preventing complexing of the cofactor with the respective active enzymes. Thus, active-site modified Factor VIIa, denoted factor VIIai, still binds tissue factor, but does not have enzyme activity. Active site-modified proteins appear to have very beneficial anti-coagulant properties with few undesirable side affects. For example, factor VIIai has been shown to lower platelet deposition at the site of surgery, an important indicator of anti-coagulation action. While this also can be accomplished by heparin or other anticoagulants, factor VIIai was unique in that its administration was not accompanied by increased bleeding time or blood loss. Administration of anti-TF antibodies or factor IXai also produced similar results. See, Harker et al. (1997) *Thromb. Haemost.* 78:736–741; and Spanier et al. (1998) *J. Thorac. Cardiovasc. Surg.* 115(5):1179–88. In short, these proteins appear to offer the benefits of anticoagulation therapy without the adverse side effects of other anticoagulants. Active site modified factor Xa is another possible anticoagulant in this group. Its cofactor protein is factor Va. Active site modified activated protein C (APC) may also form an effective inhibitor of coagulation. See, Sorensen et al. (1997) *J. Biol. Chem.* 272:11863–11868. Active site modified APC binds to factor Va and prevents factor Xa from binding.

A major inhibition to the use of active site-modified vitamin K-dependent clotting factors is cost. Biosynthesis of vitamin K-dependent proteins is dependent on an intact glutamic acid carboxylation system, which is present in a small number of animal cell types. Overproduction of these proteins is severely limited by this enzyme system. Furthermore, the effective dose of these proteins is high. A common dosage is 1000 µg of VIIai/kg body weight. See, Harker et al. 1997 supra. Current cost (April of 2000) of recombinant factor VIIa is about $0.80 per µg, which severely limits use.

A second problem for several of these proteins is a short lifetime in the circulation system. The situation for factor VIIa illustrates this problem. Factor VII and VIIa have circulation half-times of about 2–4 hours in the human. That is, within 2–4 hours, half of the protein is taken up by other tissues of the body. When factor VIIa is used as a procoagulant to treat certain forms of hemophilia, the standard protocol is to inject VIIa every two hours and at high dosages (45 to 90 µg/kg body weight). See, Hedner et al. (1993) *Transfus. Med. Rev.* 7:78–83. Thus, use of these proteins as procoagulants or anticoagulants (in the case of factor VIIai) requires that the proteins be administered at frequent intervals and at high dosages.

SUMMARY

The invention is based, in part, on modifications to vitamin K-dependent polypeptides that increase their circulation half-life and in some embodiments, their activity. Both outcomes reduce the amount of protein needed to treat clotting disorders as well as decrease the frequency of administration. As a result, costs associated with treating patients can be reduced, allowing the therapies to be made more widely available to individuals in need of pro- or anti-coagulation therapies.

The invention also is based on whole blood assays for monitoring factor VIIa or APC therapy in patients. The whole blood assays described herein allow individual patients to be monitored such that therapies can be tailored, minimizing costs associated with such therapies. In addition, methods for managing anticoagulation therapy are provided, which combines administering acute anticoagulants and chronic anticoagulants to provide superior anticoagulant therapy.

In one aspect, the invention features an isolated vitamin K-dependent polypeptide linked (e.g., directly or indirectly) to a polyethylene glycol (PEG) polymer. The polypeptide can be selected from the group consisting of factor VII, factor II, protein C, protein S, gas6, and bone matrix Gla protein or can be a protease selected from the group consisting of factor VIIa, factor IIa, and activated protein C. Factor VIIa is a particularly useful protease. The protease can be further linked to an active-site inhibition reagent such as a chloromethylketone derivatized amino acid or peptide. In some embodiments, the PEG polymer is linked to the protease via the active-site inhibition reagent.

The invention also features an active-site inhibition reagent linked to a PEG polymer. The reagent can be a chloromethylketone derivatized amino acid or peptide or a phosphohalide derivative.

In another aspect, the invention features an anticoagulant agent that includes two polypeptide monomers, wherein at least one of the polypeptide monomers is a vitamin K-dependent polypeptide, and wherein the polypeptide monomers are covalently linked. The polypeptide monomers can be covalently linked via a bi-functional active-site inhibition reagent. The two polypeptide monomers can be the same or different polypeptides. In some embodiments, each of the two polypeptide monomers is a vitamin K-dependent polypeptide, such as a factor VIIa polypeptide, a factor Xa polypeptide, or a factor IXa polypeptide. The bi-functional active-site inhibition reagent can be linked to a PEG polymer. At least one of the polypeptide monomers also can be directly linked to a PEG polymer.

The invention also features a bifunctional active-site inhibition reagent that includes two covalently linked active-site inhibitors. At least one of the active-site inhibitors can be linked to a PEG polymer.

A method of directly linking a vitamin K-dependent polypeptide to a PEG polymer also is featured. The method includes incubating the PEG polymer with the vitamin K-dependent polypeptide for a time sufficient to link the PEG polymer to the vitamin K-dependent polypeptide, wherein the PEG polymer is reactive with amino groups or carbohydrate groups on the vitamin K-dependent polypeptide.

In yet another aspect, the invention features a method of indirectly linking a vitamin K-dependent polypeptide to a PEG polymer. The method includes providing a PEG-modified, active-site inhibition reagent, wherein the PEG polymer is reactive with amino groups on the active-site inhibition reagent; and incubating the PEG-modified, active-site inhibition reagent with the vitamin K-dependent polypeptide for a time sufficient to link the PEG modified, active-site inhibition reagent to the vitamin K-dependent polypeptide.

A method of making an anticoagulant agent also is featured. The method includes incubating a bi-functional active-site inhibition reagent and at least one vitamin K-dependent polypeptide in the presence of phospholipid for a time sufficient to link the bi-functional active-site inhibition reagent and the vitamin K-dependent polypeptide.

In another aspect, the invention features a pharmaceutical composition that includes an isolated vitamin K-dependent polypeptide linked to a PEG polymer and a pharmaceutically acceptable carrier. The polypeptide and PEG polymer can be indirectly linked. The polypeptide can be a protease selected from the group consisting of factor VIIa, factor IIa, and activated protein C. Factor VIIa is a particularly useful protease. The protease can be further linked to an active-site inhibition reagent such as a chloromethylketone derivatized amino acid or peptide. The PEG polymer can be linked to the protease via the active-site inhibition reagent.

The invention also features a pharmaceutical composition that includes an anticoagulant agent and a pharmaceutical acceptable carrier, wherein the anticoagulant agent includes two polypeptide monomers, wherein at least one of the polypeptide monomers is a vitamin K-dependent polypeptide, and wherein the polypeptide monomers are covalently linked. The polypeptide monomers can be covalently linked via a bi-functional active-site inhibition reagent.

In yet another aspect, the invention features a method for evaluating patient responsiveness to factor VIIa therapy. The method includes obtaining a whole blood sample from a patient, adding factor VIIa to the whole blood sample, and monitoring clotting time of the whole blood sample (e.g., in a device) in the absence of added phospholipid, wherein a significant decrease in clotting time compared to a control sample from the patient in the absence of factor VIIa indicates that the patient is responsive to factor VIIa. Factor VIIa therapy can include administering to the patient factor VIIa linked to a PEG polymer. Activated clotting time further can be monitored in the presence of an activator of the contact phase of coagulation.

The invention also features a method for managing anticoagulation therapy in a patient. The method includes administering an acute phase anticoagulant to the patient during the acute phase of coagulation, e.g., during surgery, and administering a chronic phase anticoagulant, e.g., an active-site inhibited factor VIIa polypeptide, an antibody having specific binding affinity for tissue factor, or tissue factor pathway inhibitor, to the patient during the chronic phase of coagulation. The active-site inhibited factor VIIa polypeptide can be linked to a PEG polymer, as described above. The acute phase anticoagulant can be heparin.

Pharmaceutical compositions that include an active-site inhibited factor VIIa polypeptide and an acute phase anticoagulant also are featured. The active-site inhibited factor VIIa polypeptide can be linked to a PEG polymer, as described above. The PEG polymer can be linked to the active-site inhibited factor VIIa polypeptide via an active-site inhibition reagent.

In yet another aspect, the invention features methods and kits for detecting tissue factor in blood. The method includes obtaining an anticoagulated blood sample, neutralizing factor VIII or factor IX and tissue factor in the anticoagulated blood sample, and assaying the activated clotting time of the anticoagulated and neutralized blood sample in the presence of added factor VIIa. The presence or absence of tissue factor is detected by comparing the clotting time of the anticoagualted and neutralized blood sample to a corresponding anticoagulated blood sample without neutralized tissue factor. Kits for detecting tissue factor can include anti-factor VIII or anti-factor IX antibodies, an anticoagulant agent such as a $Ca^{2+}$ chelator (e.g., citrate or oxalate), and factor VIIa. The kit further can include a calcium salt.

The invention also features a method for evaluating dosage of APC that includes obtaining a whole blood sample from a patient undergoing APC therapy and monitoring (e.g., in a device) activated clotting time of the whole blood sample in the absence of added phospholipid, wherein a significant increase in clotting time compared to a control sample from the patient before APC therapy indicates that an appropriate dosage of APC has been administered. Activated clotting time can be measured in the presence of an activator of the contact phase of coagulation.

Methods for monitoring responsiveness to APC also are featured. The methods include obtaining a whole blood sample from an individual, adding APC to the whole blood sample, and monitoring (e.g., in a device) activated clotting time of the whole blood sample in the absence of added phospholipid. A significant increase in clotting time compared to a control sample from the patient in the absence of added APC indicates that the patient is responsive to APC.

The invention also features kits for detecting factor VIIa or APC in blood. The kits include a $Ca^{2+}$ chelator, a calcium salt, and an activator of the contact phase of coagulation. The kit further can include factor VIIa or APC.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 2A is a graph of clotting time versus concentration of VIIai (solid circles) and dimeric VIIai (open circles when calculated on the basis of monomer concentration and open squares when calculated on the basis of dimer concentration). FIG. 2B is a Hill type plot of the data shown in FIG. 2A.

FIG. 4A is a comparison of wild type factor VIIai (solid circles) with monomeric VIIai(P10Q/K32E) (open triangles), dimeric VIIai(P10Q/K32E) containing over 50% dimer (open circles), and VIIai(P10Q/K32E) containing traces of dimer (open squares). FIG. 4B is a comparison of wild type VIIai (solid circles) with mutant VIIai(P10Q/K32E) (open squares) and a heterodimer of mutant VIIai(P10Q/K32E)-Xa (open triangles).

FIG. 6A represents the clotting time of patients with severe hemophilia without inhibitors at various concentrations of factor VIIa. The inset of FIG. 6A is the dose-response to factor VIIa. The clotting time at 200 nM WT-VIIa or 50 nM QE-VIIa was set at a value of 1.0 and other clotting times were expressed as a ratio. For direct comparison, the concentration of enzyme is expressed relative to the highest concentration (log [QE-VIIa]/50 or log [WT-VIIa]/200). The slope of the best fit straight line (Kaleideagraph program) for WT-VIIa was –0.13 (27 titrations, average and SD shown, O) and for QGED it was –0.20 (24 titrations, average and SD shown, ●). FIG. 6B provides the clotting times of artificial hemophilia samples, as assayed in the ACT-LR.

In FIG. 8A, patients with severe hemophilia without inhibitors are represented by solid bars, subjects 1–4 who have inhibitors to either IX or VIII and show low or moderate response to factor VIIa therapy are represented by open bars, and two individuals with antibodies to factor VIII and good to moderate response to factor VIIa therapy are represented by solid bars. In FIG. 8B, subjects A and B are presented as a separate group (solid bars) since they presented low response most often. In FIG. 8C, one female, age 30 (solid bars) showed lower response to factor VIIa than eight other subjects (open bars).

In FIG. 9A, titrations for VIIai (solid circles), VIIai-PEG-3.4 k (open squares), VIIai-PEG-20 k (solid triangles), and VIIai-PEG-40 k (open triangles) are presented. In FIG. 9B, the circulation half-life (in hr) is shown for the samples of FIG. 9A, plotted as a function of the molecular weight of the PEG attached to the protein.

FIG. 10A shows results for three animals that were administered VIIai (solid circles, open diamonds, and inverted triangles), one animal that was administered dimeric VIIai (open squares), and two animals that were administered VIIai-PEG-3.4 k (solid triangles and solid diamonds). FIG. 10B provides the turnover of randomly modified VIIai. Two lines are drawn for the first three and the last three data points. VIIai is shown for reference (solid circles).

In FIG. 15B, assays for ACT-LR (QGED-APC (solid squares) and WT-APC (open squares) and for the ACT+ (QGED-APC (solid circles) and WT-APC (open circles) are shown. The inset of FIG. 15B provides an expanded view at low APC concentration. In FIG. 15C, results of the ACT-LR assay (without phospholipids) are provided. Titration with QGED-APC (solid circles, solid diamonds, solid squares, and solid triangles, subjects 5, 6, 7, and 8, respectively) and with WT-APC (open circles, open diamonds, open squares, and open triangles, subjects 5, 6 7 and 8, respectively) are shown. The inset of FIG. 15C provides an expanded presentation of results at low APC concentration.

DETAILED DESCRIPTION

Vitamin K-dependent polypeptides are a group of proteins that utilize vitamin K in their biosynthetic pathways to carboxylate the side chains of glutamic acid residues in protein precursors. The GLA domain contains 9–13 γ-carboxyglutamic acid residues in the N-terminal region of the polypeptide, typically from amino acid 1 to about amino acid 45. Protein Z, protein S, factor X, factor II (prothrombin), factor IX, protein C, factor VII, Gas6, and bone matrix GLA protein are examples of vitamin K-dependent polypeptides that are useful in the invention. Furthermore, useful vitamin K-dependent polypeptides can be wild-type or can contain mutations. Particularly useful factor VII and protein C mutations are described in Shah et al. (1998) *Proc. Natl. Acad. Sci. USA* 95:4229–4234 and Shen et al. (1998) *J. Biol. Chem.* 273:31086–3101, respectively, in which enhancements in protein function were reported. Also see U.S. Pat. No. 6,017,882 for additional mutations. Many clotting factors, including factors VII, IX, X, and prothrombin, are zymogens, i.e., inactive proenzymes, and are converted during coagulation to active serine proteases.

Figure 1:
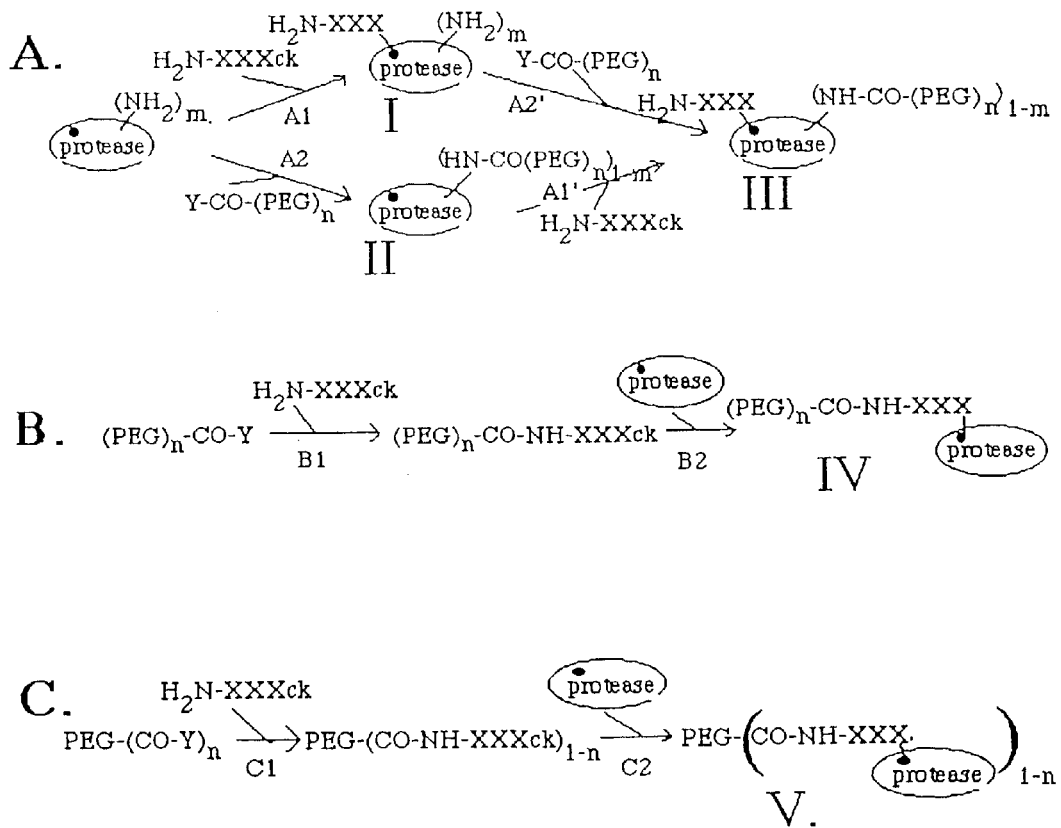
FIGS. 1A–1E are schematics of strategies for modifying vitamin K-dependent polypeptides.
Figure 1:
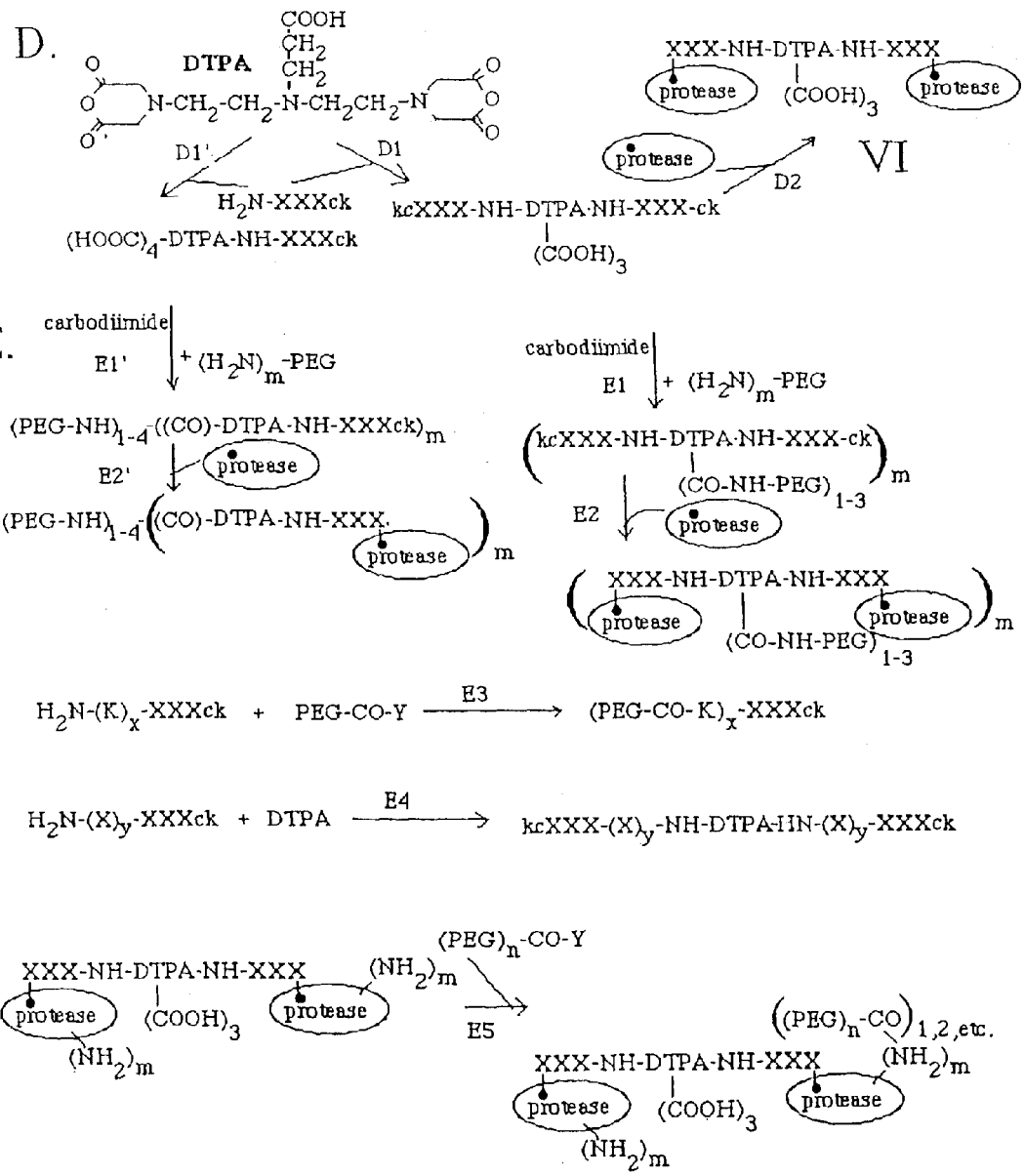

FIG. 1 provides a general description for making the derivatives of vitamin K-dependent polypeptides of the invention. The polypeptides presented in FIG. 1 are described as proteases. It should be noted, however, that many of the reactions, including reactions A2, A2' and E5, can be used with any vitamin K-dependent polypeptide.

Vitamin K-dependent Polypeptides Linked to PEG Polymers

The invention features isolated vitamin K-dependent polypeptides linked to polyethylene glycol (PEG) polymers. An "isolated polypeptide" has been separated from cellular components that naturally accompany it. Typically, the polypeptide is isolated when it is at least 60% (e.g., 70%, 80%, 90%, or 95%), by weight, free from proteins and naturally-occurring organic molecules that are naturally associated with it. As used herein, the term "polypeptide" is any chain of at least five amino acids that retains the ability to bind cofactors or membranes. Amino acids have been designated herein by standard three letter and one-letter abbreviations.

Derivatization of amino groups on the surface of proteins (m in FIG. 1A) with PEG-containing compounds can extend the circulation time of some proteins and reduce their potential antigenic properties. See, Beauchamp et al. (1983) *Anal. Biochem.* 131(1):25–33. In general, the greatest impact on circulation time has been with longer chain PEG polymers, with a molecular weight up to about 15,000. PEG modified proteins typically are low molecular weight proteins that are cleared from the circulation by pinocytosis in the kidney, such as a Fv fragment of an antibody molecule, and proteins that act on low molecular weight substrates, such as superoxide dismutase, asparaginase, and hemoglobin. Lee et al. (1999) *Bioconjugate. Chem.* 10:973–981; and Shearwater Polymers, Inc. (2000) Catalog, p. 41, Huntsville, Ala. The increase of molecular weight by addition of PEG to low molecular weight proteins is thought to enhance circulation lifetime by eliminating a specific clearance process.

PEG-derivatization of proteins also can reduce protein antigenicity. Thus, PEG derivatization can reduce or prevent antibody production to a foreign protein. Without being bound by a particular mechanism, a 'polymer cloud' of PEG may diffuse at the surface of the protein, obliterating the surface for the macromolecular recognition system of antibody production. Shearwater Polymers, Inc. (2000) Catalog, p 11. Based on this mechanism, PEG modification may hinder interaction of the modified protein with other macromolecules while allowing small molecule diffusion near the protein surface such that substrate access to the active site is virtually unchanged. Thus, activity of proteins with low molecular weight substrates, such as superoxide dismutase, is not altered, whereas binding between an antibody and antigen may be diminished with multiple PEG derivatizations. See, Lee et al. (1999) *Bioconjugate. Chem.* 10:973–981.

Based on this, factor VII and other vitamin K-dependent polypeptides such as factors IX, X, and II that interact with cofactor proteins, membrane surfaces, or both, appear to be unlikely targets for PEG modification. For example, factor VIIa must interact with tissue factor, a macromolecular cell surface receptor that includes a large area of the factor VIIa surface, and with a membrane surface. See, Banner et al. (1996) *Nature* 380:41–46. The presence of a polymer cloud over the factor VIIa surface would be expected to interfere with both of these critical interactions. In addition, the vitamin K-dependent polypeptides occur naturally in the plasma and have molecular weights that are high enough to avoid rapid removal through the kidney. As described herein, however, vitamin K-dependent polypeptides that are linked to PEG have an increased lifetime in the circulation, with little or no impact on activity.

The term "linked" is used herein to include 1) both direct, covalent links and indirect links (i.e., through an intermediate molecule) of a PEG polymer to a polypeptide; 2) covalent coupling of a PEG polymer to an intermediate molecule such as an active-site inhibition reagent; 3) covalent coupling of an active-site inhibition reagent to a protease; and 4) direct, covalent links and indirect links (i.e., through an intermediate molecule) of polypeptide monomers to each other. In some embodiments, the PEG polymer is directly and indirectly linked to the vitamin K-dependent polypeptide. Suitable PEG polymers can vary in length and valency with respect to the number of PEG chains per reactive site, n or m in FIG. 1. Typically, PEG polymers contain an activated ester (—CO—Y) and can react with protein amino groups to form a covalent linkage. Many standard leaving groups (Y) are known and are available commercially. Non-limiting examples of leaving groups include p-nitrophenol and succinimidyl propionate (SPA). In addition to activated esters, other standard approaches exist for crosslinking a reagent to amino groups on the protein surface, including, for example, aldehyde-containing PEG molecules. The aldehyde forms a Schiff's base with amino groups on the protein. The Schiff's base is selectively reduced with sodium cyanoborohydride in a well-described reaction. This chemistry is available commercially. See, Shearwater Polymers, Inc. (2000) Catalog, p. 20. Another process for attaching groups such as PEG to glycoproteins uses periodate to oxidize carbohydrates to aldehydes, followed by addition of hydrazide derivatives of the group to be attached. The hydrazide reacts with the aldehydes to produce a stable link. Hydrazide derivatives of PEG polymers are available commercially, for example, from Shearwater Polymers, Inc. and appropriate reaction conditions are described in the Shearwater Polymers, Inc. catalog (2000, p. 34). Many of the vitamin K-dependent polypeptides are glycoproteins and therefore subject to this chemistry.

PEG polymers can be directly linked to vitamin K-dependent polypeptides, including active-site modified proteases, by randomly reacting the PEG polymer with protein amino moieties. Reactions in FIG. 1A produce heterogeneous products (1 to m derivatives at random locations) as a typical polypeptide may have 20 amino groups on its surface and there is little basis for chemical selectivity. As described herein, a population of factor VIIai molecules with randomly linked PEG had circulation lifetimes that were 20 times greater than those of the wild type protein, although activity was slightly less. While products II and III in FIG. 1 are heterogeneous with respect to both the number of PEG attachments and location of the PEG on the polypeptides, these preparations have potential value to therapy. Standardization of reaction conditions can create preparations with consistent properties that may be beneficial for both pro- and anticoagulation therapy.

Reactions B1 and B2 of FIG. 1B illustrate methods used to indirectly derivatize polypeptides by attachment of the PEG polymer through the active site of the protease. In general, a PEG polymer and an active-site inhibition reagent (described below) can be covalently linked to form a PEG-modified active-site inhibition reagent before reacting with an activated vitamin K-dependent polypeptide, such as factor VIIa, IXa, Xa, or IIa. Since the active-site-directed inhibitor has a single amino group, only one product (compound IV) is generated from reaction B1. Unreacted active-site-directed reagent can be removed by dialysis or gel filtration chromatography. The PEG polymer has a high molecular weight and these simple procedures allow quantitative separation from uureacted reagent. The active ester on the PEG moiety (—CO—Y) is slowly hydrolyzed by water, and incubation for a period of time can remove excess reactive reagent. Thus, it may not be necessary to remove any excess PEG before proceeding with step B2. Once all of the activated ester is destroyed by water hydrolysis, step B2 can be initiated.

In step B2, the PEG-modified, active site-directed reagent reacts with the protease, with negligible side reactions, to produce a single entity. Excess PEG, in any form, can be removed by ion exchange chromatography on a material such as DEAE-Sephadex, which is a standard step in the purification of vitamin K-dependent polypeptides. These polypeptides bind tightly to anion exchange material at low salt (e. g. 0.1 M NaCl, pH 7.0) and are eluted by high salt (e. g. 0.5 M NaCl). As unreacted PEG polymers have little charge (the active site-directed reagent is cationic, if it is present) and do not bind to an anion exchange resin, the polymers can be removed by washing the column with low salt buffer before eluting with high salt. The reactions described in FIG. 1B can use a range of leaving groups (Y) or other strategies for derivatizing amino groups as outlined above. Purification of the final product may not be necessary as unreacted PEG polymers are biologically inert and active-site inhibition reagents may not pose adverse effects.

Circulation lifetime was determined by the size of the PEG polymer attached. One preparation had a circulation half-time that was almost 20-fold greater than that of normal VIIai. The magnitude of impact of PEG on circulation time of factor VIIai was very surprising, given that this protein is a naturally occurring plasma protein and that it is not subject to removal as a low molecular weight peptide. The PEG derivatives of blood clotting proteases described herein provide an enormous advantage for use in either procoagulant (e.g. factor VIIa or IXa) or anticoagulant (Factor VIIai, IXai, Xai or IIai) therapy. The longer circulation time not only decreases the amounts needed for anticoagulation over time, but also greatly diminishes the frequency with which the anticoagulants have to be administered by injection.

In some embodiments, PEG polymers having more than one reactive group (e.g., 2–4) per polymer can be used to modify the vitamin K-dependent polypeptide. PEG polymers with more than one reactive group are commercially available from, for example, Shearwater Polymers, Inc. PEG polymers with other combinations of reactive groups can be generated by chemical synthesis using known chemistry. The reactions in FIG. 1C utilize multivalency of reactive groups on the PEG polymer to generate multivalency with respect to active-site modified proteases. Quantitative yields in reaction C1 are difficult to achieve due to water hydrolysis of the active ester. In addition, with, e.g., four reactive groups per polymer, one can expect PEG products containing 0, 1, 2, 3, and 4 active site-directed inhibitors. Purification of each product is possible, although more complex than purification of compound IV in FIG. 1B. Since the active-site-directed inhibitor typically contains the side chain of an arginine residue, each active-site inhibition reagent that is present adds a charge and the products can be separated by ion exchange chromatography. Each peptide of the active-site inhibition reagent also can enhance affinity of the product for reverse phase chromatography on a C18 column.

Active Site Inhibition Reagents

Chloromethylketones or organic phosphohalides such as diisopropylfluorophosphate (DIFP) can be used to modify the active-site of proteases that are vitamin K-dependent polypeptides. Chloromethylketones can be single amino acids such as tosylysylchloromethylketone (TLCK) or short peptides and are commercially available. Phenylalanylprolylarginylchloromethylketone (FPRck, also known as PPACK) is available from Calbiochem, San Diego, Calif. and is described by the manufacturer as a good inhibitor of thrombin and factor VIIa, among other enzymes. Phenylalanylphenylalanylarginylchloromethylketone (FFRck, also known as PPACK II) is available from Calbiochem and is another example of a commonly available peptide. Glutamylglycylarginylchloromethylketone (EGRck) can be used with a derivative at its amino terminus, such as the fluorescent derivative, Dansyl-EGRck (DEGRck), and also is available from Calbiochem.

Reactions A1 and A1' of FIG. 1 depict reaction of a chloromethylketone derivative (ck) of an active site-directed peptide or amino acid ($H_2N$-XXX) with the active site of a blood clotting protease (e.g., Factor VIIa, IXa, Xa, thrombin or factor IIa) to create an inactive enzyme (VIIai, Xai, IXai, IIai).

Oligomers of Vitamin K-dependent Polypeptides

The invention also features anticoagulant agents that include oligomers of vitamin K-dependent polypeptides. In general, the anticoagulant agent includes at least two polypeptide monomers that are covalently cross-linked. At least one of the polypeptide monomers is a vitamin K-dependent polypeptide, while the second polypeptide monomer can be the same or a different vitamin K-dependent polypeptide, a protease, (e.g., trypsin), or a polypeptide that contains a membrane-binding site. Annexin polypeptides are non-limiting examples of polypeptides that contain a membrane binding site. FIG. 1D provides reactions for producing a homodimer of active site-modified blood clotting proteases. Heterodimers can be produced in a similar manner. Homodimer refers to a dimer containing two identical polypeptides, while heterodimer refers to a dimer containing two different polypeptides. Typically, a bifunctional reagent is reacted with an active-site inhibition reagent (reaction D1 and D1'), and the resulting bifunctional active-site inhibition reagent, containing two active-site inhibitors, is isolated. The monovalant product also can be isolated and may be useful in some embodiments. Diethylenetriaminepentacetic acid anhydride (DTPA) is an example of bifunctional reagent that can be used. Many other bifunctional reagents that react with amines are available commercially. For example, the Pierce Chemical Co. (Rockford, Ill.) has 49 bifunctional reagents available that react with amines.

HPLC chromatography can be used to separate univalent products from divalent products. The bifunctional active-site inhibition reagent can be used to create various homodimers and heterodimers of blood clotting proteases, such as compound VI of FIG. 1D. Addition of phospholipid vesicles to the reaction can increase dimer yield. In some cases, heterodimers may be more effective in vivo due to simultaneous inhibition of several steps of coagulation. For example, a factor Xai-factor IXai diner can inhibit factors VIIIa and Va at the same time, while a VIIai-Xai dimer can inhibit tissue factor and factor Va at the same time. Homo- and heterodimers can be purified by standard methods, including, for example, gel filtration chromatography.

As described herein, dimers of wild type factor VIIai enhanced protein-cofactor-membrane binding by about 16-fold, which is much less than the theoretical increase of $10^6$ to $10^{11}$-fold. The heterodimer of VIIa and factor Xa produced a 25-fold increase in competitive binding to tissue factor-membrane, much less than the theoretical level of about $10^7$-fold. Factor Xa has a Kd for membrane association of about $10^{-7}$. See, McDonald et al. (1997) *Biochemistry* 36:5120–5127. Dimerization of a mutant of factor VIIa (P10Q/K32E), which has higher affinity for the membrane than wild type factor VIIa, did not result in detectable improvement of binding affinity. See, Shah et al., supra, for a description of the mutant. This indicates that minor changes in the membrane-binding site altered the ability to participate in simultaneous binding. The heterodimer of mutant VIIa and factor Xa actually had reduced affinity for tissue factor-membrane than did monomeric mutant VIIai. While a 16–35-fold improvement in affinity can have a large impact on therapeutic value of a drug, this range is a very small part of the total free energy of the multiple binding events.

Dimerized, Active-site Modified, PEG-linked Vitamin K-dependent Polypeptides

As described above, PEG polymers can be introduced to random surface amine groups or to the active site of a protease to enhance its circulation time and active site-modified enzymes can be dimerized to enhance function. Such protein modification strategies can be combined to provide dimeric, active site-modified proteases that are linked to PEG polymers, resulting in polypeptides with up to several hundred-fold enhancement of function over wild type, monomeric, active site-modified proteases. Well-known and established chemistries can be used to produce such modified polypeptides, as illustrated in FIG. 1E. Reactions E1, E2, E1' and E2' are continuations of the DTPA dimerization shown in FIG. 1D and combine dimer formation and introduction of PEG into the same molecule. Both DTPA derivatives of the active site-directed inhibitor contain carboxyl groups but no amino groups. The DPTA derivatives can be crosslinked to appropriate amines by well-known reactions such as that of carbodiimide, a reagent that is commonly used for amide and peptide bond synthesis. Both the monomeric and dimeric inhibitor products can be modified by these reactions.

When univalent PEG is used as the source of amino groups (m=1 in FIG. 1E), a range of products can be produced that differ in the number of PEG polymers attached to the active-site-directed reagent. For example, a divalent active site-directed intermediate can produce a modified polypeptide that has the longer circulation time provided by PEG and the higher activity of dimeric VIIai. An intermediate with a single active-site-directed inhibition reagent can produce an inhibitor with the advantage of multiple PEG polymers, giving enhanced circulation lifetime.

If multivalent PEG (m>1, FIG. 1E) is used as the source of amino groups, complex products can be produced such as an oligomer of monomers (reaction E2') or an oligomer of dimers (reaction E2). Products generated by reactions E1 and E2 may be heterogeneous due to difficulty in obtaining quantitative or strictly controlled reaction with carbodiimide. Nevertheless, heterogeneity does not prevent formation of useful products. Since mulivalency occurs on both the amino group and the carboxyl group, some products may be extremely large.

Reaction E3 outlines a strategy for introducing multiple PEG polymers to the active site of a vitamin K-dependent protease. This can be accomplished, for example, by using an active-site inhibition reagent that includes additional amino groups. The example shown in reaction E3 is a short polylysine chain ($K_y$). The PEG-linked product can be coupled to factor VIIa by reaction B2.

Crosslinkers with longer spacer arms can be produced by reaction E4, using the reactions described in FIG. 1D, but with different active-site inhibition reagents. Use of linker arms of different length is well-established in crosslinking technology. Several crosslinking agents with different lengths (e.g. linker arms of 2 to >1000 atoms) are available from commercial sources such as the Pierce Chemical Co. and the Sigma Chemical Co. For example, elongated, bifunctional active-site inhibition reagents with more than three amino acids can be produced and the remaining reactions carried out as in FIG. 1B. The advantage of reaction E4 may be the ability to utilize a wider range of proteins. Using a longer linker arm, generated by the simple modification shown in reaction E4 (or numerous other strategies), may result in dimers with enhanced activity.

Reaction E5 shows another benefit of dimeric proteins. That is, random derivatization of a dimer with one PEG polymer leaves one polypeptide monomer without modification. That is, addition of one PEG polymer to a dimeric polypeptide leaves one polypeptide monomer completely underivatized and free to bind to its receptor or cofactor protein. In fact, by random attachment, fifty percent of a dimer population that has an average of two PEG polymers attached still will have one polypeptide monomer that is underivatized. The use of dimeric proteins may allow very high order PEG substitution with retention of substantial activity, as randomly derivatized monomeric factor VIIai retained function to the level of at least one PEG per molecule.

Assay for Factor VIIa or Activated Protein C (APC) Therapy

The invention also provides an assay for factor VIIa or APC therapy that can detect individual variation in sensitivity to VIIa and APC, and help target dosage levels for individual patients. There is no assay for monitoring APC therapy and as a result, there is no basis for adjusting the dosage administered to a patient. A major challenge for factor VIIa therapy is the absence of an assay that detects individual response to factor VIIa. Consequently, a single dose is recommended for all individuals. Some individuals appear to have low response to factor VIIa. In the absence of an assay, low sensitivity is detected by failure to treat and several days may be consumed before other therapies are used. Assays for hemophilia A and B, its severity and the level of correction by infusion of VIII or IX clotting factors are normally conducted with a plasma clotting assay known as the APTT time. This assay depends on activation of the intrinsic blood clotting cascade (factor XII) by agents such as Kaolin or Ellagic acid. Upon addition of calcium, XIIa activates XI, which activates IX, and coagulation occurs. This assay therefore depends on factors IX and VIII levels in the plasma and is sensitive to both hemophilia A and B. A problem for factor VIIa therapy is that its mechanism of action may differ from the normal cascade. That is, factor VIIa can bind to phospholipid surfaces and activate factor X directly, without use of tissue factor, factor IX, or factor VIII. See, Monroe et al. (1997) *Brit. J. Haemat.* 99:542–547. hi the absence of tissue factor, factor VIIa is a relatively poor enzyme. In addition, factor VIIa has relatively low affinity for a membrane.

Assays that depend on externally added phospholipid do not represent the true coagulant status of patients undergoing factor VIIa or APC therapy, as phospholipid content influences the outcome of the assay. For example, at high phospholipid concentration, wild type factor VIIa and a mutant factor VIIa protein (P10Q/K32E) have nearly identical activities, while at low phospholipid concentration, an 8-fold difference is observed between the wild type and mutant protein.

As described herein, clotting time can be more accurately monitored by using an assay containing biological membranes rather than phospholipids. Since individuals vary with respect to their cellular activity, the assay should use the cells of the patient undergoing therapy, at the time at which therapy is administered. Thus, the invention features a method for evaluating dosage of factor VIIa, including PEG-modified factor VIIa, or APC, as well as a method for monitoring responsiveness to factor VIIa or APC therapy. To evaluate dosage of VIIa or APC, biological samples such as whole blood are obtained from a patient before and after factor VIIa or APC administration and activated clotting time is monitored. Typically, a device such as the HEMOCHRON® Jr. from International Technidyne or a similar instrument is used to facilitate the measurement. Such devices contain optical detectors that monitor coagulation time by detecting the speed at which the blood moves between two of the optical detectors. Other devices use resistance to mechanical agitation such as stirring or flow under pressure to detect clotting time. The activated clotting time (ACT) assay and specific instrumentation such as the HEMOCHRON® Jr. microcoagulation apparatus typically are devoted to monitoring anticoagulation therapy during surgery or other procedures. The results herein, however, indicate that the ACT can provide the necessary conditions required to monitor procoagulation response in hemophilia patients receiving factor VIIa as well as other types of anticoagulation and anticoagulation status in patients in need of anticoagulation.

To assess responsiveness of the patient to be treated with factor VIIa, the biological sample from the patient is placed in a cuvette or similar container that is lacking added phospholipid. Factor VIIa is added to the sample and clotting time is measured, e.g., by placing the cuvette in the device. In some embodiments, the cuvette or similar contains also contains an activator of the contact phase of coagulation such as Celite, kaolin, or ellagic acid. The clotting times of samples before and after factor VIIa therapy are compared to determine if clotting time has significantly decreased. If a sufficient decrease in clotting time is observed after factor VIIa administration, a sufficient dosage of factor VIIa has been administered. A sufficient decrease in clotting time refers to the restoration of hemostasis in the patient. If clotting time has not sufficiently improved, factor VIIa dosage can be modified appropriately. Similarly, patient responsiveness to factor VIIa can be evaluated by monitoring clotting time of a whole blood sample in the presence of added factor VIIa and in the absence of added phospholipid. Clotting time is compared to that of a corresponding control sample from the patient in the absence of added factor VIIa.

Figure 6:
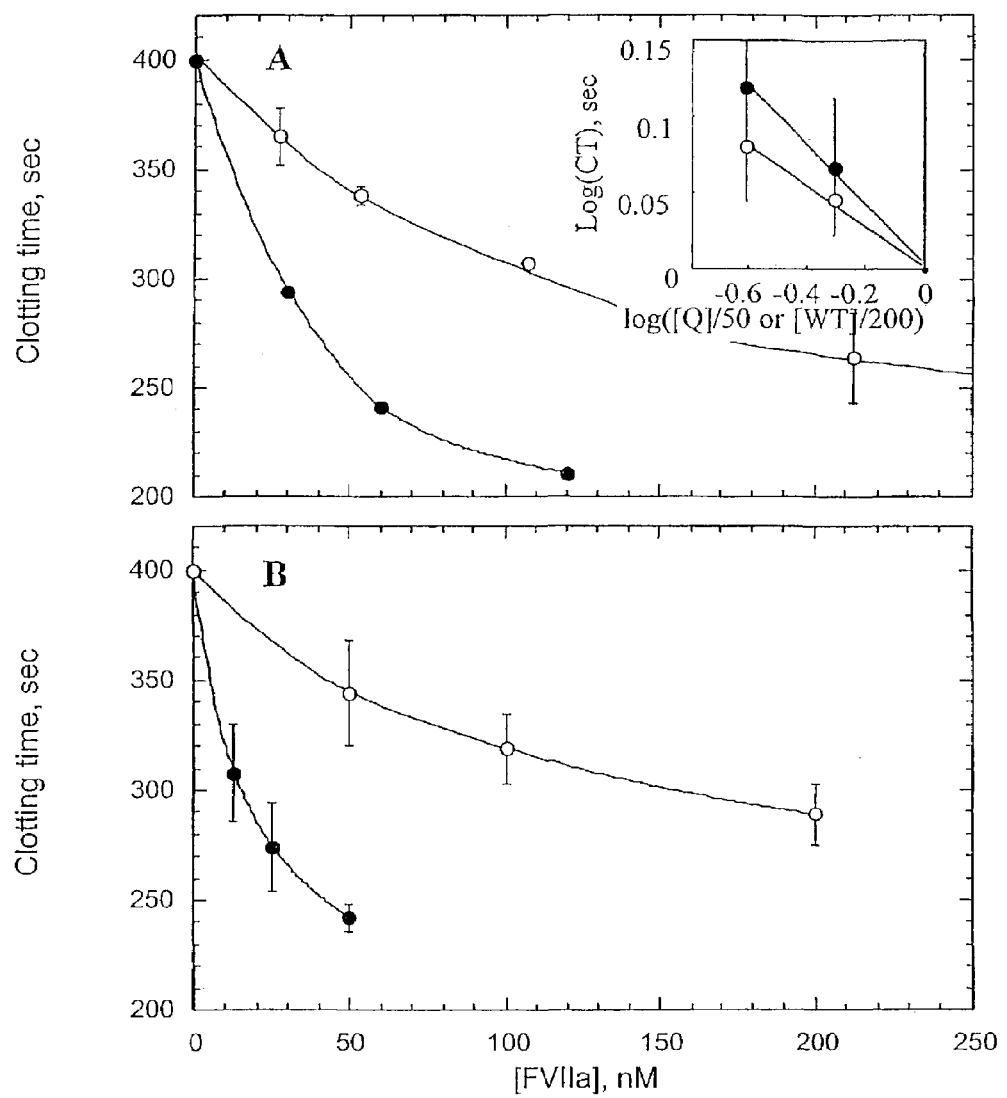
FIGS. 6A and 6B are graphs depicting the response to WT-VIIa and QE-VIIa.

Alternatively, titration curves, similar to those shown in FIG. 6, may be constructed before administration of VIIa to an individual. Individual response to factor VIIa is relatively constant over time. Therefore, prospective candidates for factor VIIa therapy can have a titration curve performed ahead of time and used to design therapy when needed.

For evaluating dosage of APC or other anticoagulant, a biological sample such as a whole blood sample is obtained from the patient undergoing APC therapy, and added to a cuvette or similar container that contains an activator of the contact phase of coagulation in the absence of added phospholipid. Clotting time of the sample after APC therapy is compared to the clotting time of the sample before therapy. A significant increase (i.e., statistically significant increase measured by a suitable statistical test) in clotting time compared to the control sample indicates that an appropriate dosage of APC has been administered. Responsiveness to APC can be assessed by monitoring activated clotting time of a whole blood sample of a patient in the absence of added phospholipid and in the presence of added APC. A significant increase in clotting time relative to a control sample in the absence of added APC indicates that the patient is responsive to APC.

As described herein, when APC is assayed by the traditional plasma coagulation assay, no limits to the inhibition were observed. In contrast, when the assay of the invention was used, clotting time reached a plateau with maximum inhibition at 87% of total activity. APC containing mutations at positions 10, 11, 32, and 33 (H10Q/S11G/Q32E/N33D, QGED) had about 20-fold higher function than WT-APC. At high doses of QGED-APC, no plateau in clotting time was reached. Thus, WT-APC may have advantages over standard anticoagulants, which have no limit in inhibiting clotting and may cause adverse side effects. Mutant APC may retain advantages over WT-APC at low dose, but provide more aggressive anticoagulation at high doses.

The assays of the invention provided excellent reproducibility. Unfortunately, its short clotting time and the stimulus-dependent dose-response relationship for APC made it unable to detect WT-APC at the levels used in therapy of severe sepsis. On the other hand, ACT-LR appeared to detect individual behavior. It may be possible, therefore, to extrapolate properties observed in the ACT-LR at high APC concentrations to properties at low concentration. The ACT-LR could be used to detect an individual's overall responsiveness to APC at high concentrations, which can be extrapolated to determine therapy at low APC concentrations. Use of QGED-APC for the in vitro test would enhance the precision of the test since changes in clotting time were larger. If used to monitor anticoagulation therapy, the time needed to conduct an assay favors the ACT (about 3 min) over plasma assays (about 1 hr). Low levels of APC also can be detected with a low coagulation stimulus and corresponding long clotting time. For example, clotting time can be assessed in a plastic tube instead of glass. Alternatively, clotting time can be assessed in the Clot Signature Apparatus (CSA®). Such an assay can monitor therapy by detecting how well the anticoagulant increases coagulation time back to the normal time. For example, diseases with elevated coagulation states may give a clotting time substantially less than 11.5 minutes. In vivo therapy would be detected by return of the patient's blood to the 11.5 minute clotting time.

The assay of the invention also provides the ability to detect genetic disorders such as APC resistance or protein S deficiency. While various plasma assays for this trait are available, they require time-consuming steps such as plasma preparation. Again, evaluation in an ACT-LR test would be advantageous when time is critical.

Acute and Chronic Phases of Coagulation

The invention also provides a method for managing anticoagulant therapy in a patient. The method includes administering an acute phase anticoagulant to a patient during acute coagulation and administering a factor VIIai polypeptide to the patient during chronic coagulation. "Chronic" anticoagulation refers to equilibrium conditions and can occur when factor VIIa and VIIai are incubated with tissue factor for a time sufficient to reach equilibrium before coagulation is initiated. The assays of FIGS. 2–4 are examples of assays performed under chronic anticoagulation conditions. In contrast, "acute" anticoagulation refers to all components related to coagulation and anticoagulation being initiated simultaneously. The assay described in FIG. 5, which required Xai to inhibit coagulation, exemplifies acute coagulation. That is, the receptor for Xai, factor Va, is not present until coagulation begins.

Most anticoagulants target materials that are not present until coagulation has begun and therefore act in an 'acute' manner. For example, heparin stimulates antithrombin III inhibition of thrombin; thrombin is not present until coagulation has been initiated. A large number of active site inhibitors of clotting enzymes such as thrombin, Xa, IXa and VIIa all act on a coagulation process that has been initiated. The receptors for factors IXai and Xai (factors VIIIa and Va, respectively) are not present until coagulation has begun. Thus, factor VIIai, as well as antibodies having specific binding affinity for tissue factor, may provide a unique form of anticoagulation that is referred to herein as 'chronic' anticoagulation.

A chronic anticoagulation state can be reached when tissue factor is exposed to the circulation for a prolonged period of time, initiating continual, but very limited, coagulation events. This condition may exist for some time before the tissue factor is removed from the circulation, allowing factor VIIai to reach binding equilibrium and creating 'chronic' anticoagulation. Acute coagulation occurs when the endothelium is damaged, e.g., during angioplasty, surgery, catherization, or other invasive procedure. After this initial phase, however, chronic coagulation conditions may exist when tissue factor is present for a prolonged period of time.

Administration of factor VIIai, and especially factor VIIai with high affinity for tissue factor-membrane, such as dimeric VIIai and mutants with high membrane affinity, during the chronic phase is an effective method of anticoagulation treatment. Although VIIai can prevent acute coagulation, higher dosages are needed. As described herein, wild type VIIai was about 25-fold more effective under chronic coagulation than under acute coagulation conditions. The Q10E32 VIIai mutant (also referred to as QE-VIIai) was, identical to WT-VIIai during acute anticoagulation, but 25-fold more effective than WT-VIIai in chronic situations. The overall difference between chronic and acute for Q10E32ai was more than 500-fold. Antibodies having specific binding affinity for tissue factor also can be used as chronic anticoagulants. Thus, for many situations such as catheterization, angioplasty, and surgery, effective anticoagulation therapy can include use of a combination of anticoagulants, a highly effective inhibitor of acute coagulation (e.g., heparin) during the procedure that generates tissue injury (such as endothelial cell damage during angioplasty) and a chronic anticoagulant such as VIIai, anti-TF antibodies, or tissue factor pathway inhibitor (TFPI), when new injury is minimal. Treatment with VIIai might require several days to provide continual protection until healing is complete and tissue factor is entirely removed from the circulation. Using PEG-derivatized and/or dimerized proteins (e.g., VIIai, Xai, IXai) as chronic anticoagulants during anticoagulation therapy can reduce dosages and reduce the frequency of administration. Factor VIIai may be a safe and effective anticoagulant because it does not inhibit coagulation due to new injury but blocks longer-term TF exposure.

Methods for Detecting Tissue Factor (TF) in Blood

TF is involved in the first step of coagulation, where it combines with factor VIIa to form the initial enzyme complex that starts the blood clotting cascade. TF typically is found in tissue and is not thought to be a component of blood under normal conditions. TF is thought to be present during pathologic conditions that lead to thrombosis. As described herein, the presence or absence of TF in the blood can be detected in an assay in which factor VIII or factor IX are neutralized in a blood sample (e.g., an anticoagulated whole blood sample) and clotting time is assessed in the factor VIII or factor IX neutralized sample in the presence or absence of anti-TF antibodies. A comparison of the clotting times allows the amount of factor VIIa-induced coagulation that is sensitive to TF to be determined. Such information can be used to screen or diagnose coagulation problems as well as other disorders that may result in altered TF expression in the circulation, e.g., arteriosclerosis or cancer.

Production of Modified Vitamin K-dependent Polypeptides

Isolated vitamin K-dependent polypeptides are commercially available from, for example, Novo Nordisk (Princeton, N.J.). Vitamin K-dependent polypeptides can be produced in transgenic animals or by cell culture. Preferably, the transgenic animal or eukaryotic host can carboxylate the glutamic acid residues of the vitamin K-dependent polypeptide. To produce vitamin K-dependent polypeptides by cell culture, a nucleic acid encoding the polypeptide is ligated into a nucleic acid construct such as an expression vector, and eukaryotic host cells are transformed with the expression vector. In general, nucleic acid constructs include a regulatory sequence operably linked to a nucleic acid sequence encoding a vitamin K-dependent polypeptide. Regulatory sequences do not typically encode a gene product, but instead affect the expression of the nucleic acid sequence. As used herein, "operably linked" refers to connection of the regulatory sequences to the nucleic acid sequence in such a way as to permit expression of the nucleic acid sequence. Regulatory elements can include, for example, promoter sequences, enhancer sequences, response elements, or inducible elements.

In eukaryotic host cells, a number of viral-based expression systems can be utilized to express vitamin K-dependent polypeptides. A nucleic acid encoding vitamin K-dependent polypeptide can be cloned into, for example, a baculoviral vector such as pBlueBac (Invitrogen, San Diego, Calif.) and then used to co-transfect insect cells such as *Spodoptera frugiperda* (Sf9) cells with wild-type DNA from *Autographa californica* multiply enveloped nuclear polyhedrosis virus (AcMNPV). Recombinant viruses producing the modified vitamin K-dependent polypeptides can be identified by standard methodology. Alternatively, a nucleic acid encoding a vitamin K-dependent polypeptide can be introduced into a SV40, retroviral, or vaccinia based viral vector and used to infect suitable host cells.

Mammalian cell lines that stably express vitamin K-dependent polypeptides can be produced by using expression vectors with the appropriate control elements and a selectable marker. For example, the eukaryotic expression vector pCDNA.3.1+ (Invitrogen, San Diego, Calif.) is suitable for expression of modified vitamin K-dependent polypeptides in, for example, COS cells, HEK293 cells, or baby hamster kidney cells. Following introduction of the expression vector by electroporation, DEAE dextran-, calcium phosphate-, liposome-mediated transfection, or other suitable method, stable cell lines can be selected. Alternatively, transiently transfected cell lines are used to produce vitamin K-dependent polypeptides. Vitamin K-dependent polypeptides also can be transcribed and translated in vitro using wheat germ extract or rabbit reticulocyte lysate.

Vitamin K-dependent polypeptides can be purified from conditioned cell medium by applying the medium to an immunoaffinity column. For example, an antibody having specific binding affinity for Factor VII can be used to purify modified Factor VII. Alternatively, concanavalin A (Con A) chromatography and anion-exchange chromatography (e.g., DEAE) can be used in conjunction with affinity chromatography to purify factor VII. Calcium dependent or independent monoclonal antibodies that have specific binding affinity for factor VII can be used in the purification of Factor VII.

Vitamin K-dependent polypeptides such as protein C can be purified by anion-exchange chromatography, followed by immunoaffinity chromatography using an antibody having specific binding affinity for protein C.

Vitamin K-dependent polypeptides also can be chemically synthesized using standard techniques. See, Muir, T. W. and Kent, S. B., Curr. Opin. Biotechnol., 1993, 4(4): 420–427, for a review of protein synthesis techniques.

Pharmaceutical Compositions

The invention also features pharmaceutical compositions including a pharmaceutically acceptable carrier and an isolated vitamin K-dependent polypeptide linked to a PEG polymer or an anticoagulant agent that includes at least two polypeptide monomers (described above). The pharmaceutical composition also can include an acute anticoagulant and an active-site inhibited factor VIIa polypeptide. The modified vitamin K-dependent polypeptide (e.g., PEG-linked and/or dimerized) is present in an amount effective to alter clot formation in a mammal. Useful vitamin K-dependent polypeptides of the pharmaceutical compositions can include, without limitation, PEG-linked APC, factor VIIai, factor IXai, factor Xai, or factor IIai, as discussed above. Pharmaceutical compositions also can include an additional anticoagulant agent such as aspirin, warfarin, or heparin.

The concentration of a modified vitamin K-dependent polypeptide effective to alter clot formation in a mammal may vary, depending on a number of factors, including the preferred dosage of the compound to be administered, the chemical characteristics of the compounds employed, the formulation of the compound excipients and the route of administration. The optimal dosage of a pharmaceutical composition to be administered may also depend on such variables as the overall health status of the particular patient and the relative biological efficacy of the compound selected. These pharmaceutical compositions may be used to regulate coagulation in vivo. For example, the compositions may be used generally for the treatment of thrombosis.

Vitamin K-dependent polypeptides that are linked to a PEG polymer or anticoagulant agents described above may be formulated into pharmaceutical compositions by admixture with pharmaceutically acceptable non-toxic excipients or carriers. Such compounds and compositions may be prepared for parenteral administration, particularly in the form of liquid solutions or suspensions in aqueous physiological buffer solutions; for oral administration, particularly in the form of tablets or capsules; or for intranasal administration, particularly in the form of powders, nasal drops, or aerosols. Compositions for other routes of administration may be prepared as desired using standard methods.

Formulations for parenteral administration may contain as common excipients sterile water or saline, polyalkylene glycols such as polyethylene glycol, oils of vegetable origin, hydrogenated naphthalenes, and the like. In particular, biocompatible, biodegradable lactide polymer, lactide/glycolide copolymer, or polyoxethylene-polyoxypropylene copolymers are examples of excipients for controlling the release of a compound of the invention in vivo. Other suitable parenteral delivery systems include ethylene-vinyl acetate copolymer particles, osmotic pumps, implantable infusion systems, and liposomes. Formulations for inhalation administration may contain excipients such as lactose, if desired. Inhalation formulations may be aqueous solutions containing, for example, polyoxyethylene-9-lauryl ether, glycocholate and deoxycholate, or they may be oily solutions for administration in the form of nasal drops. If desired, the compounds can be formulated as gels to be applied intranasally. Formulations for parenteral administration may also include glycocholate for buccal administration.

Articles of Manufacture

Reagents for the assays for monitoring factor VIIa or APC therapy, evaluating patient responsiveness to factor VIIa or APC, or for detecting tissue factor described herein can be combined with packaging material and sold as articles of manufacture (e.g., kits). Components and methods for producing articles of manufacture are well known. Kits for detecting tissue factor can include, for example, antibodies having specific binding affinity for factor VIII or factor IX, an anticoagulant, and factor VIIa. The anticoagulant can be a $Ca^{2+}$ chelator such as citrate or oxalate. Such a kit further may include a calcium salt. Kits for detecting factor VIIa or APC can include a $Ca^{2+}$ chelator such as citrate or oxalate, a calcium salt, and an activator of the contact phase of coagulation. Factor VIIa and APC also can be included in kits for detecting factor VIIa and APC, respectively. In addition, kits of the invention further can contain buffers or tubes (e.g., plastic tubes), cuvettes, or other container for performing assays. A $Ca^{2+}$ chelator can be included in the tubes, cuvettes, or other contains so that the containers are prepared for receipt of the blood sample. Instructions describing how to perform the assays can be included in such kits.

The invention will be further described in the following examples, which do not limit the scope of the invention described in the claims.

EXAMPLES

In all examples shown below, the proteins used are highly purified. Wild type VIIa or factor VIIa refer to a recombinant protein sold by NOVO Nordisk Company (Princeton, N.J.).

Example 1

Synthesis of PEG-linked, Active Site-directed Inhibitor of Factor VIIa and Other Proteases The chloromethylketone-derivatized peptides FFR and FPR (FFRck and FPRck, respectively, available from Calibochem or Bachem), were linked to PEG polymers. Commercially assailable PEG polymers were used that contained reactive groups able to derivatize free amino groups. One PEG polymer contained an activated ester based on a para-nitrophenol leaving group (polyoxyethylene bis para-nitrophenyl carbonate, PEG-NPC) and was obtained from Sigma Chemical Company (St. Louis, Mo., catalog number P9299). The average molecular weight of the PEG polymer was 3000±300. Other PEG polymers that were used contained a succinimidyl propionate (SPA) leaving group, one with a single chain of PEG having a molecular weight of 20,000 (catalog number 2M4M0P01 from Shearwater Polymers, Inc.), one having two chains of PEG, each with a molecular weight of 20,000 (product number 2Z3X0T01 from Shearwater Polymers, Inc.), and another having a molecular weight of 3400 (product number 4M4M0F02, Shearwater Polymers, Inc.).

Excess FFRck or FPRck (0.05 M) was mixed with PEG-3000 (0.02M) and allowed to react at room temperature at pH 8.5 for 14 hours. The product, PEG (3000)-FFRck, contained a PEG polymer covalently linked to the amino terminus of FFRck. The product was separated from unreacted peptide by gel filtration on Sephadex G-25. Reactions of $H_2N$-FPRck with PEG-20,000 and PEG(20,000)$_2$ were conducted in a similar manner but were complete within 2 hours at room temperature. Unreacted $H_2N$-FPRck was removed by dialysis of the reaction mixture against buffer for 48 hours. For both reactions, the amount of product formed was quantitated by UV absorbance of phenylalanine in the active site-directed inhibitor, using an extinction coefficient of 260 $M^{-1}$ $cm^{-1}$.

The PEG-3000 derivative (approximately 2:1 mol/mol of protein) was mixed with factor VIIa and allowed to react for 2 hr at room temperature in buffer (pH 7.5) containing 5 mM calcium. For quantitative reaction with the larger PEG derivatives, reactions were allowed to proceed for 15 hours at room temperature. Reaction with factor VIIa was monitored by loss of factor VIIa amidase activity toward the chromogenic substrate S-2288 (0.2 mM, Kabi) in a solution containing 100 nM soluble tissue factor (Dr. Walter Kisiel) and 5 mM calcium. When all factor VIIa activity was gone, the product was analyzed by standard SDS-PAGE methods.

Factor VIIa has a molecular weight of 50,000 and the expected molecular weight of the product was 53,000. On SDS-PAGE, however, PEG (3000)-VIIa migrated at a molecular weight greater than that of the bovine serum albumin standard (MW=67,000). SDS does not bind to the PEG portion of the molecule, which may account for the unusual migration in the gel. In addition, PEG is a very extended, unordered structure and may appear very large. The PEG (20,000)-VIIai migrated at an apparent molecular weight of 100,000, rather than at the expected molecular weight of 70,000. Again, the higher apparent molecular weight may stem from the PEG portion of the molecule.

When assayed by competition with factor VIIa (see below), the PEG-VIIai preparations had activity only slightly below that of the VIIai without PEG. Some reduction in activity was detected that correlated with the molecular weight of the PEG polymer. The PEG(3400)-Q10E32ai mutant had activity indistinguishable from the Q10E32ai protein. The PEG(20,000)-Q10E32ai and PEG(20,000)$_2$-Q10E32ai had activities approximately 40% that of the Q10E32ai molecule. This change may arise from a lower diffusion coefficient of the derivatized molecule. As the PEG polymer is very extended, it increases molecular volume much more than molecular weight. Diffusion coefficients, however, are proportional to molecular radius, while molecular volume is proportional to the particle radius cubed. Thus, a 2.5-fold decrease in diffusion can represent as much as a 6-fold increase in molecular volume. This decrease in function is small relative to the beneficial effect of PEG on circulation lifetime of these proteins.

Example 2

Synthesis of Bivalent Inhibitor from DTPA Anhydride:

Active-site inhibitors were covalently linked to diethylenetriaminepentaacetic acid anhydride (DPTA), a bifunctional anhydride (Sigma Chemical Co., St. Louis, Mo.), to produce a bifunctional product. DPTA was slowly added as a solid to a solution of FFRck (0.04 M) at a pH 8.5 and reaction products were separated by HPLC. Samples were applied to a C18 column (Vydac) in reaction buffer. The column was washed with 0.1% trifluoroacetic acetic acid (TFA), and a gradient of 20–24% Acetonitrile in 0.1% TFA was applied from 4 to 24 minutes. A peak eluting at 20.8 minutes was identified by mass spectrometry as the desired bifunctional product DPTA-DiFFRck (molecular ion at 1358.2). A reaction product that eluted at 13.73 minutes was identified as the monovalent DTPA-FFRck product and had a monoisotopic mass of 876.

Example 3

Production of Vitamin K-dependent Polypeptide Homodimers:

Factors VIIai-VIIai, VIIai(Q10E32)-VIIai(Q10E32) and Xai-Xai homodimers were generated using DPTA-DiFFRck. One equivalent of DPTA-DiFFRck was added to each of the protein solutions (0.15±0.05 mg/mL) and allowed to react at room temperature and a pH of 7.5 in the presence of 5 mM calcium. Formation of product was monitored by loss of amidase activity as described in Example 1. In some cases, phospholipid vesicles (1.5:1.0 w/w vesicles/protein) were added to increase the rate of product formation. Binding of proteases to the membrane is thought to place their active sites in close proximity and enhance production of the dimer. When all enzyme activity was inhibited, the product was isolated by gel filtration chromatography on a column of either Sephadex G-100 or Sephacryl S-200HR. The dimer eluted before monomeric protein and was identified by SDS-PAGE. The apparent molecular weights were appropriate for the dimeric proteins.

Dimeric, PEG modified factor VIIai containing the mutations P10Q/K32E was produced using a PEG-derivatized, bifunctional active-site inhibition reagent. A bifunctional SPA derivative of PEG (product number 4M4M0F02, Shearwater Polymers, Inc.) having a PEG molecular weight of 3400 (5.7 mg) was added slowly, as a solid, to a solution of FPRck (8.3 mg in 0.125 mL of 0.1 M HEPES buffer, pH 8.5). The reaction proceeded for 15 hr at room temperature and the product was separated from unreacted FPRck by chromatography on Sephadex G-25.

The PEG-derivatized, active-site inhibition reagent eluted at the exclusion volume of the G-25 column and was quantitated by absorbance of phenylalanine at 260 nm, as above. Equimolar quantities of PEG-derivatized active site inhibition reagent and mutant factor VIIa (44 pmol in 0.115 mL of 0.05 M Tris buffer pH 7.5 containing 0.1 M NaCl and 5 mM CaCl$_2$) were mixed and allowed to react at room temperature for 4 hours. After 1.5 hr, 4 µg of phospholipid vesicles (phosphatidylcholine/phosphatidylethanolamine/phosphatidylserine, 40/40/20) were added. Electrophoresis of the product showed approximately 30% yield of dimer with the rest of the protein migrating at the same position as PEG(3000)-VIIai. Analysis of activity of this mixed product by the competition assay described below showed that its inhibitor activity, on a weight basis, was equal to that of the monomeric VIIai mutant without PEG attached.

Example 4

Heterodimers of VIIai-Xai and Wild Type Vai-VIIai (QlOE32)

Factor VIIa was reacted with a 6-fold molar excess of bifunctional DPTA-DiFFRck reagent to prevent formation of a dimer of wild type VIIa. The product, VIIai-FFR-DPTA-FFRck, was separated from excess reagent by gel filtration on Sephadex G-25. The product then was reacted with factor Xa (bovine protein) to form VIIai-FFR-DPTA-FFR-Xa, also referred to as VIIai-Xai. Product was separated from monomeric proteins by gel filtration on Sephadex G-100. The molecular weight of the VIIai-Xai heterodimer was appropriate for this species (MWs of factor Xa and factor VIIa are 46,000 and 50,000, respectively).

Heterodimers of VIIai-VIIai(P10Q/K32E) were formed without isolation of intermediates. An equimolar quantity of DPTA-DiFFRck was mixed with a solution of factor VIIa (0.1 mg/mL) at room temperature and pH 7.5. Minimal amounts of dimeric VIIai, as estimated by SDS PAGE, were formed at these low protein concentrations. Equimolar amounts of mutant factor VIIa(P10QK32E) and phospholipid vesicles (1.5 g lipid/g protein) were added to the reaction mixture. Factor VIIa and VIIa(Q10E32) both can bind to the vesicles, facilitating formation of crosslinks. Analysis by SDS-PAGE indicated that the yield of dimer was over 50%. High yields of dimeric VIIai (>50%) only were obtained in reactions that contained phospholipid vesicles. Dimers were separated from monomeric proteins by gel filtration on Sephadex G-100. Heterodimers of mutant VIIa(P10Q/K32E) with factor Xa were formed with similar reaction conditions, adding Xa in the second step.

Homodimers of mutant factor VIIa(P10Q/K32E) were made directly by addition of bifunctional DTPA-DiFFRck to a mixture of protein and phospholipid vesicles. Since this mutant binds tightly to the membrane, it was easily dimerized by the bifunctional active-site inhibition reagent. Homodimers of factor Xa were made by the same methods.

Example 5

Superior Activity of Dimeric Enzymes:

A competition assay was used to assess the affinity of various proteins for membrane-associated tissue factor. Both VIIa and active-site modified factor VIIa bind to tissue factor. Factor VIIai prevents VIIa from binding and prevents generation of active VIIa-tissue factor complex, resulting in a loss of VIIa-tissue factor activity, which can be monitored by coagulation time in factor VII-deficient human plasma. Briefly, varying amounts of the VIIai derivatives were mixed with tissue factor-membrane (1 µL of Innovin per 0.1125 mL of buffer-calcium solution containing 20 nM factor VIIa). Innovin (Dade Co.) is a commercial source of phospholipids and tissue factor. The reagents were allowed to equilibrate for 1 hr at 37° C. then factor VII-deficient human plasma (0.0375 mL) was added and the time needed to form a clot was measured by the manual hand tilt method.

Figure 2A:
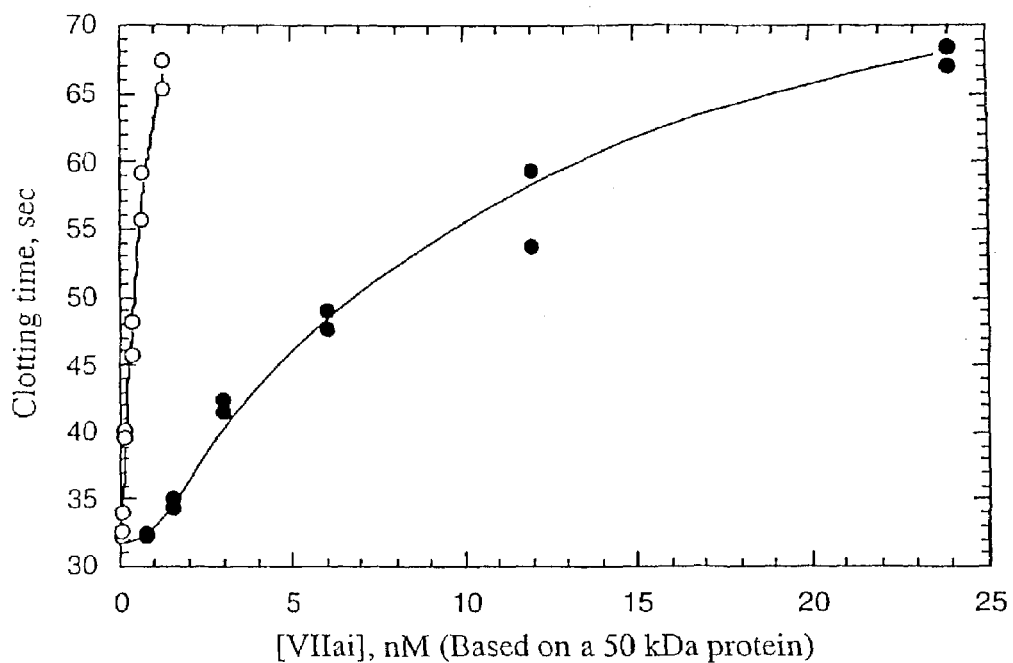
FIGS. 2A and 2B are graphs depicting activity of dimeric proteases.
Figure 3:
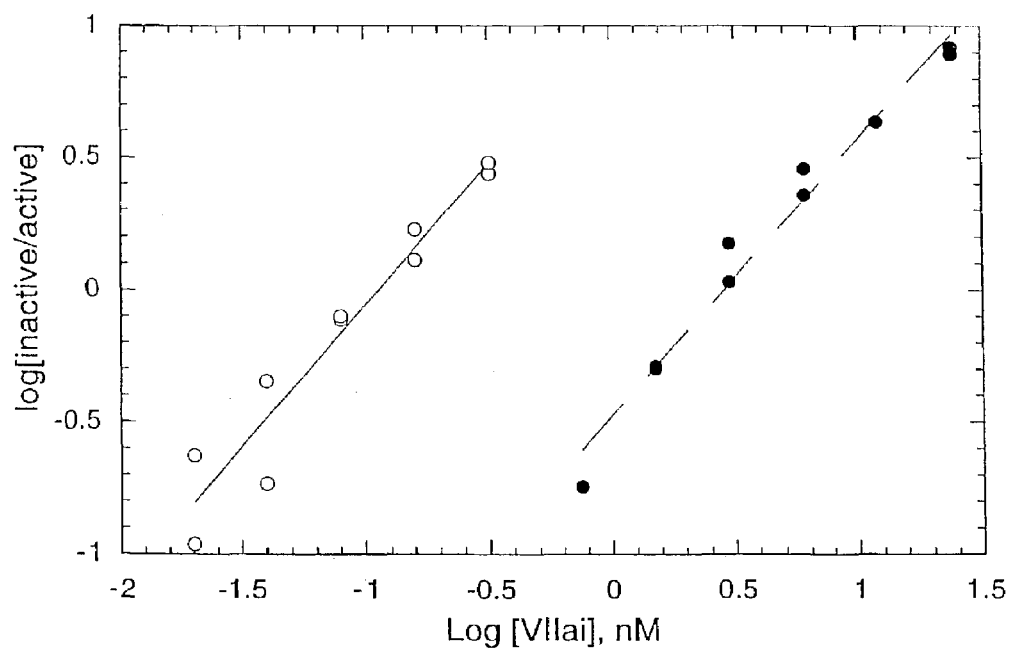
FIG. 3 is a Hill type plot of the activity of the VIIai (solid circles) vs. that of the heterodimer, VIIai-Xai (open circles).

FIG. 2A shows clotting time as a function of added VIIai-dimer and is compared with a similar titration with VIIai monomer. A large advantage of the dimeric protein is evident. To better compare these data, a Hill-type plot was created. Clotting times for various levels of VIIa-tissue factor, in the absence of VIIai, were determined and a standard curve created. The clotting times in FIG. 2A then were used in conjunction with the standard curve, to obtain the concentration of active VIIa-tissue factor complex in the solution. The level of inactive tissue factor-VIIai complex was then determined from equation 1:

$$\text{Fraction of inactive complex} = 1 - \text{fraction of active complex} \quad \text{equation 1}$$

Figure 2B:
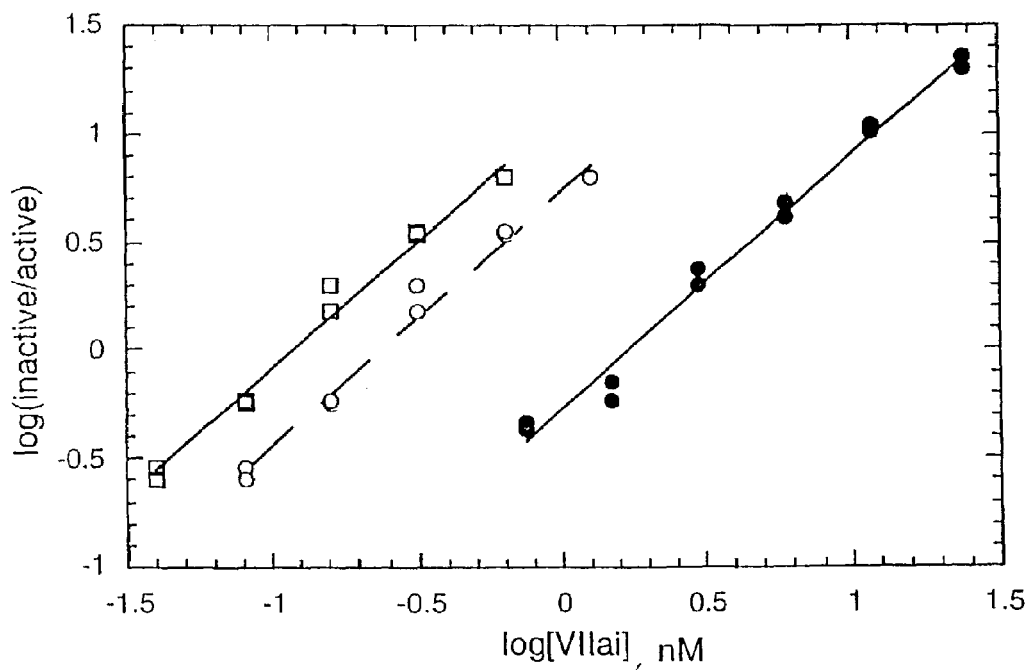

The results were plotted as log (inactive/active tissue factor) vs. log VIIai concentration in FIG. 2B. Two curves are shown for the dimeric protein. In one curve, the concentrations of all proteins were expressed on the basis of a 50 kDa protein to compare the efficacy of dimer vs. monomer on a weight basis. The other curve used the molar concentration of dimer vs. the molar concentration of monomer. On a weight basis, dimeric VIIai had 16-fold higher activity than monomeric VIIai, while on a molar basis, the dimer was 32 times more active than the monomer.

Figure 4A:
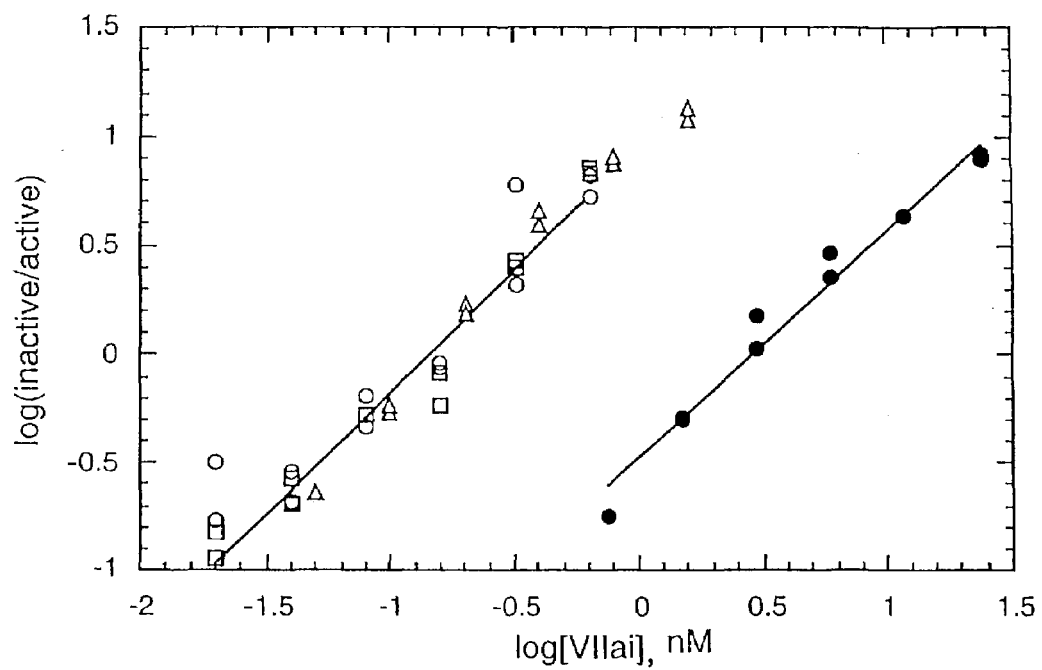
FIGS. 4A and 4B are Hill-type plots depicting activity of inactivated proteases.

The activity of the heterodimer, VIIai-Xai is shown in FIG. 3. This heterodimer had 13-times higher activity than the monomer when compared on a weight basis. Thus, on a weight basis, the homodimer of wild type VIIai and the heterodimer of VIIai-Xai had similar potency. The homodimer of VIIai(P10QK33E) had the same activity as its corresponding monomer (FIG. 4A). In the monomeric form, the Q10E32 mutant has much higher affinity than wild type factor VIIai due to an enhanced membrane binding site. Shah et al. (1998) *Proc. Natl. Acad. Sci. USA*, 95:4229–4234).

Figure 4B:
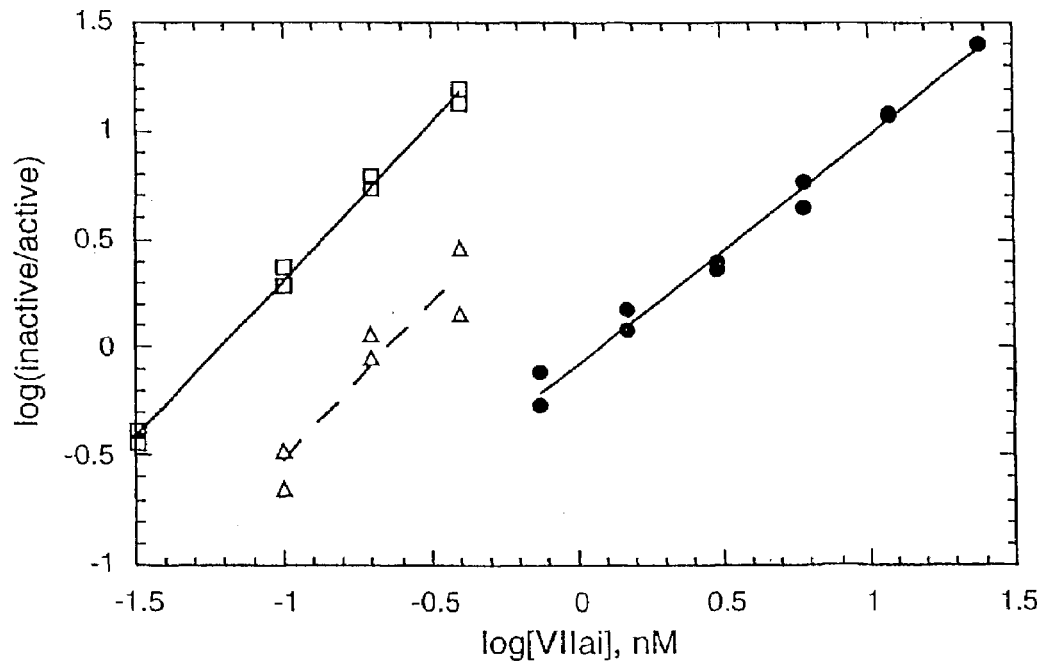
Figure 5:
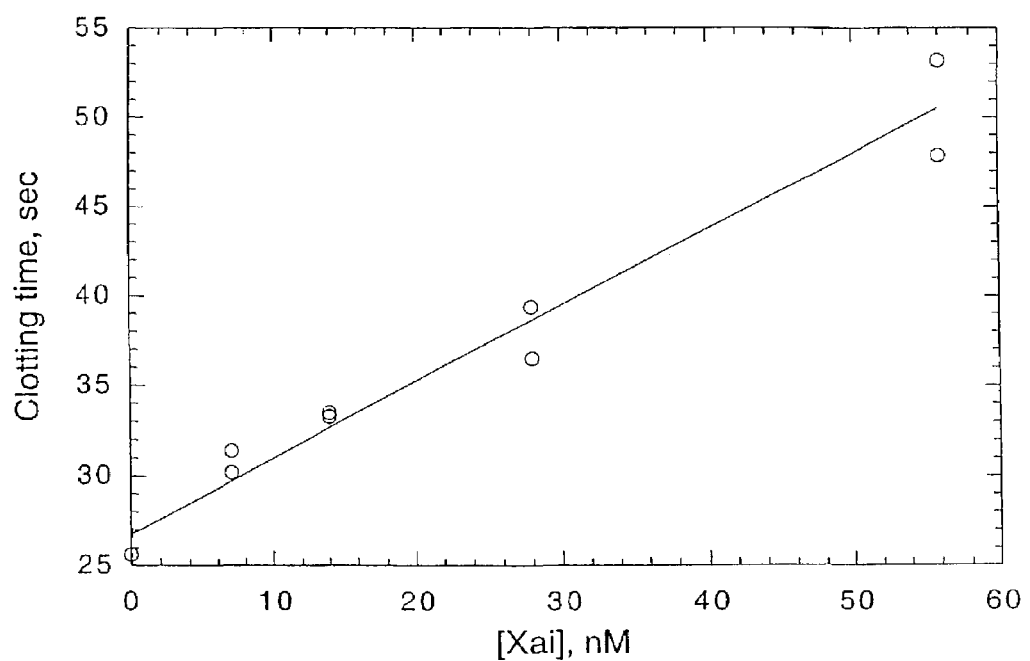
FIG. 5 is a graph of clotting time (in sec.) versus concentration of dimeric Xai (nM).

A heterodimer of mutant factor VIIai(P10Q/K32E) with wild type VIIai had the highest activity, 18-times that of monomeric wild type VIIai on a weight basis using titrations of the type and precision described above. This difference was on the basis of protein weight concentration. Surprisingly, the heterodimer of mutant VIIai(P10Q/K32E) with factor Xai had lower activity than the mutant monomeric protein (FIG. 4B). Thus, dimer formation can have different impacts depending on the proteins used. Again, use of a different crosslinking agent, with altered linker arm, may allow this heterodimer to express higher activity. A homodimer of factor Xa also was an effective inhibitor of blood coagulation (FIG. 5).

Example 6

PEG-modified Factor VIIa Retains Coagulation Activity:

Factor VIIa (3.4 μM, 170 μg/mL) was derivatized with PEG-20,000-SPA at a 30:1 (reagent/protein) ratio in HEPES buffer, pH 8.5, and room temperature to produce factor VIIa with PEG randomly linked via lysine side chains. After reaction was complete (2 hours), the product was analyzed as described in Example 1. Amidolytic activity with soluble tissue factor was monitored and was 67% that of a control reaction. Coagulation activity was measured by a standard clotting assay in factor VII-deficient plasma. Calcium solution (37.5 μL of 20 mM) was the final component added to a mixture of 37.5 μl plasma, 1 μL of Innovin, and 75 μL of buffer. Clotting times were measured and compared to standards reactions with wild type factor VIIa. Coagulation activity of the derivatized protein was 55% that of the control. The reaction also was analyzed by SDS-PAGE, which indicated that almost all proteins had at least one PEG polymer attached. As expected from active site-directed derivatives, the mono-derivatized protein ran at an apparent molecular weight of 100,000. Other bands are detected at positions expected for two, three, and more PEG polymers per protein. This reaction showed that most of the enzyme activity survives one PEG polymer per enzyme.

High retention of activity was not obtained with activated protein C (APC), a protease that inhibits blood coagulation. That is, reaction with PEG and analysis of products by relevant blood clotting methods as well as SDS-PAGE showed that loss of APC activity approximately paralleled the formation of the mono-substituted protein. APC derivatized with a PEG-linked, active-site inhibitor may function as an inhibitor of prothrombinase.

Example 7

Analysis of Factor VIIa Function in Whole Blood of Hemophilia Patients:

Heparin anticoagulation typically is monitored with an ACT (activated clotting time) assay that measures clotting time of whole blood. Commercial instruments are available for this assay; experiments herein used the Hemochron Jr. Signature microcoagulation instrument from International Technidyne Corp.

Several types of cuvettes are supplied with the Hemochron Jr. instrument. The ACT+ cuvette contains an agent to activate the contact phase of coagulation as well as additional phospholipid to support later steps of the coagulation cascade. This cuvette was not useful for factor VIIa assays since four hemophilia patients gave clotting times (126–138 s) that were in the range of normal individuals. A second type of cuvette, the ACT-LR, contains material (Celite) to activate the contact phase of coagulation, but has no added phospholipid. This assay depends on cellular membranes to support the later steps of coagulation. "LR" designates low range, and this assay automatically stops at 400 seconds. In both cuvettes, the range of clotting times for normal individuals tested in this study was 120–180 seconds. In severe hemophilia, activation of the contact phase of coagulation is without impact since factor VIII and/or IX are entirely absent. The presence of Celite or Kaolin is, however, beneficial for evaluation of hemophilia therapy as low levels of factor VIII and IX in some patients will contribute to coagulation. Thus, the ACT assay with the ACT-LR cuvette evaluates total coagulation potential from both the normal pathways and the high dose factor VIIa pathway. The instrument is adjusted to report clotting time in units comparable to the original ACT assay. It therefore records one second for approximately 0.65 actual seconds. The times reported in this example are those provided by the instrument.

The ex vivo response of blood from hemophilia patients to added VIIa was assessed in this example. In order to conduct this analysis with low stress to hemophilia patients, blood from normal individuals also was examined by treatment with anti-factor VIII antibody to generate an ex vivo hemophilia A condition. The assays described in this example were conducted within 2 hours of obtaining the blood sample. Blood samples were divided into fractions so that no sample was mixed and assayed more than 10 times.

Methods and Materials:

Hemophilia population. Hemophilia patients included in the study were attending annual clinics or came to the Hemophilia center or University of Minnesota hospital for other reasons. Carriers of the HIV virus were excluded. A number of individuals with moderate to mild hemophilia were assayed by the in vivo test, but their factor levels were not determined in the coagulation laboratory, and were excluded from this study. Individuals undergoing therapy with prothrombin complex concentrates (PCC) also were excluded as this treatment altered response to factor VIIa. Otherwise, the results of all other individuals from a 15-month period were included in the study. Hemophilia patients with inhibitors were identified by number (1 to 6) and relevant data are given in Table 1. Many of the subjects were assayed on multiple occasions.

Factor VIII and factor IX levels in plasma of hemophilia patients were determined in the Hematology laboratory, University of Minnesota-Fairview Hospitals, using the activated partial thromboplastin time (APTT) according to established protocols. Factor VIII levels were reported as the nearest integer percent, with an error of ±0.5%.

TABLE 1

Summary of subjects

| | Unique Individuals | Total individuals |
|---|---|---|
| Hemophilia population | 54 | 85 |
| Hemophilia A | 33 | 52 |
| Mild/moderate/treated | 17 | 22 |
| Severe | 16 | 30 |
| Hemophilia B | 21 | 33 |
| Mild/Moderate/Treated | 19 | 19 |
| Severe | 2 | 14 |
| Artificial Hemophilia | 17 | 49 |
| Men | 8 | 34 |
| Women | 9 | 14 |
| Total | 71 | 134 |

Artificial hemophilia. Nine volumes of blood from normal individuals were mixed with one volume of 0.1 M sodium citrate. In initial experiments, factor VIII was neutralized by adding 60 μl of affinity purified, sheep anti-factor VIII antibody (Enzyme Research Laboratories, West Lafayette, Ind., protein absorbance at 280 nm=1.19) to 2 mL of anticoagulated blood and incubating for 45 minutes at room temperature. In later experiments, the amount of antibody to be used was determined by titration of one individual and this level then was used subsequently on all individuals. For these experiments, factor VIII was neutralized by adding 1.8 to 4.0 μL of antibodies (in 50% glycerol) per mL of blood (depending on lot number). After one hour at room temperature, a sample (0.1 mL) of the factor VIII neutralized blood was mixed with calcium (2.4 μL of 0.4 M $CaCl_2$) and the clotting time was determined in the ACT-LR. The amount of antibody used was approximately 2-times the amount needed to raise the clotting time to >400 seconds. Depending on lot number, the concentration of antibody in the blood was approximately 6–8 μg/mL of blood.

Artificial hemophilia subjects are identified by letter. Specific results are shown for subject A, a 39-year old African American male, subject B, a 23-year old Caucasian male, and subject C, a 27 year old Caucasian male. Other males ranged in age from 25 to 56. Females in the artificial hemophilia group were 23 to 30 years of age. All subjects were in good health.

Evaluation of factor VIIa function by the ACT assay. To determine if anticoagulation had an impact on the ACT assay, blood was drawn from four patients and the coagulation time immediately was determined in the ACT on a portion of the blood sample. A second portion of the blood was mixed with citrate (9 volumes of blood with 1 volume of 0.1M $Na_3$Citrate) to prevent coagulation then recalcified just before use. Recalcification was achieved by mixing one equivalent of calcium (2.5 μL of 0.4 M $CaCl_2$ to 0.1 mL of anticoagulated blood) per equivalent of citrate used as the anticoagulant. This calcium was added just before loading the sample into the instrument. Blood that was anticoagulated and immediately recalcified gave clotting times that were 0–20% longer than the values obtained with the non-anticoagulated blood. This range was obtained for eight experiments performed on the four normal individuals. The range of clotting times for replicate measurements on each individual was about ±10%. Thus, anticoagulation and recalcification had a relatively small impact on clotting in the ACT. Most importantly, the clotting time for anticoagulated and recalcified blood was unchanged during storage at room temperature for 2 hr. The use of anticoagulated blood and its stability at room temperature allowed many samples to be run on one patient without the trauma of numerous blood withdrawals. Before each assay, the blood was mixed by gentle tipping of the plastic container.

For evaluation of factor VIIa function by the ACT assay, blood was drawn from a peripheral vein of the patients or subjects. A cuff was placed on the arm of the patient and an initial syringe (3 mL) of blood from a peripheral vein was discarded. A second syringe of blood, usually 4.0 mL, was drawn, and the blood was anticoagulated as described above and stored at room temperature until assay. Immediately before assay, 0.1 mL of blood were added to 2.4 μL of 0.4 M $CaCl_2$ contained in a 1.5 mL plastic snap top tube. Factor VIIa was added by pipette (0.4 to 2 μL) and the sample was mixed by drawing about 70 μL into a plastic pipette tip and expelling four times. To avoid introducing air, the pipette tip was kept below the surface of the blood and the pipette was not entirely emptied. About 50 μL of the blood containing exogenous factor VIIa then was applied to the sample cuvette (ACT-LR cuvette) in the apparatus and coagulation time started. Clotting times reported in this experiment represent the average and standard deviation of four determinations.

Determination of VIIa in plasma. Plasma from patients undergoing factor VIIa therapy was analyzed for factor VIIa by dilution into factor VIIa-deficient plasma (Sigma Chemical Co. St. Louis). Briefly, a prothrombin time assay was performed with diluted Innovin® (Dade) as the source of tissue factor and membrane. The assay reaction contained factor VII-deficient plasma (50 μL) and Tris-buffered saline with either factor VIIa or a small amount of plasma from patients treated with factor VIIa (50 μL of 0.05 M Tris, pH 7.5, 0.1 M NaCl containing bovine serum albumin (BSA), 1 g/L). At zero time, a solution of 20 mM $CaCl_2$ (50 μL) containing 2.5 μL of Innovin was added to start coagulation. The time needed to form a clot was recorded using the manual hand tilt method. The assay was sensitive to the range of 10 to 100 pM factor VIIa. Plasma levels of factor VIIa arising from therapy were 30 to 90 nM factor VIIa. These were diluted and mixed with buffer to achieve 10 to 100 pM in the final assay. At the volumes added to the assay, factor VII activity in normal plasma was 1.6 nM. This was subtracted as background so that only factor VIIa from therapy was reported. The concentration in patient plasma was calculated by comparison of clotting time to a standard curve created by addition of pure factor VIIa to the assay. Duplicate samples at three concentrations of VIIa-containing plasma were used to estimate the factor VIIa level.

Results:

Response to factor VIII and IX A dose-response relationship for coagulation time in the ACT-LR was constructed by mixing blood from a normal individual with that from a severe hemophilia patient. A plot of logarithm of coagulation time vs. factor VIII concentration gave a linear relationship with a slope of −0.15. This was virtually identical to the dose-response relationship for the standard plasma APTT assay (data in manufacturer's brochure, Sigma Chemical Company, St. Louis, Mo.). Clotting times of blood from patients with moderate factor VIII deficiency or those with severe deficiency, but with recent treatment, generally fit the same dose-response relationship, indicating that clotting time in the ACT-LR correlated well with factor VIII levels determined by standard methods. In fact, the ACT-LR easily detected a 1% level of factor VIII. Similar correlation and sensitivity were found for factor IX. An experiment of mixing blood of a severe factor IX deficient person with that of a normal person was conducted. A plot of log clotting time versus log (%1X) gave a slope of −0.16, nearly identical to the dose-response relationship for factor VIII (above).

With the ACT whole blood assay, clotting times of normal individuals ranged from 126 seconds to 180 seconds. Two hemophilia patients (I and II) had clotting times of >400 seconds in the ACT-LR cuvette. This is the upper limit of detection and the instrument simply shuts off. Patient I was assayed on two occasions, with the second occasion occurring 10 days after receiving an infusion of factor VIII. Although performed at such a distant time, the impact of this therapy was detected with the ACT, which gave a clotting time of 308 s rather than >400 s without therapy. Thus, the ACT was capable of detecting even modest therapy levels. Two other hemophilia patients were described as moderately deficient (i.e, 1 to 3% of the normal level of factor VIII or IX in their blood). One of these patients was factor VIII deficient (patient III) and the other patient was factor IX deficient (patient IV). Their moderate deficiencies were reflected in the ACT times of 350 and 290 s, respectively.

During the course of these experiments, the ACT-LR outcome for a number of patients did not correlate with the baseline activity reported in the patient's record. In 10 cases, blood from individuals with moderate factor VIII disease (1–3% factor VIII) gave clotting times of >400 s in the ACT-LR, suggesting severe hemophilia (<1% VIII). Evaluation of eight of these patients in the hematology laboratory, on the same day, showed that the ACT-LR was correct and that all eight had <1% factor VIII. Thus, the ACT-LR was able to diagnose severity of factor VIII deficiency. Frequency of home treatment (Table 2) (as provided by the patients) also fits a severe disease state for these individuals. All cases of reclassification from moderate to severe hemophilia involved factor VIII.

TABLE 2

| Prior Classification of hemophilia patient (Percent factor) | ACT-LR analysis (CT) | Simultaneous Hematology lab analysis | Approximate Treatment history[a] |
|---|---|---|---|
| Moderate (2%) | >400 s | <1% VIII | 2x weekly |
| Moderate (3%) | >400 sec | <1% VIII | 1–2x/mo. |
| Moderate (2%) | 391 ± 9 | <1% VIII | 2–3x/wk. |
| Moderate (2%) | >400 sec | <1% VIII | 2x/wk |
| Moderate (1%) | >400 sec | <1% VIII | 1x/Mo. |
| Moderate (1%) | >400 sec | <1% VIII | 2x/wk |
| Moderate (2%) | 399 ± 2 sec | ND (VIII) | 3 days b4 assay |
| Moderate (2%) | >400 | ND (VIII) | 1–2x/Mo. |
| Severe (<1%) | 371 ± 7 | 2% VIII | Zero in >4 mo. |
|  | 323 ± 12 | 1% VIII |  |
| Severe (<1%) | 273 ± 3 | 4% IX[b] | Not available |
| Severe (<1%) | 304 ± 32 | 4% IX[b] | prophylaxis |
| Severe (<1%) | 373 ± 16 | 2% IX[b] | 1x/mo. |
| Severe (<1%) | 202 ± 13 | 11% IX[b] | Prophylaxis, then 0 in past month |
| Severe (<1%) | 237 ± 3 | 2% IX[b] | 2x/mo. |

[a]History provided by patient on a questionnaire at the time of blood sample;
[b]Had not been treated in the previous 4 days.

Six patients were originally classified with severe deficiency, but showed detectable clotting times in the ACT-LR. Five were assayed by the hematology laboratory on the same day and significant levels of coagulation factor were found (Table 2). In general, treatment histories of these individuals fit a less severe disease state. Thus, in every case of re-diagnosis, the ACT-LR gave the correct outcome and was able to detect either factor VIII or factor IX at very low levels. Five of the six instances where a moderate rather than severe deficiency was found involved factor IX. It is possible that the plasma assay, which traditionally is used to assess the hemophilia patients, may miss low levels of factor IX. The only individual reclassified from severe to moderate factor VIII deficiency has a sibling with a moderate disease state (1% VIII). Similarity of sibling disease states also supported this reclassification.

Reclassification from severe to moderate disease was dependent on accurate treatment history reported by the patient, and as such, were made tentatively. If the patient was treated shortly before the assay, but did not report that treatment accurately, a significant level of factor would be found that arose from therapy. In contrast, reclassification from moderate to severe disease did not depend on the patient questionnaire. A recent, unreported treatment would provide a moderate disease state that would fit the earlier diagnosis.

A convenient correlation may exist between the design of ACT-LR instrument and severity of hemophilia disease. The ACT-LR assay was designed to terminate at 400 seconds, which is below a 1% level of factor VIII (CT of about 320 seconds) or the lowest level that provides protection to a hemophilia patient. This correlation may have functional significance. In some cases of surgery, the target CT for heparin anticoagulation therapy is about 300 seconds, a value similar to a moderate hemophilia disease state. Both circumstances define patients who have significant coagulation activity. In one case, this allows limited coagulation during surgery and in the other case, it describes a disease requiring infrequent treatment.

Overall, the ACT-LR allowed convenient and rapid assay. Use of citrate-anticoagulated blood allowed multiple determinations from one blood sample. Only small volumes were needed. The method described in this study combined the speed of a point-of-care instrument with the advantages of multiple measurements.

Response to factor VIIa: Response to VIIa varied among patients. In hemophilia patients II and III, titration with factor VIIa lowered coagulation time of the blood. The relative clotting potential was estimated by comparing the lowered coagulation times to target levels for normal individuals undergoing heparin anticoagulation therapy (for dialysis, 250–300 s, for angioplasty and other catheterization procedures, 300–350 seconds, and for bypass surgery, >400 seconds per the manufacturer of the Hemochron Jr.). Current therapy with VIIa results in a level of about 50 nM, which creates a coagulation potential similar to that of a normal patient who has been anti-coagulated for angioplasty (300–350 s). This is a very modest coagulation potential. Higher doses of VIIa resulted in further decreases in clotting times. Extrapolation indicated that dosage levels of >1000 nM would be needed to approach normal clotting times (180 s). Patient III was about 2-fold more sensitive than patient II.

All individuals showed a response to factor VIIa, with clotting times reduced to easily detected levels. Responsiveness was similar to that of the hemophilia patients, with a 2-fold range of response by the four individuals, as discussed above. The range was to a higher VIIa requirement. That is, two individuals required twice the VIIa to achieve the response discussed above.

For patient IV, titration with factor VIIa had a much smaller impact. The 290 second clotting time of patient IV was reduced to only 240 seconds at 300 nM VIIa, a change of only 50 seconds. The patient who had received factor VIII infusion 10 days prior to analysis showed no detectable impact of factor VIIa until over 200 nM. A plateau of clotting time appeared to be reached at 240 seconds.

Typical responses to added WT-VIIa and QE-VIIa are shown in FIG. 6A. The concentrations are those in whole blood so that levels in plasma would be higher. The common dose for factor VIIa therapy is 90 μg/kg, corresponding to about 50 nM factor VIIa in plasma. This level in whole blood gave a clotting time of 340 s, similar to a one percent level of factor VIII. The response level suggested that normal therapy with WT-VIIa would convert a severe hemophilia condition to a moderate hemophilia. WT-VIIa therapy typically is three or more doses at three hour intervals. For refractory cases, treatment is continued for several days.

The mutant form of factor VIIa, QE-VIIa, was more effective than the wild type protein, giving a clotting time of 240 seconds at 50 nM (FIG. 6A). This mutant has much higher affinity for the membrane and higher coagulation ability in tests such as those depicted in FIGS. 2 and 3. Summaries of other patients are given below.

Variability also was detected in 'artificial hemophilia' blood samples. These blood samples responded to WT-VIIa and QE-VIIa in a maimer analogous to that of blood from severe hemophilia patients (FIG. 6A vs. FIG. 6B). The 'artificial hemophilia' blood samples showed a 2-fold variation in response to factor VIIa. Thus, the ACT analysis provides an indication of individual patient responsiveness to VIIa, information that is valuable in setting individual dosages during therapy.

Dose-response relationships for WT-VIIa and QE-VIIa, similar to the plots in FIGS. 6A and 6B, were determined with 51 titrations of severe hemophilia and artificial hemophilia. The result (FIG. 6A, inset) showed a dose-response relationship that was similar to that for factor VIII and IX. That is, the average slope for a plot of log clotting time vs. log [VIIa] was −0.13 for WT-VIIa and −0.20 for QE-VIIa (FIG. 6A, inset). This dose-response relationship was similar to that for factor VIII and IX (slope=−0.15).

Response to VIIa was not predicted from other coagulation assays of the normal individuals, nor from their normal ACT clotting times. While all assays showed variation among the four normal individuals, shorter clotting time of two individuals in the classic APTT coagulation assay did not correlate with response to factor VIIa. The normal ACT times (without anti-VIII antibodies) also did not correlate with responsiveness to factor VIIa. Thus, assay with factor VIIa in the procedure shown in FIG. 6 may provide a unique measurement for monitoring and designing individual factor VIIa therapies.

Factor VIIa that had been modified by random reaction of PEG with lysine residues (see Example 6) also was tested. The molar concentration of active, modified VIIa was calculated from the amidolytic activity of the preparation versus that of a known concentration of unmodified factor VIIa. On this basis, activity of the PEG-modified protein was very similar to that of unmodified factor VIIa. The range of individual points for the PEG proteins was greater than that that observed for normal VIIa. Greater variation for PEG proteins when assayed in the Hemochron Jr. signature microcoagulation analyzer was also detected during factor VIIa titration of blood from a hemophilia patient with factor VII deficiency. Overall, limited PEG modification of factor VIIa by random derivatization of lysine residues can be used to generate an effective factor VIIa population.

Figure 7:
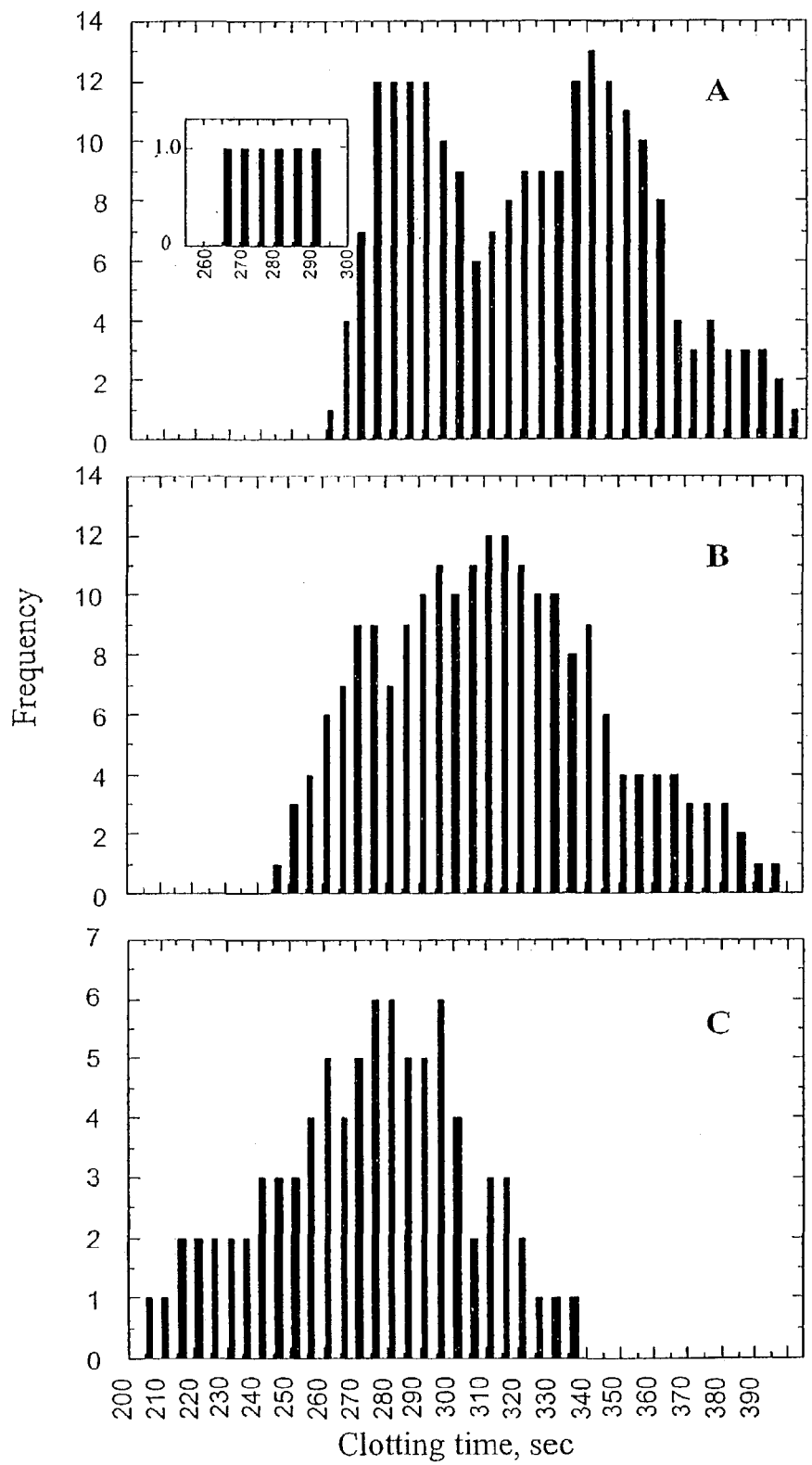
FIGS. 7A–7C are bar graphs depicting the frequency of clotting time (sec) for severe hemophilia patients (7A) and for artificial hemophilia samples from male subjects (7B) and female subjects (7C). The inset of FIG. 7A depicts the manner of data presentation. Each determination was represented by 6 unit bars at 5 second intervals, centered at the average clotting time for the subject. This represented the average and approximate standard deviation for each sample.
Figure 8:
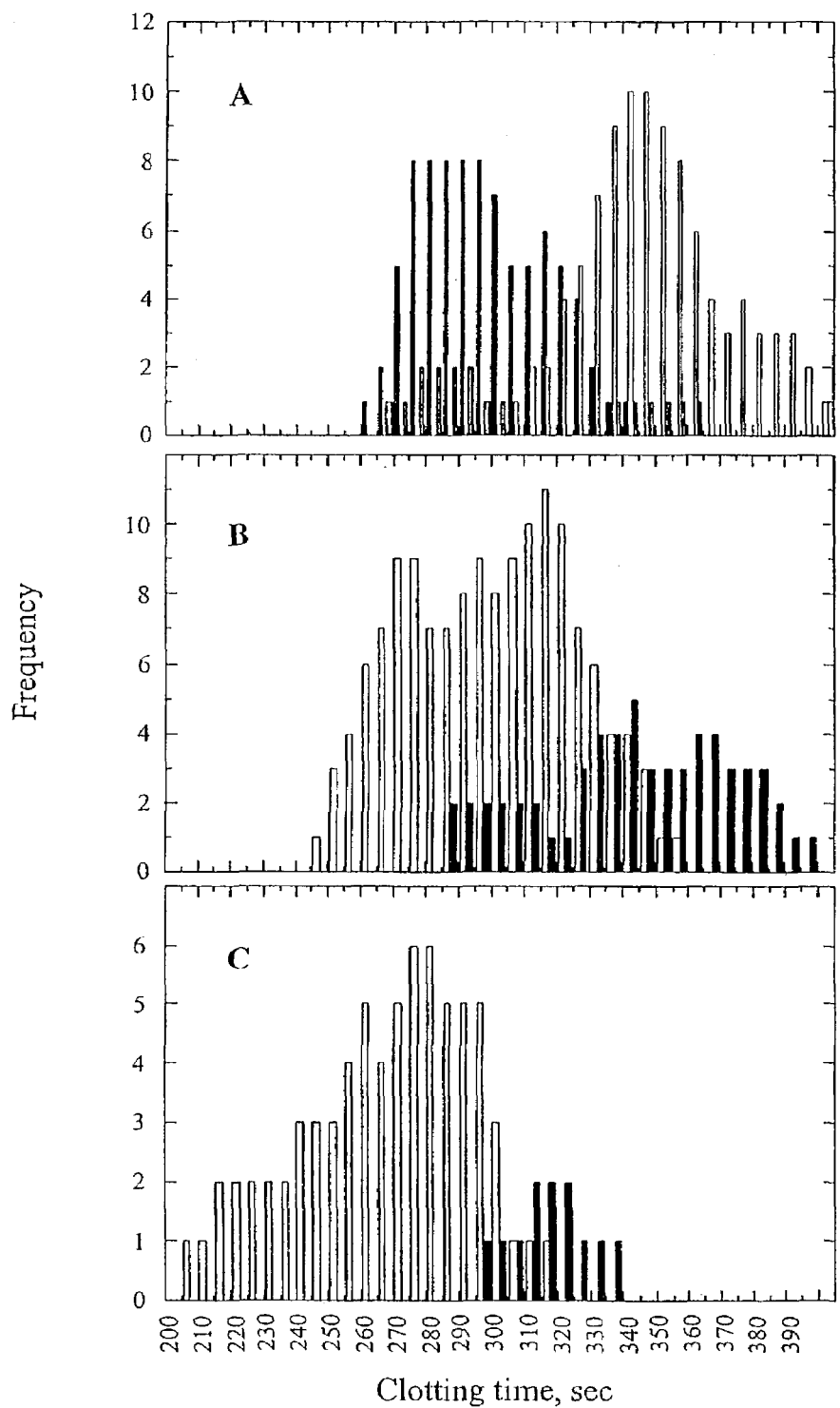
FIGS. 8A–8C are bar graphs depicting the frequency of clotting times (sec) for severe hemophilia patients (8A) and for artificial hemophilia samples from male subjects (8B) and female subjects (8C) in response to factor VIIa therapy.

Responses to WT-VIIa and QE-VIIa. An overview of the results is shown in FIGS. 7 and 8. The data are presented in a manner that represents the average and approximate standard deviation of each measurement. That is, each measurement was given 6 bars, one at each 5 second interval (FIG. 7A, inset). This represented the average and approximate standard deviation (±15 seconds) for each determination.

Results for three groups at 200 nM WT-VIIa are shown in FIG. 7. While far above the normal therapy level, this concentration was selected to ensure that all individuals gave measurable clotting times (<400 seconds). Results are shown for severe hemophilia (FIG. 7A), artificial hemophilia in male subjects (FIG. 7B) and artificial hemophilia in females (FIG. 7C). The range of clotting times was similar for severe hemophilia and artificial hemophilia in males (compare FIGS. 7A and 7B). This suggested that in vivo deficiency of factors VIII or IX did not produce other changes. Females showed higher response to factor VIIa (FIG. 7C) than males. The basis of this difference was not determined. However, the higher WT-VIIa response of artificial hemophilia in females did not extend to the properties of acquired hemophilia in females. The two females with acquired hemophilia gave very low response to WT-VIIa (Table 3). Thus, while artificial hemophilia in blood from male subjects appeared to mimic blood from severe hemophiliac males, the same was not true for females.

TABLE 3

| | | | | Severe hemophilia subjects with inhibitors | | |
|---|---|---|---|---|---|---|
| Patient (sex) | Age | Ethnic Group | Deficiency | Antibody detected at the dilution ratio on (Date) | Therapy (VIIa level during therapy) | Outcome |
| 6 (M) | 38 | Caucasian | VIII | 1:4/1:8 (Apr. 9, 2001) | VIIa | +[a] |
| 5 (M) | 17 | Caucasian | IX | 1:4 (May 4, 2001) | VIIa | ±[b] |
| 4 (M) | 29 | Caucasian | VIII | 1:4/1:8 (Mar. 16, 2001) | VIIa (51, 77, and 95[d] nM) | ±[c] |
| 3 (F) | 56 | Caucasian | VIII[e] | 1:152/1:1024 (Feb. 22, 2001) | VIIa (53 nM) | −[f] |

TABLE 3-continued

Severe hemophilia subjects with inhibitors

| Patient (sex) | Age | Ethnic Group | Deficiency | Antibody detected at the dilution ratio on (Date) | Therapy (VIIa level during therapy) | Outcome |
|---|---|---|---|---|---|---|
| 2 (F) | 51 | Af. Am. | VIII[e] | 1:4/1:8 (Nov. 16, 2000) | VIIa (32 nM) | –[f] |
| 1 (M) | 19 | Af. Am. | IX | 1:128 (Aug. 24, 2000) | PCC | NA |

[A]during the study, there were 35 home therapy treatments without hospitalization;
[b]during the study, there were three inpatient treatments, all for the same chronic elbow bleed;
[c]Despite frequent and aggressive home treatment, subject 4 had 9 hospitalizations for extended VIIa therapy during the study;
[d]Result after home therapy;
[e]Acquired hemophilia;
[f]Subject was switched to other therapy after 3 days of VIIa treatment.

Each group in FIG. 7 contained at least one distinct sub-group. This was illustrated by separation of the data for severe hemophilia patients (FIG. 7A) into three categories (FIG. 8A), one of severe hemophilia without inhibitors and two of severe hemophilia with inhibitors. The apparent biphasic nature of the overall result (FIG. 7A) clearly arose from these different groups. Those with severe hemophilia but without inhibitors showed a uniform, strong response at 200 nM WT-VIIa. In contrast, a group of four patients with inhibitors showed a low response (FIG. 8A). Three individuals in the low response group were assayed while undergoing factor VIIa therapy. Subjects 2 and 3 had completed three days of continuous factor VIIa therapy and showed the appropriate levels of plasma factor VIIa, arising from the 90 μg/kg dose (Table 3). The therapeutic level of factor VIIa did not produce a detectable clotting time. That is, subjects 2 and 3 gave clotting times of >400 seconds. Even with 200 nM additional WT-VIIa, the blood from these individuals gave clotting times of 353 and 387 seconds, respectively.

Subject 4 was evaluated on 3 occasions while undergoing therapy. The levels of factor VIIa in plasma approached 100 nM. Despite these high levels, subject 4 gave a measurable clotting time (383±17 seconds) only once, at 95 nM VIIa. Thus, a low response to exogenous factor VIIa (FIG. 8A) extended to a low response to endogenous factor VIIa arising from therapy. Three individuals in the group with low response in the assay (FIG. 8A) also showed moderate to low response to factor VIIa in clinical situations (Table 3). The fourth does not treat with factor VIIa.

The third group in FIG. 8A consisted of two individuals who showed good to moderate response to factor VIIa therapy. One responded well, treating successfully on 35 occasions in the past year without hospitalization. This person was analyzed on two occasions and showed a high response to factor VIIa (FIG. 8A). The other provided mixed success with three hospitalizations in the past year when home treatment failed. That individual was analyzed on two occasions, showing a strong response on one occasion and a weak response on another (FIG. 8A).

Overall, there appeared to be a correlation between clinical outcome for factor VIIa therapy and response to factor VIIa in the in vitro test.

In a more detailed comparison of the responses to QE-VIIa and WT-VIIa in individual four, it was surprisingly found that QE-VIIa produced a strong response, despite a low response to WT-VIIa. This behavior was detected in other individuals who showed low response to WT-VIIa (Table 4, bottom). That is, the clotting time with 50 nM QE-VIIa was similar that of the larger population (the average for total population is 254 seconds, see below), even though response to 200 nM WT-VIIa was reduced relative to that population (the average for the larger male population was 295 seconds, FIG. 7). Those with lowest response to WT-VIIa, subjects 1 to 3, showed low sensitivity to QE-VIIa as well (Top, Table 4). While QE-VIIa at 50 nM was more effective than WT-VIIa at 200 nM, the clotting time was longer than for others. If this outcome extends to the in vivo therapy, QE-VIIa may provide more consistent therapy for a larger percentage of individuals as well as require lower dosage.

TABLE 4

Low responders to WT-VIIa. Comparison to QE-VIIa.

| | Clotting time at 200 nM WT-VIIa | Clotting time at 50 nM QE-VIIa |
|---|---|---|
| Subject number | | |
| Low response to both WT-VIIa and QE-VIIa | | |
| 3 (+VIIa treatment) | 379 ± 21 | 332 ± 27 |
| 2 (+VIIa treatment) | 342 ± 38 | 340 ± 10 |
| 2 | 387 ± 16 | 365 ± 28 |
| 2 | 363 ± 26 | 373 ± 16 |
| 1 | 324 ± 31 | 321 ± 29 |
| AVE | 359 ± 26 | 346 ± 22 |
| Subject number | | |
| Low response to WT-VIIa, normal response to QE-VIIa | | |
| 2 | 347 ± 8 | 274 ± 9 |
| 4 (+VIIa Treatment) | 353 ± 34 | 291 ± 25 |
| 4 | 353 ± 17 | 283 ± 6 |
| 4 (+VIIa treatment) | 332 ± 21 | 243 ± 26 |
| 4 (+VIIa treatment) | 339 ± 39 | 255 (Ave n = 2) |
| A | 350 ± 22 | 268 ± 12 |
| A | 341 ± 40 | 282 ± 12 |
| A | 325 ± 21 | 273 ± 20 |
| C (+ Ibuprophen) | 372 ± 6 | 282 ± 24 |
| AVE | 346 ± 14 | 272 ± 15 |

The results (FIG. 8A, Table 4) also showed that low response to WT-VIIa was a consistent property of certain individuals. In repetitive assay over extended time periods, hemophilia subjects 1 to 4 nearly always gave low response to factor VIIa. The low response among the artificial hemophilia subjects also came from relatively few individuals (e.g. subjects A and B, FIG. 8B). Another individual, subject C, showed normal response to VIIa on two occasions (CT=265±19 and 299±17 seconds) but low response on two other occasions (369±35 and 372±6 seconds) when he had inadvertently taken Ibuprophen before assay (one response is given in Table 4). Results after taking Ibuprophen are not included in other data summaries.

Women showed limited evidence of sub-groups. However, the two longest clotting times arose from one individual (FIG. 8C).

In male subjects, the average clotting time for QE-VIIa was 254 seconds and the average for WT-VIIa was 357 seconds. These values and the dose-response relationship suggested a difference of 10-fold in efficacy of QE-VIIa vs. WT-VIIa. Since 20% of the values for WT-VIIa were >400 seconds, but were included as 400 seconds, the 10-fold advantage may underestimate the true value.

Comparison of clotting times for women gave an average of 214 s at 50 nM QE-VIIa and 316 s for 50 nM WT-VIIa (n=6). These values and the dose-response relationship provide a 13-fold advantage for QE-VIIa.

Another surprising finding was the uniformly high response among the severe hemophilia population without inhibitors. This differed radically from the hemophilia population with inhibitors (FIG. 8A) and also from artificial hemophilia. Population size appeared sufficient to contain individuals with low response. For example, of the eight artificial hemophilia samples, two of the eight showed low response. Even if those were removed from the population, other artificial hemophilia subjects showed lower response than the severe hemophilia without inhibitors (Compare solid bars, FIG. 8A with cross-hatched bars, FIG. 8B). The basis for high response among severe hemophilia without inhibitors is not known but may suggest other differences in the disease of hemophilia with and without inhibitors.

All sixteen severe hemophilia patients without inhibitors (100%) showed a good response to WT-VIIa while both patients (100%) with acquired hemophilia had low response to WT-VIIa. The artificial hemophilia population showed some individuals with low in vitro response to factor VIIa. Thus, there may be a correlation between low response and the presence of antibodies to factor VIII or IX. Often, individuals with deficiency of factor VIII but without inhibitors show the presence of some factor VIII protein in their circulation. That protein may be inactive, have low activity (<1%) and be insufficient to lower clotting time to a detectable level in the ACT-LR. However, it is possible that a factor VIII protein with very low activity may be adequate to enhance factor VIIa action, either by its cofactor activity or by another mechanism such as enhancing stability of a protein complex.

Example 8

Circulation Lifetime of Proteins in the Mouse:

The mouse is an excellent experimental animal for study of factor VIIai turnover in the circulation. Murine tissue factor does not recognize human factor VII with high affinity and protein turnover can be studied without severe anticoagulation of the mouse.

Factor VIIai was injected into the tail vein of the mouse at time zero and 20 µl of blood were obtained from a small tail injury at various time points. The blood was anticoagulated with 0.1 M Na$_3$Citrate (9 parts blood to 1 of anticoagulant) and plasma was obtained after centrifugation of the cells. Factor VIIai then was assayed using equilibrium conditions, i.e., a competitive assay where VIIa and VIIai were allowed to reach equilibrium with available tissue factor before coagulation was started. The following procedure was developed to allow equilibrium to be reached without interference from coagulation proteins in the mouse plasma. Mouse plasma was diluted 1:49 in 0.05 M Tris buffer, pH 7.5 (containing 0.1 M NaCl and BSA, 1 mg/mL), and Innovin (9 µL/mL) and calcium (to 6.7 mM) were added to activate the clotting proteins in the diluted mouse plasma. After 2 hr, the blood clotting proteases were inhibited by addition of diisopropylfluorophosphate (DIFP) to a concentration of 2 mM. After 12 hours at room temperature, the excess DIFP had spontaneously hydrolyzed and the solutions were assayed for inhibitor proteins. Fractions (0.28 to 5 µL) of the diluted, activated and inhibited plasmas were added to 112.5 µL of buffer containing Innovin (1 µL) and 30 pM factor VIIa in calcium- and BSA-containing buffer. After equilibration at 37° C. for 1 hr, factor VII-deficient plasma (37.5 µL) was added and clotting time recorded. The amount of inhibitor in the plasma was determined from this clotting time and by comparison to clotting times of reactions containing no inhibitor plasma but known amounts of factor VIIai. Initial levels of VIIai in the mouse plasma were 0.33–0.65 µM, representing 50–75% of the theoretical level. The theoretical level was calculated from the assumptions that injection of the protein was quantitative and that a 20 g animal has 1.0 mL of plasma. A small level of inhibitor was detected in control mouse plasma (0.01±0.005 nM) and this was subtracted as a background.

Figure 9A:
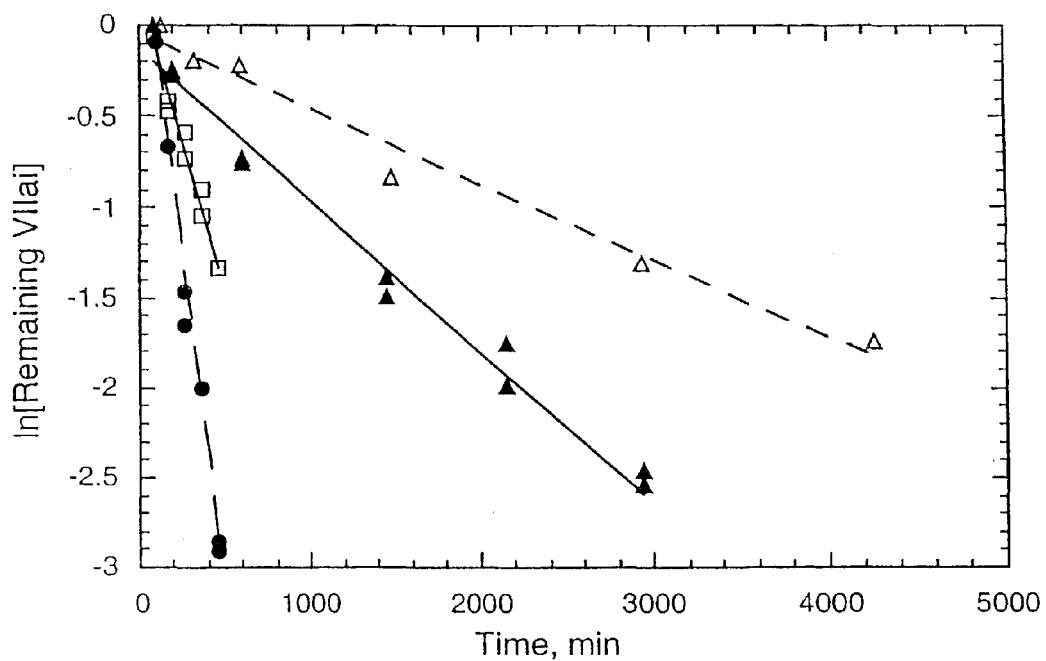
FIGS. 9A and 9B are graphs depicting the circulation time for various factor VIIai proteins in the mouse.

First order decay plots for disappearance of several different factor VIIai molecules from the plasma are shown in FIG. 9A. For direct comparison, all levels of inhibitor are expressed as a fraction of the inhibitor present at the first time point, 80 minutes. Linear analysis of the data provides an estimate of the rate constant for disappearance of VIIai. For wild type VIIai, the average and SD for 3 animals was −0.0074±0.0002/min. This corresponds to a circulation half-life of 94 minutes. PEG(3000)-VIIai was removed from the circulation of two animals with rate constants of −0.0033/min and −0.0034/min, corresponding to a circulation half-time of 207 minutes (2.2-times longer than that of the standard VIIai).

Active site-modified PEG(20,000)-VIIai was removed from the circulation of three experimental animals with a rate constant 0.00081/min±0.00003, corresponding to a circulation half-life of 14 hours. This represents a 10-fold enhancement over normal VIIai. Finally, PEG(20,000)$_2$-VIIai was removed from the circulation of two animals with rate constants of −0.00041/min (data shown) and −0.00044/min (data not shown), corresponding to an average circulation half-time of 27 hours. This is nearly 20-fold longer than that of the monomeric protein. Given that larger species such as the human tend to have much longer protein circulation lifetimes than the mouse, it appears likely that truly extended therapy in the human might be achieved with PEG-derivatized proteins.

Figure 9B:
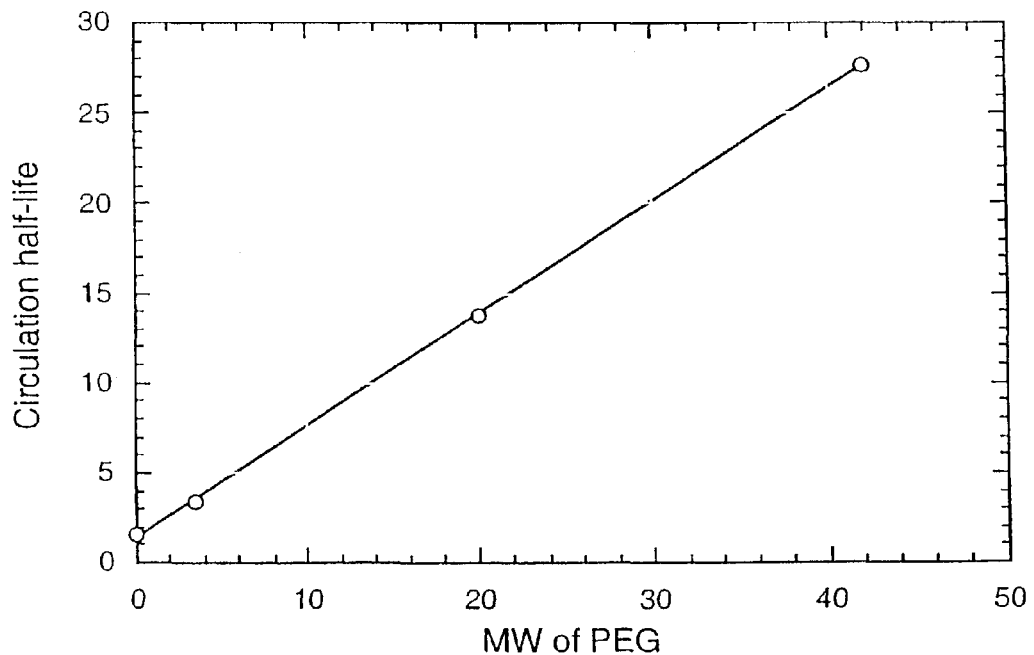

FIG. 9B shows the relationship between molecular weight of the PEG polymer and circulation half-time. The linear relationship was surprising and did not correlate with reports for Fv fragment of immunoglobulins, where an upper limit to circulation time was reported. Thus, it appears that even longer circulation lifetimes are possible for the vitamin K-dependent proteins, provided that larger PEG polymers are attached.

Figure 10A:
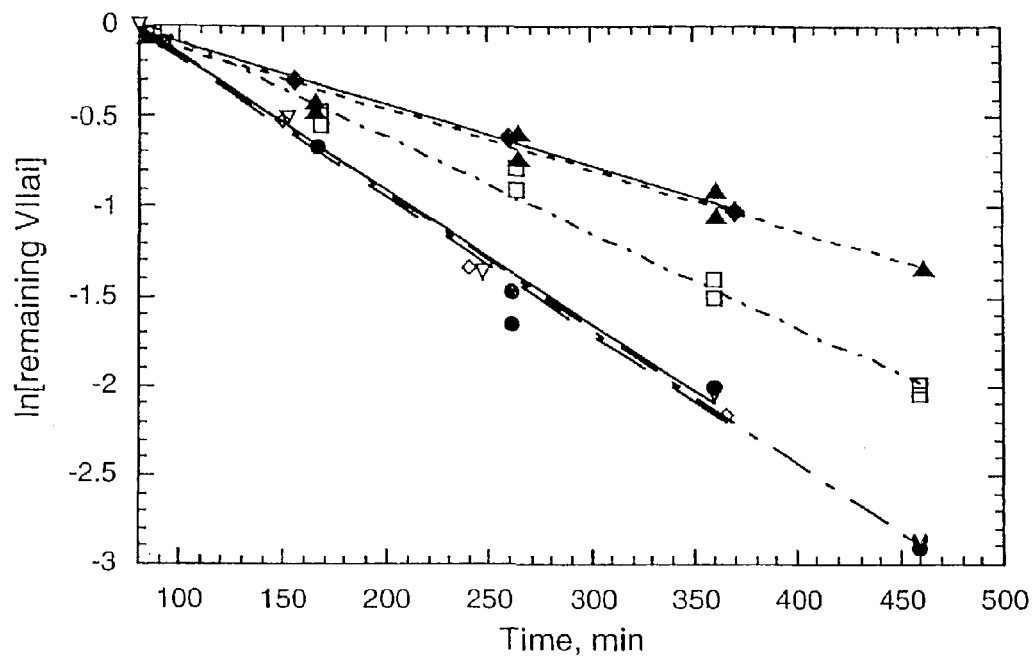
FIGS. 10A and 10B are graphs depicting the circulation time for factor VIIai proteins.

Circulation of other materials is shown in FIG. 10. All three animals given the VIIai proteins are shown in FIG. 8A, along with PEG(3000)-VIIai and dimeric VIIai. The dimer gave a rate constant for disappearance from the blood stream of –0.0052/min, corresponding to a circulation half-time of 139 minutes. Similar results were obtained with the factor VIIai-Xai heterodimer. Thus, a 3000 molecular weight PEG polymer was more effective than protein dimerization with respect to impact on circulation time. The impact of PEG cannot be explained by simple molecular weight change, since dimeric factor VIIai has a molecular weight of 100,000 while PEG(3000)-VIIai has a molecular weight of 53,000.

Figure 10B:
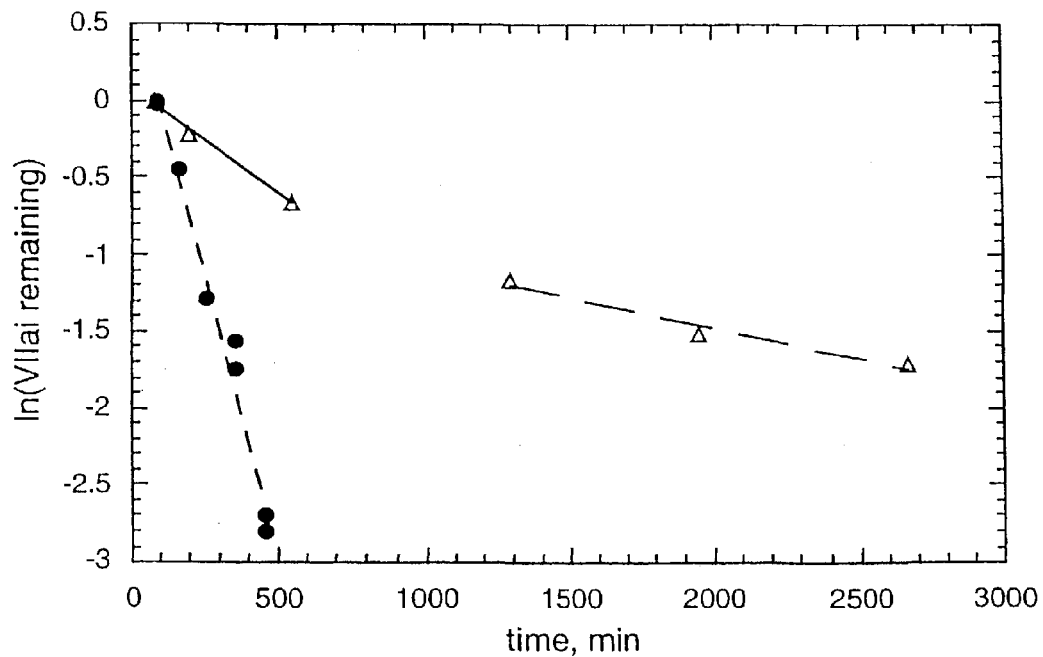

Turnover of VIIai containing random PEG modification of surface lysines is shown in FIG. 10B. Although the VIIa-PEG polymer mixture of Example 6 had activity that was a third less than that of the standard VIIai in the competitive assay described in FIG. 2, the loss of potency was more than offset by increases in circulation time of the derivative. Disappearance from the circulation was biphasic. The initial 50% of the inhibitor activity was lost with a rate constant of –0.00138/min, corresponding to a circulation half-time of 9 hours. This may represent a combination of molecules with no PEG (circulation halftime of 94 min) and mono-derivatized factor VIIai (circulation half-time of 14 hr). The second half of the activity was lost with a rate constant of –0.0004/min. This corresponded to a circulation half-time of 29 hours, very similar to the rate of disappearance of active site modified PEG(20,000)$_2$-VIIai (FIG. 9A). It is possible that this half-time is for protein molecules with two PEG polymers. This suggests that the result in FIG. 9B can be extended to addition of PEG to these proteins, by any mechanism. Thus, increases in circulation half-times appear to be based on molecular size or weight of the PEG polymer.

To test for the impact of PEG(20,000)-CO-FPRck administration, animals were injected four times (0.25 ml volume) with a total of 50 nmols of reagent into one animal over an 8 hr time period. Clotting assays did not detect an increase in coagulation inhibitors in this animal (assayed by the method outlined above), indicating that little inhibition of blood coagulation proteases had occurred in those animals. If proteases were inhibited, prolonged circulation lifetime would cause them to accumulate and an increase of blood coagulation inhibitors would be observed. Over a period of 12 hours, there was no increase in the level of clotting inhibitors in this animal. Thus, PEG reagent containing the active site-directed group may not pose a toxicity problem to an animal. It is possible that excess PEG-modified active site reagent may not need to be removed from a reaction mixture before administration to an animal.

Example 9

Acute Versus Chronic Anticoagulation:

This example describes the reaction of factor VIIai with tissue factor (TF) and the resulting anticoagulation behavior, which was separated into acute and chronic states. As described herein, factor VIIai, mutant forms of VIIai, and other TF-directed agents such as anti-TF antibodies were relatively poor inhibitors of acute coagulation or events that occur within a few minutes of TF exposure. Such agents were 25 to 500-fold more effective during chronic coagulation or events that occur 10 or 20 minutes after TF exposure.

Materials and Methods

Coagulation assays. The 'acute' coagulation assay was performed by mixing, VIIa, VIIai (or Q10E32ai), and factor VII-deficient human plasma (37.5 µL) in 112.5 µL of 0.05 M Tris buffer (pH 7.5) containing 100 mM NaCl and BSA (1 mg/mL). A solution of Tissue factor (Innovin2, Dade, Miami) in 20 mM calcium (37.5 µL) was added to start coagulation.

For 'chronic' state of coagulation, assays were performed by mixing VIIa, VIIai (or Q10E32ai), and TF in 112.5 µL of Tris-BSA buffer containing 6.7 mM calcium and incubating at 37° C. for one hour. Factor VII-deficient plasma (37.5 µL) was added to start coagulation. Equilibrium was assured by reactions started with different order of addition. In one case, TF and VIIa were allowed to assemble before VIIai was added. In the other, VIIai and TF were assembled before VIIa was added. After one hour, these conditions gave the same clotting time. Incubation for 2 hr had no further impact. Coagulation time was determined by the manual hand-tilt method.

Analysis of competition binding. Comparison of WT-VIIai and Q10E32ai binding to TF was accomplished in an assay that used competition with WT-VIIa. Factor VIIa was set at a constant level and concentration of factor VIIai was varied. Briefly, competition of VIIai and VIIa for TF is described by the ratio of equilibrium binding constants (equation 1).

$$K_{DVIIai}/K_{DVIIa} = ([VIIai][TF]/[VIIai*TF])/([VIIa][TF]/[VIIa*TF]) \quad \text{(Equation 1)}$$

This was rearranged to the Hill equation (Equation 2).

$$\text{Log}[VIIai] = \log([VIIai*TF]/[VIIa*TF]) + \log((K_{DVIIai}/K_{DVIIa})[VIIa]) \quad \text{(Equation 2)}$$

A major requirement of equations 1 and 2 was that concentrations represent free protein. Since total protein was known, conditions where designed where [VIIai]total approximated [VIIai]free. This was accomplished with high concentration of competing protein (VIIa) and low concentrations of binding sites (TF).

Coagulation data were converted to the terms of equation 2. The concentration of active enzyme (VIIa*TF) was determined from clotting times for known VIIa*TF concentrations. The slope of log(clotting time) vs. log(VIIa) was –0.30. Clotting time in the presence of inhibitor (CT) vs. that in the absence of inhibitor (CT0, saturating VIIa) allowed estimation of the fraction of active enzyme (VIIa*TF=10^(log(CT0/CT)/0.3). The fraction of inactive enzyme (VIIai*TF) was 1–10^(log(CT0/CT)/0.3). The appropriate term for equation 2 is given by Equation 3.

$$\text{Log}[VIIai*TF]/[VIIa*TF] = \log\{(1-10^{\hat{}}(\log(CT0/CT)/0.3))/10^{\hat{}}(\log(CT0/CT)/0.3)\} \quad \text{(Equation 3)}$$

Validity of these analyses was tested. A plot of log [VIIai*TF]/[VIIa*TF] vs. log [VIIai] should be linear with a slope of 1.0. The average slope for titrations with WT-VIIa and WT-VIIai was 1.12±0.08 (n=15). The average was 1.18±0.11 for Q10E32a and Q10E32ai (n=9). Non-ideal behavior was detected by plots with variable slopes that were much greater than 1.0 (see below). Ideal behavior also required that titrations be insensitive to TF concentration and that plots be shifted in direct relationship to log [VIIa]. These requirements were easily met for WT-VIIai. However, appropriate behavior for Q10E32ai occurred over a more limited range of low [TF] and high VIIa concentrations. Detailed comparisons are presented below. All linear graphs represent the best fit of all data by the program Kaleidagraph.

Factor X activation. Inhibition of VIIa*TF by VIIai also was detected by factor X activation on membranes of J82 cells. Briefly, factor VIIa, VIIai, and J82 cell membranes were incubated for 1 hr at 37° C. in 0.25 mL of Tris-BSA buffer containing 5 mM calcium. Human factor X was added (200 nM, Enzyme Research Laboratory) and the incubation continued for 5 minutes. The reaction was quenched with excess EDTA (8.3 µL of 0.3 M). The factor Xa concentration was determined from absorbance change at 405 nm after addition of 0.32 mM chromogenic substrate (S-2222, Chromogenix) and subtracting background values. Factor Xa concentration was determined by comparison to the activity of pure factor Xa. Data are plotted by the Hill relationship, log [VIIa*TF]/[VIIai*TF] vs. log [VIIa].

Results

Comparison of WT-VIIai and Q10E32ai in anticoagulation. Under chronic coagulation conditions, the mutant Q10E32ai was about 20-times more effective than WT-VIIai, as estimated from the log (clotting time) vs. log [VIIai]. Thus, at equilibrium, the higher efficacy and the benefit of VIIai and its mutant P10Q/K32E become apparent. At equilibrium, 30 nM VIIai is sufficient to block a high level of coagulation (>90% inhibition).

For 'acute' coagulation, factors VIIa and VIIai were both present and TF and calcium were added to initiate the coagulation reaction, mimicking the sudden exposure of tissue factor to the blood stream during injury. If the rate of VIIai*TF assembly were equal to the rate of factor VIIa*TF assembly, and if short-term coagulation were entirely determined by association rate, 90% inhibition would require 10-times as much VIIai as VIIa. Experimentally, a somewhat higher level of VIIai was needed. At 0.48 nM VIIa, 50% inhibition (log (VIIai*TF/VIIa*TF)=0) occurred at 1.5 nM WT-VIIai (log [VIIai]=0.18). At 20 nM VIIa, 50% inhibition occurred at 50 nM WT-VIIai. Overall, kinetic assembly with TF seemed to favor WT-VIIa over WT-VIIai by about 3-fold. High concentrations of factor VIIai were required to inhibit the acute state. At 20 nM VIIa and under chronic conditions, 1.5 or 2 nM WT-VIIai provided 50% inhibition (log (VIIai*TF/VIIa*TF)=0), about 20-fold less than was needed to inhibit acute coagulation. Chronic anticoagulation by Q10E32ai was displaced another 25-fold. Since Q10E32ai was similar to WT-VIIai in the acute state, the difference in function of Q10E32ai in the chronic vs. acute states was over 500-fold. If safety of WT-VIIai arises from action as a chronic anticoagulant, Q10E32ai may offer even greater advantage.

The 25-fold difference between WT-VIIai under chronic vs. acute conditions arose from at least two factors. At equilibrium, factor VIIai had about 7-fold higher affinity in protein-protein contact with tissue factor than did VIIa, and the kinetics of assembly favored VIIa by about 3-fold.

For additional comparison, activity of factor Xai (data from FIG. 5) and activated protein C (wild type and a H10Q/S11G/Q32E/N33D mutant, data from Nelsestuen et al. (1999) *Trends. Cardiovasc. Med.*, 9:162–167) were analyzed. Of these anticoagulants, factor VIIai was the least effective for acute state anticoagulation. APC is effective for treating acute anticoagulation, although it is rapidly inhibited in the blood and has a very short lifetime. Interestingly, the high affinity mutants are not very much better than wild type protein. Lack of difference can be explained by a reaction limited by diffusion of particles in solution. Association rate constants estimated for VIIa binding to tissue factor are $2 \times 10^9$ $M^{-1}$ $s^{-1}$, very near to the collisional rate constant. If acute anticoagulation is dependent on collisional rates, higher affinity will not have an impact. Only at equilibrium, when dissociation rates are also part of the interaction, will the high affinity mutants become effective.

Figure 11:
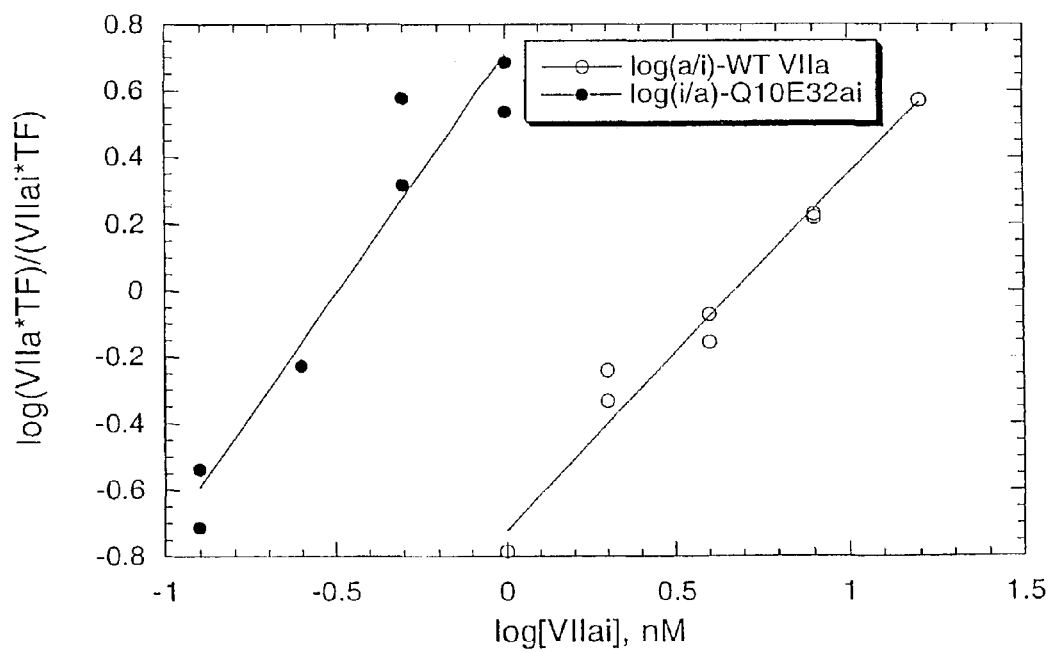
FIG. 11 is a graph depicting factor VII inhibition of reaction on J82 cell membranes. WT-VIIai is represented by open circles and mutant Q10E32ai is represented by solid circles.

Activity of VIIai on J82 cells. A different assay was used to determine if enhanced activity of Q10E32ai occurred on membranes of cellular origin. This was achieved with J82 cells that had been stored at 0° C. for 24 hr to maximize TF expression. Cell membrane particles of J82 cells (from 4000 cells/assay) were incubated for 120 minutes with VIIa (20 nM) and WT-VIIai or Q10E32ai in buffer containing 5 mM calcium and BSA. Factor X was added and the mixture incubated 5 minutes before addition of excess EDTA. Factor Xa concentration was determined by absorbance change with chromogenic substrate (S2222). The results are plotted by equation 2. Again, to approach conditions for accurate comparison, low concentrations of cells were used along with high concentrations of WT-VIIa (20 nM). The difference between Q10E32ai and WT-VIIai was 16-fold (FIG. 11). While not as extensive as studies with reconstituted TF, the difference between WT-VIIai and Q10E32ai on J82 cell membranes was similar, indicating that the benefit of Q10E32ai will be expressed in biological membranes.

Figure 12:
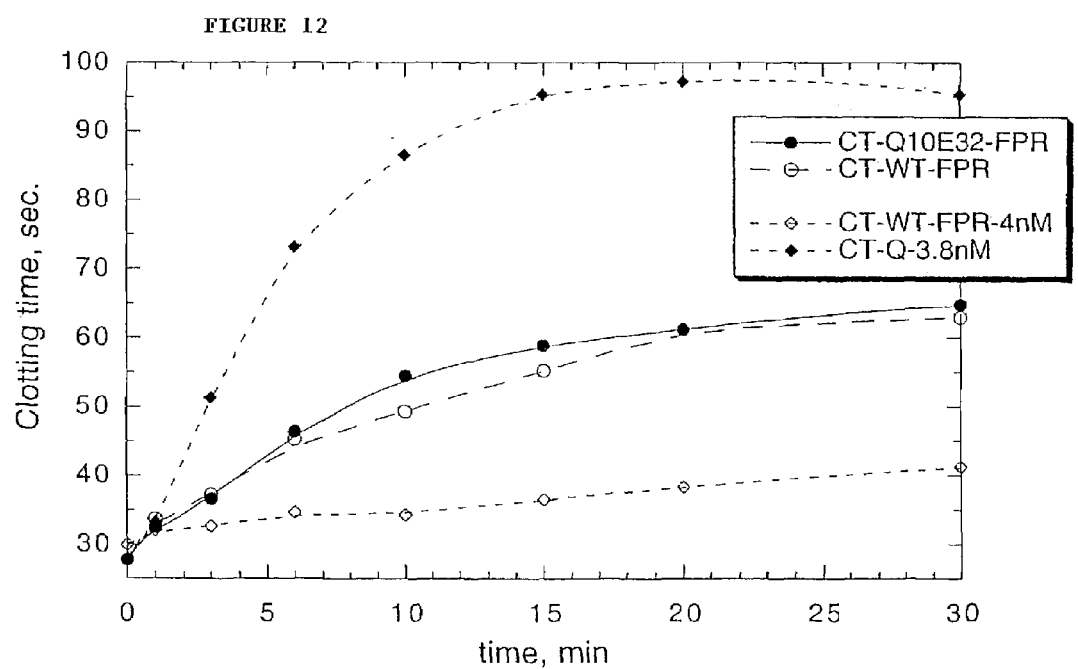
FIG. 12 is a graph depicting the conversion from acute to chronic coagulation states. Both 10 nM (open circles) and 4.0 nm (open diamond) WT VIIai were used. Q10E32ai was used at 0.4 nM (solid circles) and 3.8 nM (solid diamonds).

Conversion of acute to chronic anticoagulation. To assess conversion of acute coagulation to chronic coagulation conditions, low levels of VIIai, insufficient to inhibit acute coagulation, but creating high inhibition at equilibrium, were used. The time course for conversion to the inhibited state was determined by coagulation at various times after mixing. Factor VIIa (20 nM) and factor VIIai were mixed in a large volume of buffer containing 6.7 mM calcium and BSA. At zero time, TF (1.0 µL Innovin/112.5 µL of solution) was added. Samples (112.5 µL) were removed at various times and coagulation was determined after addition of 37.5 µL of factor VII-deficient plasma. The rate of conversion from acute coagulation to chronic (or equilibrium) coagulation is illustrated in FIG. 12. Factor VIIa and VIIai were mixed and TF was added at zero time. The initial result was an acute coagulation situation, with a short clotting time. At 0.4 nM Q10E32ai and 10 nM WT-VIIai, the clotting time increased for about 20 minutes before reaching equilibrium. This showed the standard 25-fold difference between Q10E32ai and WT-VIIai. Inhibition at similar concentrations (4 nM WT-VIIai and 3.8 nM Q10E32ai, FIG. 11) emphasized the enhanced function of Q10E32ai. It is apparent that conversion to equilibrium conditions required 10 to 20 minutes. The results also showed that the rate of approach to equilibrium was dependent on the final equilibrium state and not on the absolute concentration of inhibitor. Thus, chronic inhibition by VIIai fits any situation where tissue factor may be exposed for this time or longer.

Anti-TF, another chronic inhibitor of coagulation. Assays were conducted by mixing factor VIIa (20 nM) and anti-TF (8.9 µg/mL or 36 µg/mL of murine monoclonal anti-TF) in calcium-containing buffer. Innovin (2.2 µL/112.5 µL of solution) was added at zero time. Samples (112.5 µL) were removed at the times shown, mixed with 37.5 µL of factor VII-deficient plasma and clotting time determined (see FIG. 13).

Figure 13:
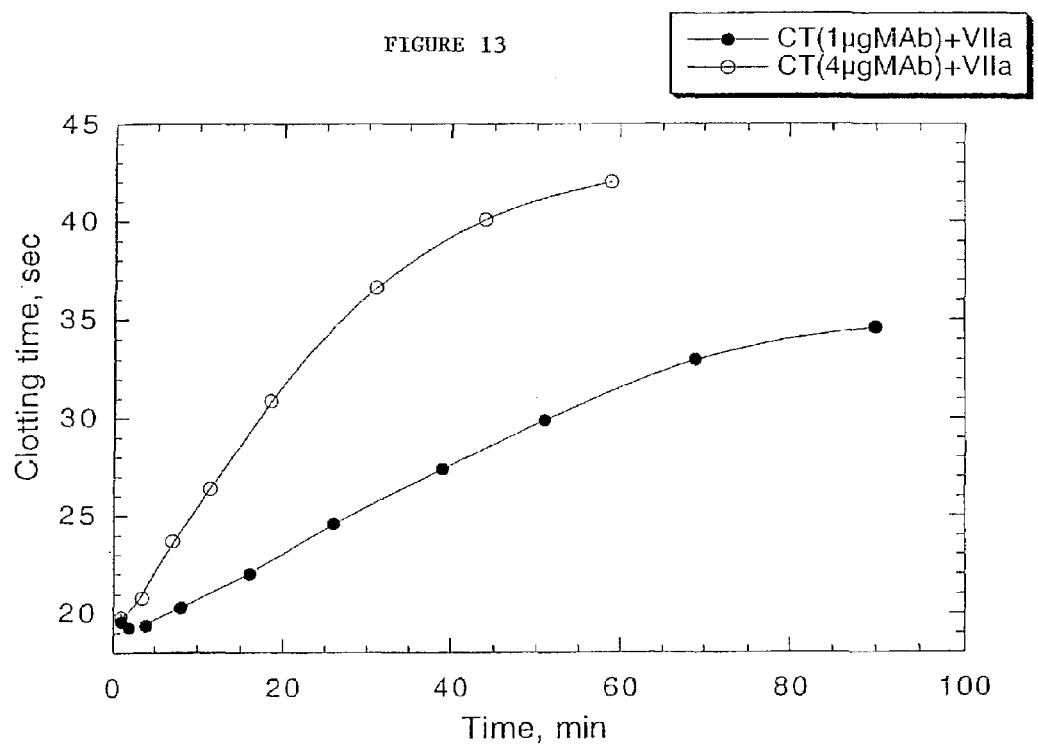
FIG. 13 is a graph depicting acute to chronic conversion with anti-TF antibodies. Inhibition is depicted in the presence of VIIa.

At the concentrations of VII/VIIai in plasma (10 nM), the rate constant for VIIa-TF assembly (approximately $10^9$ $M^{-1}s^{-1}$ should provide full saturation of TF in less than a second. This is much faster than typical antibody-antigen interaction. At 8.9 µg of anti-TF antibody (Prod. #4509, American Diagnostica) per mL, the half time of inhibition, even without VIIa in the solution, was almost 10 minutes. As a result of this disparity in assembly rate, sudden injury and exposure of TF to blood that contains normal VII/VIIa plus anti-TF will result in almost quantitative assembly of VIIa-TF. Coagulation should be normal for the first period of time. In fact, when TF was added as the final component, no lengthening of coagulation time was detected at any level of anti-TF tested in this study. Thus, like VIIai, anti-TF antibody was a poor inhibitor of acute coagulation. However, at equilibrium, anti-TF antibody was a good inhibitor of coagulation (FIG. 13). Polyclonal anti-TF antibody (American Diagnostica) produced similar results and conclusions.

Example 10

Anticoagulation by Wild Type and Variant Forms of Activated Protein C (APC): Impact of Biological Membranes and the Level of Coagulation Stimulus This example describes the impact of 1) biological vs. artificial membranes, 2) type and strength of coagulation stimulus, and 3) the formation of a clot, on dose-response relationships for WT-APC as well as mutant APC having higher membrane affinity (H10Q/Q32E/N33D, QGED-APC). In standard plasma coagulation assays with added phospholipid, WT-APC showed classic behavior of inhibition without limit. In assays with biological membranes from male subjects, however, there was a limit to clotting time corresponding to about 87% inhibition of total activity. A limit may constitute a form of regulation that prevents excess anticoagulation. With biological membranes, QGED-APC had about 20-fold higher function than WT-APC. At high doses, the mutant reached anticoagulation levels not attained at any concentration of WT-APC. With all other parameters constant, a strong stimulus-dependent dose-response relationship was observed. Strong coagulation stimuli gave short clotting times and required high levels of APC. Coagulation reactions with long clotting times showed response at low APC. These properties show that in vitro assays may be adjustable to mimic in vivo situations, if the coagulation task and coagulation stimuli are known.

Materials and Methods

Protein C and APC. Recombinant WT-APC and QGED-APC were produced as described by Shen, L. et al., *J. Biol. Chem.* 273:31086–31091 (1998). Activation of protein C to APC and quantitation of active enzyme also were conducted as described by Shen et al., supra. Protein was frozen in small aliquots that were stored at −70° C. Samples were thawed and used on the same day without refreezing.

Experimental Subjects. Blood (4 to 8 mL) was obtained from four healthy adult males, four healthy adult females, and two healthy adult females who were heterozygous with respect to the APC resistance trait. Most data were obtained from the four male subjects, who were analyzed multiple times and showed individual characteristics with little daily variation. Subject 1 was a male of African descent, age 39. Subject 2 was a male of Northern European descent, age 23. Subject 3 was a male of Hispanic descent, age 43. Subject 4 was a male of Northern European descent, age 56. Subjects 5–8 were females of Northern European descent, ages 23 to 30. Subjects 9 and 10 were females of Northern European descent, ages 25 and 33). An earlier survey had shown that subjects 9 and 10 carried the APC-resistance trait, although neither had a history of coagulation disorders.

One blood sample was from a patient with severe factor VIII deficiency. The blood was mixed in various proportions with that of a normal individual, the mixture was added to calcium solution and assayed in the ACT-LR cuvette as described below.

Coagulation assays. The plasma APTT assay and APTT reagent were obtained from Sigma Chemical Co. (St. Louis, Mo.) and performed according to manufacturer's recommendations. Three lots of reagent were used. One was outdated at the time of assay by approximately three months, but provided a useful comparison.

Whole blood clotting assays. In this example, both ACT time (i.e., the time reported on the Hemochron Jr. Signature microcoagulation instrument) and actual clotting time are presented. ACT time allows direct comparison to heparin anticoagulation, to the anticoagulation target times for various therapies, and to the original ACT test, a less specialized assay. ACT-equivalent clotting time is noted as sec(ACT+), $\sec_{ACT+}$, sec(ACT-LR), or $\sec_{ACT-LR}$, and real time is noted in seconds (s).

Two protocols were used with the instrument. The fresh blood assay followed manufacturer's instructions. In this procedure, fresh blood was drawn from a peripheral vein. A first syringe with 3 mL of blood was discarded and 0.1 mL of blood from a second syringe was immediately added to the cuvette. The second procedure used anticoagulated blood, as described in Example 7. About 50 μL of the mixed sample was added to the cuvette in the instrument and the assay started. The stock tube of citrated blood could be mixed and assayed several times over a 2 hour period without a change in behavior. Citrated, recalcified blood was used for most studies of APC function given below.

Other assays provided for the Hemochron Jr. Signature Microcoagulation apparatus include the APTT and prothrombin time (PT). The APTT assay cuvette contains phospholipids and reports coagulation time in units equal to APTT plasma assay. In this case, actual time was longer than the value reported by the instrument. The PT cuvette contains tissue factor that has been reconstituted into phospholipid bilayers. Both the APTT and PT assays used anticoagulated/recalcified blood. Otherwise, the procedure followed the manufacturer's instructions.

An assay was devised to examine APC action at very low coagulation stimulus. This involved anticoagulating blood with sodium citrate and storage at room temperature as described above. At zero time, blood cells were resuspended by tipping the blood tube as before. Blood was mixed with $CaCl_2$ (12 μL of 0.4 M with 0.5 mL of blood) and added to either WT-APC or QGED-APC in a plastic tube (Falcon 14 mL polypropylene round bottom tube, Becton Dickson Labware, N.J.). APC was added with 5 μL of 50 mM Tris buffer (pH 7.5) containing 0.1 M NaCl plus bovine serum albumin (BSA, 1 g/L). The control (minus APC) gave a clotting time of 11.5±1.1 minutes for subject 4 (n=9). One control was included with each of nine groups of samples (plus APC). Clotting time of the control was not influenced by use of 2.5 to 10 μL of buffer. The samples were incubated at 37° C. and inspected for clot formation every 30 seconds. When coagulation became visible, the samples were inspected every 15 seconds. Inspection involved gently tipping the tube to about a 45° angle and rotating it about 90°. This allowed observation of clots that formed on the side of the tube and ultimately extended into solution. The endpoint was taken when about 75% of the blood was judged to be in a gel state. At this point, the gel was still deformed by the inspection procedure. A solid, non-deformable clot occurred about 60 seconds later. Estimated error in endpoint selection was about ±15 seconds for the control (11.5 minute clotting time) and increased with the clotting time of the sample. Error in endpoint selection at 40 minutes was approximately ±1 minute.

Reconstituted blood. In order to test the role of plasma vs. platelet factor V, blood samples (1.5 mL/tube) from wild type and APC-resistant individuals were centrifuged at room temperature at 10,000×g for 10 minutes. The plasma was removed from each sample with a plastic pipette and mixed with the cells of the other individual. The cells were suspended in the plasma by gentle aspiration into and out of a plastic pipette. Coagulation response was unchanged from that of the original blood samples.

To create protein S-deficient blood, blood of a normal individual was centrifuged and the plasma discarded. Protein S-deficient plasma (immuno-depleted plasma from American Diagnostica) was added and the sample mixed as before.

Results

Modification of the ACT Assay. Results from the ACT assays in which freshly drawn blood was used are shown in Table 5, where 14 samples of fresh blood from 4 individuals were assayed. The data were collected over a 6-month period. Data with the ACT+ cuvette, 6 fresh blood assays from 4 subjects, gave clotting times ($CT_f$) of 108–127 s (Table 5).

Figure 14:
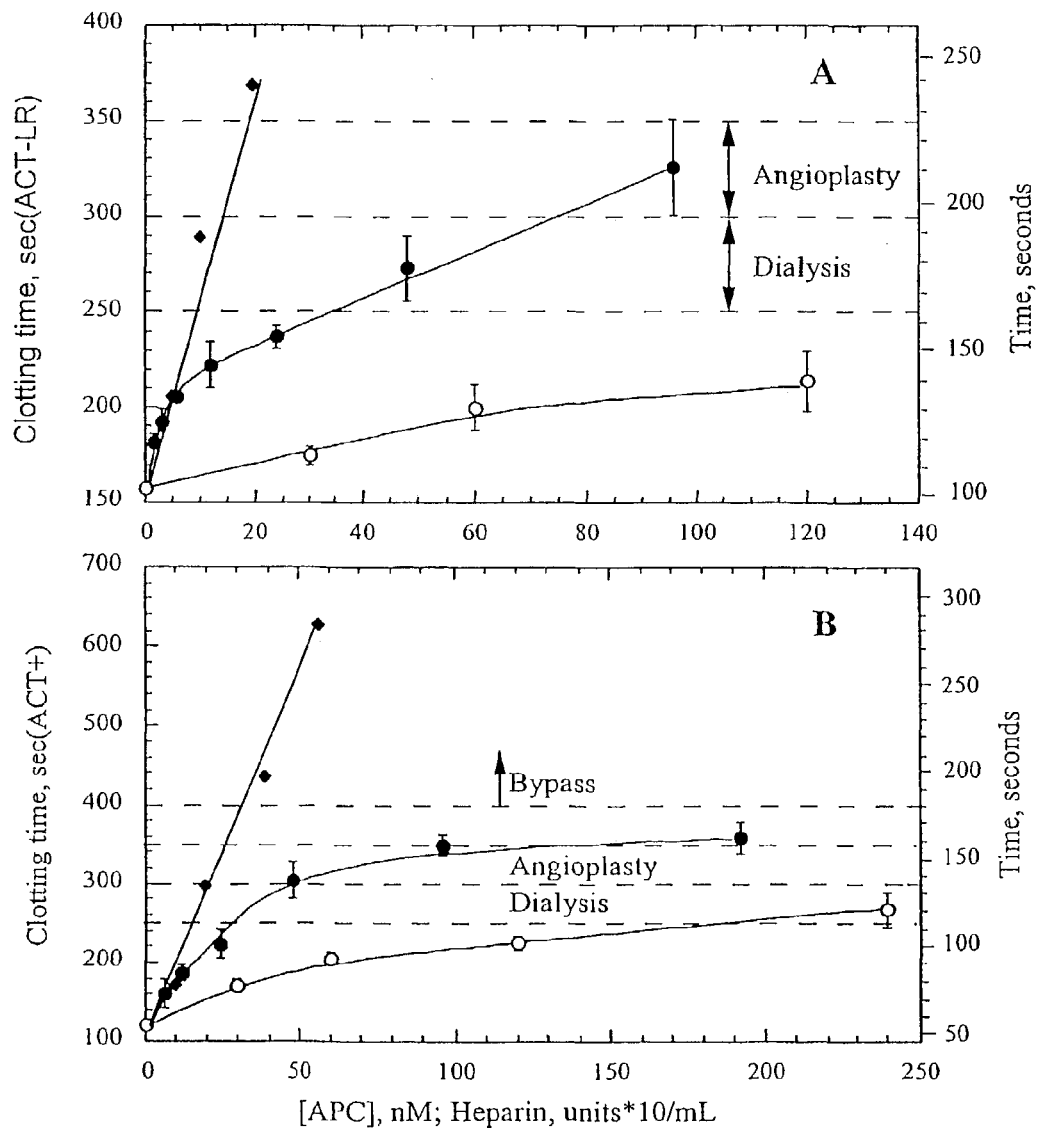
FIGS. 14A and 14B are graphs depicting anticoagulation in activated whole blood assays in the presence (14B) or absence (14A) of phospholipids. The average and standard deviation are shown for WT-APC (open circles) and QGED-APC (solid circles). Single determinations for heparin are shown (solid diamonds). Heparin concentration is given in units*10. Coagulation time reported by the instrument is given on the left vertical axis and real time on the right vertical axis. The target levels of heparin anticoagulation for dialysis, angioplasty and bypass surgery are shown by horizontal dashed lines.

Anticoagulation in the activated whole blood clotting assay: Impact of added phospholipid. FIG. 14 shows the result for anticoagulation by heparin (solid diamonds), WT-APC (open circles), and QGED-APC (solid circles) in the ACT-LR (without phospholipid) and ACT+ (with added phospholipids) assays. Heparin anticoagulation showed a linear dose-response relationship with no apparent limit. This extreme efficacy may contribute to adverse side effects. In contrast, WT-APC reached a maximum clotting time that could not be exceeded. All subjects examined in this study showed this behavior.

TABLE 5

Impact of anticoagulation/recalcification procedure.

| Assay | Clotting time (CT) For Fresh blood | Relative Clot. time recalcified sample $CT_0/CT$ | Rel. Clot. Time After storage $CT_1/CT_0$ | Storage times |
|---|---|---|---|---|
| ACT+ and ACT-LR | Relative value = 1.0 (108–127 sec (ACT+)) (132 to 180 sec (ACT-LR)) | 1.10 ± 0.11 (n = 14) | 1.01 ± 0.06 (n = 8) | AVE = 108 ± 78 MED = 120' Longest = 230' |

Anticoagulated samples were immediately (1 to 6 minutes after the blood draw) recalcified and assayed. Triplicate assays of the recalcified samples in the ACT+ gave clotting times that were 1.12±0.11 fold longer than the coagulation times of the fresh blood. The same approach was applied to the ACT-LR assay. Fresh blood from the same 4 subjects gave clotting times of 132–180 s. Again, the remaining blood was anticoagulated and immediately recalcified. Triplicate samples gave clotting times that were 1.09±0.12 fold longer than the times of the corresponding fresh blood samples.

Overall, anticoagulation with citrate and recalcification resulted in clotting times that were 1.10±0.11 fold longer than that of fresh blood (Table 5). The standard deviation for the $CT_0/CT_f$ ratio was somewhat larger than that of other measurements in this study. This was due to the fact that only one determination was made for the fresh blood. Unless indicated, other assays report the average of triplicate measurements. All subsequent reports are from blood that had been anticoagulated with citrate and recalcified as described. All assays were completed within 2 hours of a blood draw.

Without added phospholipid (FIG. 14A), QGED-APC showed a very large advantage over WT-APC. Comparison of results at a constant clotting time showed that about 20-fold more WT-APC than QGED-APC was needed to reach a given clotting time ($\Delta CT=40$ $sec_{ACT-LR}$, Table 6). Furthermore, QGED-APC reached longer clotting times than that attained with any level of WT-APC. The titration with QGED-APC showed biphasic behavior (FIG. 14A). A rapid rise in clotting time occurred at low QGED-APC concentrations, followed by a slower increase at higher QGED-APC concentrations. As a result, the overall shape for QGED-APC was not a hyperbola expected for a simple saturation process. More complex behavior was suggested. The transition between the two phases was very abrupt and occurred at approximately the maximum clotting time for WT-APC.

TABLE 6

ACT-LR summary.

| Subject | Baseline | WT-APC at $\Delta CT = 40$ $sec_{ACT-LR}$[a] | QGED-APC at $\Delta CT = 40$ $sec_{ACT-LR}$[a] | [WT-APC]: [QGED-APC] |
|---|---|---|---|---|
| 1-male | 183 ± 2 (n = 2) | 20[a] | 1.2 | 16.6 |
| 2 | 175 ± 1 (n = 2) | 75* | 4.0 | 19 |
| 3 | 188 ± 2 (n = 2) | 80* | 2.5 | 32 |
| 4 | 165 ± 2 (n = 2) | 110* | 5.0 | 22 |
| AVE | 178 ± 10 | | | |
| 5-female | 146 ± 3 (n = 3) | 100 nM | 5.0 | 16 |
| 6 | 161 ± 4 (n = 3) | >100 | 6.2 | >13 |
| 7 | 168 ± 4 (n = 3) | 100 | 6.5 | 15 |
| 8 | 154 ± 7 (n = 3) | >100 | 7.0 | >14 |
| AVE | 158 ± 9 | | | |

[a]Concentration obtained from smooth line fit to data by Kaleidagraph program.

With added phospholipid (FIG. 14B), both WT-APC and QGED-APC appeared to be more effective, giving larger relative increases in clotting times. The phenomenon of a limiting value for clotting time was still observed, but the advantage of QGED-APC over WT-APC was about 5-fold and was similar in all four male subjects. The primary reason for a lower advantage of QGED-APC was a 5-fold shift in requirement for WT-APC. Again, QGED-APC reached longer clotting times than were obtained at any level of WT-APC (FIG. 14B).

The actual clotting times (FIG. 14, right vertical axis) showed that the added phospholipid of the ACT+ gave a more potent coagulation reaction. The baseline was 55 s for the ACT+ (FIG. 14B) and 115 s for the ACT-LR (FIG. 14A).

The target clotting times for heparin anticoagulation in various clinical procedures are included in FIG. 14. These demonstrate that very high levels of inhibition are often used. WT-APC reached its maximum clotting time below many of these targets. As discussed below, this may not be related to efficacy as WT-APC may target only the problematic forms of coagulation.

Dose-response relationship. In general, dose-response relationships for WT-APC were observed to vary a great deal with the assay method, and were obtained by plotting logarithm of coagulation time vs. logarithm of protein concentration (factor VIII in this case). Such plots were produced from the clotting times of blood mixed from a normal individual ($CT_0$=155 sec(ACT-LR)) and a factor VIII-deficient individual ($CT_0$>400 sec(ACT-LR)). The slope of the best-fit linear analysis was −0.15. In effect, a 10-fold change in level of a pro-coagulation protein caused a 40% change in clotting time. Although this seemed rather insensitive, it was similar to that of factor IX titration in the plasma APTT assay (Manufacturer's report included with APTT reagent, Sigma Chemical Co). This relationship of clotting time vs. factor VIII level was also in agreement with results for hemophilia patients who have moderate disease.

Figure 15:
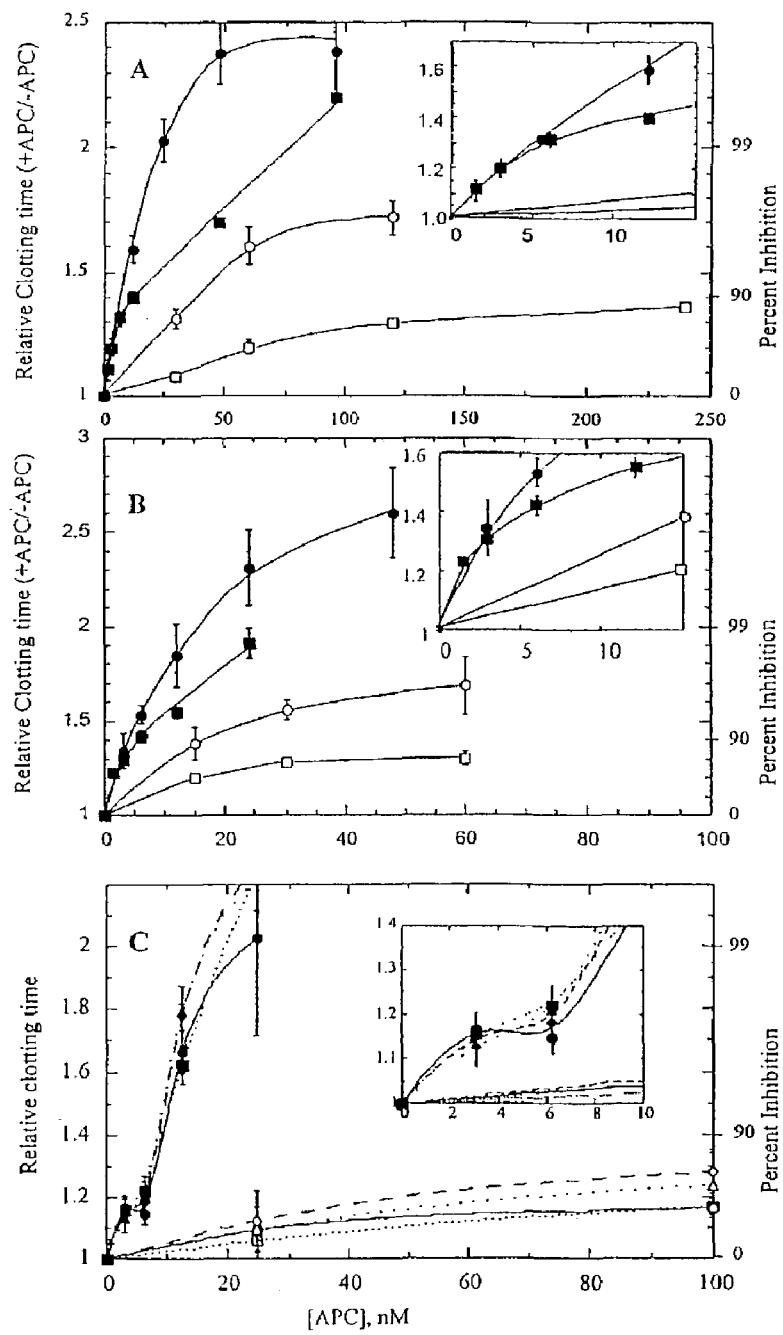
FIGS. 15A–15C are graphs depicting relative anticoagulation for subject 2 (15A), subject 1 (15B), and four females aged 23–30 (15C). Assays in the ACT+ (QGED-APC solid circles) and WT-APC (open circles) and with the ACT-LR (QGED-APC (solid squares) and WT-APC (open squares) were carried out as in FIG. 14. The relative clotting time is the observed clotting time divided by the value without added APC. The inset of FIG. 15A provides an expanded view at low concentration.

The relative coagulation times in the ACT-LR and ACT+ assays were calculated from the dose response relationship, and presented in FIGS. 15A and 15B (left vertical axis). Subjects 2 (FIG. 15A) and 1 (FIG. 15B) provided the extremes of behavior among the male subjects. Subject 1 was the most susceptible to APC. Percentage inhibition (right vertical axis) is based on the dose-response relationship described above. Despite its limited action, WT-APC was an effective anticoagulant. In male subjects, it blocked up to 87% of coagulation in the ACT-LR and 98% in the ACT+ (FIGS. 15A and 15B). Maximum inhibition by WT-APC in the ACT-LR was consistent among the four male subjects, giving an average of 87±3.5 percent (SD, n=4). Again, FIG. 15 showed the large advantage of QGED-APC over WT-APC.

Relative inhibition by QGED-APC in the ACT-LR and ACT+ was similar for the first phase of inhibition (Insets, FIGS. 15A and 15B). This may suggest that all of the QGED-APC was membrane bound in both assays so it gave similar relative inhibition.

The results for female subjects are presented in FIG. 15C. Reaction to WT-APC gave a plateau in clotting time for WT-APC, although with a smaller relative change than for males (FIG. 15C). QGED-APC showed biphasic behavior with an initial plateau that generally correlated with the maximum clotting time for WT-APC (FIGS. 15C and 15C inset). All four females, however, showed a dramatic second phase of anticoagulation by QGED-APC.

Individual variation. The subjects of this study were compared in order to provide information about range of response. Data from plots such as those in FIG. 14 were analyzed by the smooth fit program (Kalideagraph program) and the concentration of WT-APC and QGED-APC needed to increase clotting time by 40 $sec_{ACT-LR}$ was obtained from the curve provided (Table 6). The outcome for both WT-APC and QGED-APC, also apparent in FIG. 15, indicated that subject 1 had about 4-fold higher sensitivity to APC than subjects 2–4. If women were included, the range increased to about 6-fold. Regardless of sensitivity, QGED-APC provided at least a 15-fold advantage over WT-APC.

Coagulation in the plasma APTT assay. The most common assays of APC function utilize plasma and activation of the intrinsic coagulation cascade (the APTT assay). In agreement with earlier studies by Shen et al., supra, the undiluted APTT assay detected little difference between QGED-APC and WT-APC. Response at high WT-APC concentration differed somewhat with the lot of APTT reagent and showed a tendency to reach a maximum clotting time. When observed, the plateau for the plasma APTT assay occurred at very high levels of inhibition (99.9%).

Titration of the four male subjects in the plasma APTT assay indicated that subject 1 was still the most sensitive to WT-APC. The difference, however, was less than that observed in the ACT-LR. For example, subjects 1 and 2 had about a 2-fold difference in the amount of WT-APC needed to reach a specific clotting time. For relative inhibition, subject 2 required only about 1.3 times as much WT-APC as subject 1. Subjects 3 and 4 showed intermediate behaviors. Overall, the plasma assay detected substantially less difference between individuals than the ACT-LR. This may arise from the fact that plasma assays contained only the proteins of an individual while whole blood assays utilized individual proteins plus cells, thereby increasing the potential for variation.

Activation of intrinsic protein C. The impact of WT-APC in the ACT-LR vs. the plasma APTT assay was examined by activation of endogenous protein C. Protac® (American Diagnositica) is a specific activator of protein C that functions in plasma and purified systems. When added (1 unit of Protac®/mL of plasma) to the plasmas of subjects 6 and 7, clotting times in the standard plasma APTT assay were increased from 30±1 see to more than 300 seconds, as expected. When Protac® was added to whole blood of subject 7 (1 unit/mL), the clotting time in the ACT-LR was increased over the control ($CT/CT_0$) by 1.17±0.09-fold. This compared favorably with the limit of WT-APC action; at 100 nM exogenous WT-APC, subject 7 gave a $CT/CT_0$ of 1.17±0.07 (FIG. 15C). When Protac® was added to the blood of subjects 6 and 8, the $CT/CT_0$ ratios were 1.15±0.07 and 1.16±0.09, respectively. These were slightly lower than the limiting values of $CT/CT_0$ for exogenous WT-APC (100 nM, FIG. 15C), which were 1.28±0.08 and 1.23±0.04 for subjects 6 and 8, respectively. Overall, it appeared that addition of exogenous WT-APC or activation of endogenous protein C gave similar anticoagulation activity.

Addition of mutant protein C zymogen (QGED-protein C, 25 nM) to the blood of subject 8 along with Protac® resulted in an ACT-LR clotting time that was 1.44±0.15 times the control value. At 100 nM QGED-protein C, the clotting time was 1.55±0.07 times the control. While these $CT/CT_0$ ratios were somewhat lower than the values obtained by addition of QGED-APC to the blood of subject 8 (FIG. 15C), the qualitative behavior of a large impact by QGED-protein C was maintained.

APC resistance. Resistance to APC is a genetic trait that is linked to increased thrombosis disease. See, Dahlbäck, B., Thromb. Res., 77(1):1–43 (1995). Blood from subjects who displayed this trait was examined in the ACT-LR assay. The APC response of a wild type individual was compared with an individual who was heterozygous with respect to the APC resistance trait. Resistance to both WT-APC and QGED-APC was evident. A second individual with the APC resistance trait gave virtually identical results. QGED-APC showed higher activity toward the APC-resistant individual than the WT-APC showed toward the wild type. Thus, it is possible that QGED-APC will prove effective in therapy of APC resistant patients.

There are two pools of factor V in whole blood, one in the plasma and another in platelets. To test the impact of plasma vs. platelet factor V, blood samples from wild type and APC-resistant individuals were centrifuged to separate cellular and plasma fractions. The samples were recombined to provide a sample containing plasma from an APC-resistant individual mixed with cells from wild type and vice versa. Clotting times for the reconstituted blood samples were virtually unchanged from the parent blood samples. Response to APC followed the plasma fraction. That is, APC response of wild type plasma mixed with APC-resistant cells was similar to that of wild type blood, while the response of APC-resistant plasma with wild type cells was similar to that of APC-resistant blood. The same outcome was obtained with blood from the second APC-resistant individual. Consequently, in this assay, plasma factor V appeared to be the major source for coagulation.

The response of plasma from a individual, homozygous with respect to the APC-resistant trait, mixed with blood cells of a wild type individual was only slightly lower than the response of the heterozygous APC-resistant individual. A 50% change in a coagulation component (APC-susceptible, wild type factor Va in this case) was accompanied by a 10% change in clotting time. This difference was approximately equal to the standard deviation in assays of recombined blood.

Protein S dependent activity. To test protein S-independent activity in the ACT-LR, wild type blood was centrifuged, the plasma removed, and a similar volume of protein S-deficient plasma was added. The outcome was surprising. High levels of WT-APC (100 nM) produced no detectable response in blood lacking protein S. The response to QGED-APC also was reduced. It was not clear if the residual activity of QGED-APC was due to protein S remaining in the sample or if it was truly protein S-independent activity. The primary conclusion was that, when blood cell membranes are used, WT-APC has an almost complete dependence on protein S.

Addition of purified human protein S to the deficient blood returned the response to that of wild type, indicating that the only deficiency in the recombined, protein S-deficient blood was the absence of protein S.

Protein S-independent activity was evaluated in the four different assays provided for the Hemochron Jr. Signature microcoagulation apparatus: the ACT-LR, ACT+, APTT, and PT assays. The results were evaluated for the fraction of activity that was protein S-independent. All of the assays with added phospholipid showed significant protein S-independent activity, ranging from 30% to virtually 100% of the total. Thus, a major determinant of protein S-independent activity appeared to be added phospholipid. WT-APC activity on blood cell membranes appeared to have an absolute requirement for protein S.

The protein S-independent activity varied in inverse relationship to the benefit of QGED-APC. Those situations that showed greatest dependence on protein S also showed the highest benefit of QGED-APC.

Titration of the protein S-dependent response gave a sigmoidal curve shape and reached the saturation response at normal levels of protein S (20 to 25 µg/mL). About 60% of the protein S in plasma exists as a high affinity complex with C4B-binding protein and does function as a cofactor for APC. Consequently, the first 12 to 15 µg/mL should bind to C4b-binding protein and have no impact on coagulation.

These results showed that the whole blood clotting assay was sensitive to protein S and could be used to detect protein S deficiency. Since the whole blood assay detects only free protein S, any form of protein S deficiency should be observed. Since QGED-APC gave a larger change in clotting time than WT-APC, the mutant may provide a more sensitive detection of protein S deficiency.

Dose-response relationships of in vitro assays. Analysis of blood from one individual by several assays showed a large dose-response range for WT-APC (Table 7). At 10 nM WT-APC, clotting time was increased by 10% in the ACT-LR assay vs. 300% in the plasma APTT assay. The response in an assay initiated by factor Xa varied with the phospholipid used, ranging from a 40 to 270% change in clotting time at 10 nM WT-APC (Table 7). Since PE increases the affinity for vitamin K-dependent proteins for membranes, it was clear that membrane affinity was a major variable for dose-response relationship. High affinity phospholipids lowered the dose-response relationship. An important point was that any dose-response relationship could be generated by manipulation of this exogenous component. Consequently, development of relevant in vitro assays was focused on whole blood assays that do not contain added phospholipid.

TABLE 7

Dose-response in assays with strong pro-coagulant stimuli (Subject 4).

| Assay | [WT-APC] | CT(+APC)/CT$_0$ | Activity remaining | Source |
|---|---|---|---|---|
| ACT-LR whole blood assay | 10 nM | 1.11 ± 0.09 (n = 8) | 48%[a] | Measured as in FIG. 2 |
| APTT-plasma assay | 10 | 2.4–3.0 | <0.4%[a] | FIG. 8 |
| Factor Xa addition with PS/PC 20/80 | 10 | 1.4 | 30%[b] | Shen et al., supra |
| Factor Xa addition with PS/PC/PE (20/40/40) | 10 | 2.7 | 4%[b] | Shen et al., supra |

[a]Calculated from a slope of −0.15 for data presented in the plot in FIG. 2.
[c]Calculated from a slope of −0.30 for a plot similar to that of FIG. 2.

Even with biological membranes, dose-response seemed to vary with the strength of coagulation stimulus. For example, the ACT-LR assay contains an activator of the intrinsic coagulation cascade. Coagulation times were short (<2 minutes) and 10 nM or more WT-APC was needed to impact on coagulation time. Anticoagulation by WT-APC in the Clot Signature Apparatus (CSA®), an assay that does not contain an activator of the intrinsic pathway, provided long clotting times (14.7±1.5 minutes for subject 4) and substantial response was detected at 3.75 nM WT-APC. A possible explanation for this difference in dose-response was the level of coagulation stimulus. Situations with high stimuli (e. g. the ACT-LR) may require high levels of WT-APC. To test this suggestion, an in vitro whole blood coagulation assay was devised with a low coagulation stimulus.

Figure 16:
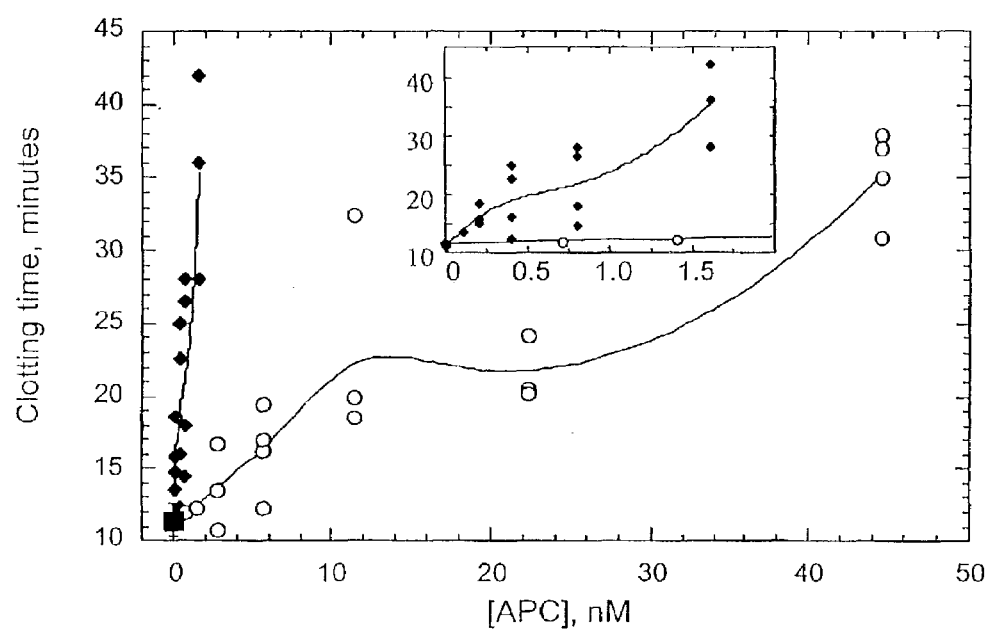
FIG. 16 is a graph depicting the action of APC at low coagulation stimulus.

Blood (subject 4) was mixed with sodium citrate and stored at room temperature in the standard manner. At zero time, the blood cells were mixed and calcium (12 µL of 0.4 M) plus either WT-APC (open circles) or QGED-APC (solid diamonds), in 5 µL of Tris buffer containing 1.0 g/L of bovine serum albumin, were added to 0.5 mL of blood in a 15 mL plastic round bottom tube. The tube was incubated at 37° and visually inspected every 15 to 30 seconds for coagulation. Blood was maintained in plastic tubes to avoid extensive activation of the intrinsic coagulation cascade. Coagulation time corresponded to a state with 75% gel formation. Clotting times of the control were 11.5±1.1 minutes. Low levels of WT-APC and QGED-APC caused dramatic increases in clotting times (FIG. 16). Although results for blood containing APC were less reproducible than the control, a significant response was detected by a 1.4±0.3-fold increase in clotting time at 5.6 nM WT-APC (average=16.3±3 minutes, SD) or a 1.64±0.52-fold increase at 0.4 nM QGED-APC (clotting time=18.9±6 minutes, FIG. 16). While data variation did not allow precise values, the outcome suggested that the advantage of QGED-APC over WT-APC was similar to that observed in the ACT-LR (above).

The results of the unstimulated clotting assay were consistent with two-phase inhibition by both QGED-APC and WT-APC. That is, when analyzed by a best smooth line fit to the data analysis (Kaleidagraph), both showed a plateau of coagulation time at about 20 to 25 seconds with larger increase at higher APC levels (FIG. 16). Overall, the results indicated a strong relationship between coagulation stimulus and concentration of APC needed to inhibit the reaction.

The stimulus-dependent dose response phenomenon is critical to design of appropriate in vitro assay to monitor the target of in vivo therapy. Thrombotic status with low coagulation stimuli in vivo, should be monitored by assays with low coagulation stimulus in vitro. An example of such an assay is given in FIG. 16. In vivo conditions with low thrombotic tendencies may include chronic situations such as cancer, sepsis, or arteriosclerosis. On the other hand, thrombotic states with high coagulation stimuli in vivo should be assay with a strong stimulator in vitro. An example is the ACT-LR, which contains an activator of the contact phase of coagulation (FIG. 15). Examples of strong in vivo stimuli include catherization, surgery, or other invasive methodology.

Example 11

Assay for Tissue Factor (TF) in Blood:

Trace levels of TF were detected in blood samples according to the following procedure. Blood was drawn from a peripheral vein and anticoagulated as described above with 0.1 volume of 0.1M sodium citrate. Antibodies to factor VIII (or antibodies to factor IX) were added in an amount sufficient to eliminate detectable activity. Twice as much antibody as was needed to raise the coagulation time to greater than 400 seconds was used. The factor VIII neutralized sample was divided into two portions. An anti-TF monoclonal antibody (5 µg of product 4509, American Diagnostica per ml of blood) was added to one portion and control antibodies (anti-streptokinase monoclonal antibody, American Diagnostica) were added to the other portion. The samples were incubated for approximately one hour then assayed using the whole blood assay described above in the presence of added factor VIIa (approximately 200 nM or enough to produce clotting times less than 200 s). Clotting times of the samples with and without anti-TF antibodies were compared. Over 40 blood samples were examined.

In general, individuals who responded poorly to 200 nM VIIa (i.e., clotting time of 360 to 390 s in the ACT-LR assay) did not have an increase in coagulation time in the presence of anti-TF antibodies. Thus, their blood appeared to be free of TF. Within experimental error, those individuals who gave shorter clotting times (<330 s) in the absence of anti-TF antibodies showed sensitivity to anti-TF antibodies and longer clotting times with the antibody than with control antibody.

An interesting example of possible TF exposure in a thrombogenic situation was observed for patient 3 (Tables 3 and 4, FIG. 8A). This hemophilia patient normally has low sensitivity to factor VIIa, with clotting times of 330 to 387 s at 200 nM factor VIIa. On two occasions, however, this patient was assay at the end of dialysis, a thrombogenic procedure that is accompanied by heparin therapy with normal individuals. The instrument and dialysis membranes may damage cell and expose TF. Since patient 3 has hemophilia, no anticoagulation therapy was used. At the end of dialysis, bloom from patient 3 showed a strong response to 200 nM factor VIIa (297±16 and 305±24 s). Addition of anti-TF antibodies resulted in clotting times of 385±18 and 379±21 s, respectively. Thus, most of the thrombogenic activity arising from dialysis appeared to be circulating TF.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method for managing anticoagulation therapy in a patient in need thereof, said method comprising administering an acute phase anticoagulant to said patient during the acute phase of coagulation; and administering a chronic phase anticoagulant to said patient during the chronic phase of coagulation wherein said chronic phase anticoagulant is an active-site inhibited factor VIIa linked to a PEG polymer, and wherein said active-site inhibition is effected by linkage of an active-site inhibition reagent to the active site of factor VIIa.

2. The method of claim 1, wherein said acute phase is during surgery.

3. The method of claim 1, wherein said acute phase anticoagulant is heparin.

4. The method of claim 1, wherein said active-site inhibited factor VIIa polypeptide contains a substitution of a glutamine for proline at position 10 and a glutamic acid for lysine at position 32.

5. The method of claim 1, wherein said acute phase is during catheterization or angioplasty.

6. The method of claim 1, wherein said PEG polymer is linked via the active-site of said factor VIIa polypeptide.

7. The method of claim 1, wherein the active-site inhibition reagent is a chloromethylketone-derivatized amino acid or peptide.

* * * * *

UNITED STATES PATENT AND TRADEMARK OFFICE
CERTIFICATE OF CORRECTION

| | | |
|---|---|---|
| PATENT NO. | : 7,160,540 B2 | |
| APPLICATION NO. | : 10/312685 | |
| DATED | : January 9, 2007 | |
| INVENTOR(S) | : Gary L. Nelsestuen | |

It is certified that error appears in the above-identified patent and that said Letters Patent is hereby corrected as shown below:

Title Page, Item [54] and Column 1 Title, please delete "Clottings" and insert --Clotting--therefor;

Title Page, Item [56] References Cited, Other Publications, Harker et al. reference, please delete "Antothrombotic" and insert --Antithrombotic--therefor;

Title Page (Page 2), References Cited, Other Publications, Monroe et al. reference, please delete "independen" and insert --independent--therefor;

Page 1, Column 1, lines 16-18, please delete "Funding for work described herein was provided in part by the federal government, which may have certain rights in the invention." and insert --Funding for work described herein was provided in part by the National Institutes of Health, grant no. HL60859. The federal government may have certain rights in the invention.--therefor.

Signed and Sealed this

Fifteenth Day of May, 2007

JON W. DUDAS
*Director of the United States Patent and Trademark Office*